United States Patent
Sastri

(10) Patent No.: US 10,934,334 B2
(45) Date of Patent: Mar. 2, 2021

(54) PEPTIDES FOR ANGIOGENIC THERAPY

(71) Applicant: The Regents of the University of California, Oakland, CA (US)

(72) Inventor: Mira Sastri, San Diego, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 16/465,808

(22) PCT Filed: Jan. 25, 2019

(86) PCT No.: PCT/US2019/015210
§ 371 (c)(1),
(2) Date: May 31, 2019

(87) PCT Pub. No.: WO2019/147979
PCT Pub. Date: Aug. 1, 2019

(65) Prior Publication Data
US 2019/0389922 A1    Dec. 26, 2019

Related U.S. Application Data

(60) Provisional application No. 62/622,012, filed on Jan. 25, 2018.

(51) Int. Cl.
| | | |
|---|---|---|
| *C07K 14/515* | (2006.01) | |
| *A61K 47/60* | (2017.01) | |
| *A61P 35/04* | (2006.01) | |
| *A61P 35/00* | (2006.01) | |
| *C07K 14/47* | (2006.01) | |
| *A61K 38/00* | (2006.01) | |

(52) U.S. Cl.
CPC ............ *C07K 14/515* (2013.01); *A61K 47/60* (2017.08); *A61P 35/00* (2018.01); *A61P 35/04* (2018.01); *C07K 14/47* (2013.01); *A61K 38/00* (2013.01); *C07K 2319/00* (2013.01)

(58) Field of Classification Search
CPC ............................. C07K 14/515; A61K 47/60
See application file for complete search history.

(56) References Cited

U.S. PATENT DOCUMENTS

| | | | | |
|---|---|---|---|---|
| 8,110,365 | B2* | 2/2012 | Dworkin | G01N 33/573 435/7.1 |
| 8,715,645 | B2 | 5/2014 | Bellgrau et al. | |
| 2002/0019040 | A1 | 2/2002 | Noteborn et al. | |
| 2006/0241067 | A1* | 10/2006 | Varner | C12N 9/1205 514/44 R |

FOREIGN PATENT DOCUMENTS

WO    2019147979    8/2019

OTHER PUBLICATIONS

King et al., 2011, The Rate of NF-kappaB Nuclear Translocation Is Regulated by PKA and A Kinase Interacting Protein 1, PLoS ONE, 6(4): e18713 (15 pages).*
Lim et al., 2008, NF-kappaB p65 regulates nuclear translocation of Ku70 via degradation of heat shock cognate protein 70 in pancreatic acinar AR42J cells, The International Journal of Biochemistry & Cell Biology, 40: 2065-2077.*
Taylor et al., 2006, Human chromosome 11 DNA sequence and analysis including novel gene identification, Nature, 440: 497-500.*
Nickel et al., 2008, An Empirical Test for Branch-Specific positive Selection, Genetics, 179: 2183-2193.*
Prufer et al., 2012, The bonobo genome compared with the chimpanzee and human genomes, Nature, 486(7404): 527-531.*
Schmutz et al., 2004, The DNA sequence and comparative analysis of human chromosome 5, Nature, 431: 268-274.*
Fathallah et al., 1993, Molecular cloning of a novel human hsp70 from a B cell line and its assignment to chromosome 5, The Journal of Immunology, 151: 810-813.*
Adavani et al., 1987, Multiple mRNA Species Code for the Catalytic Subunit of the cAMP-dependent Protein Kinase From LLC-PK1 Cells. Evidence for Two Forms of the Catalytic Subunit., Eur J Biochem, 167(2): abstract only.*
Grimwood et al., 2004, The DNA sequence and biology of human chromosome 19, Nature, 428: 529-535.*
Gregory et al., 2006, The DNA seqeunce and biological annotation of human chromosome 1, Nature, 441: 315-319.*
"International Application Serial No. PCT US2019 015210, Invitation to Pay Additional Fees and Partial Search Report dated Apr. 24, 2019", 2 pgs.
"International Application Serial No. PCT US2019 015210, International Search Report dated Jul. 23, 2019", 5 pgs.
"International Application Serial No. PCT US2019 015210, Written Opinion dated Jul. 23, 2019", 7 pgs.
Chada, "Apoptin studies illuminate intersection between lipidomics and tumor suppressors", Molecular Therapy, 15(1), (Jan. 2007), 7-9.
"International Application Serial No. PCT/US2019/015210, International Preliminary Report on Patentabiity dated Aug. 6, 2020", 9 pgs.

* cited by examiner

*Primary Examiner* — Amber D Steele
(74) *Attorney, Agent, or Firm* — Schwegman Lundberg & Woessner, P.A.

(57) ABSTRACT

Provided herein are compositions including peptide or nucleic acids encoding peptides and related methods for the treatment of angiogenic conditions such as cancer, vascular disorders such as cardiovascular disorders, and infectious disease.

14 Claims, 29 Drawing Sheets

Specification includes a Sequence Listing.

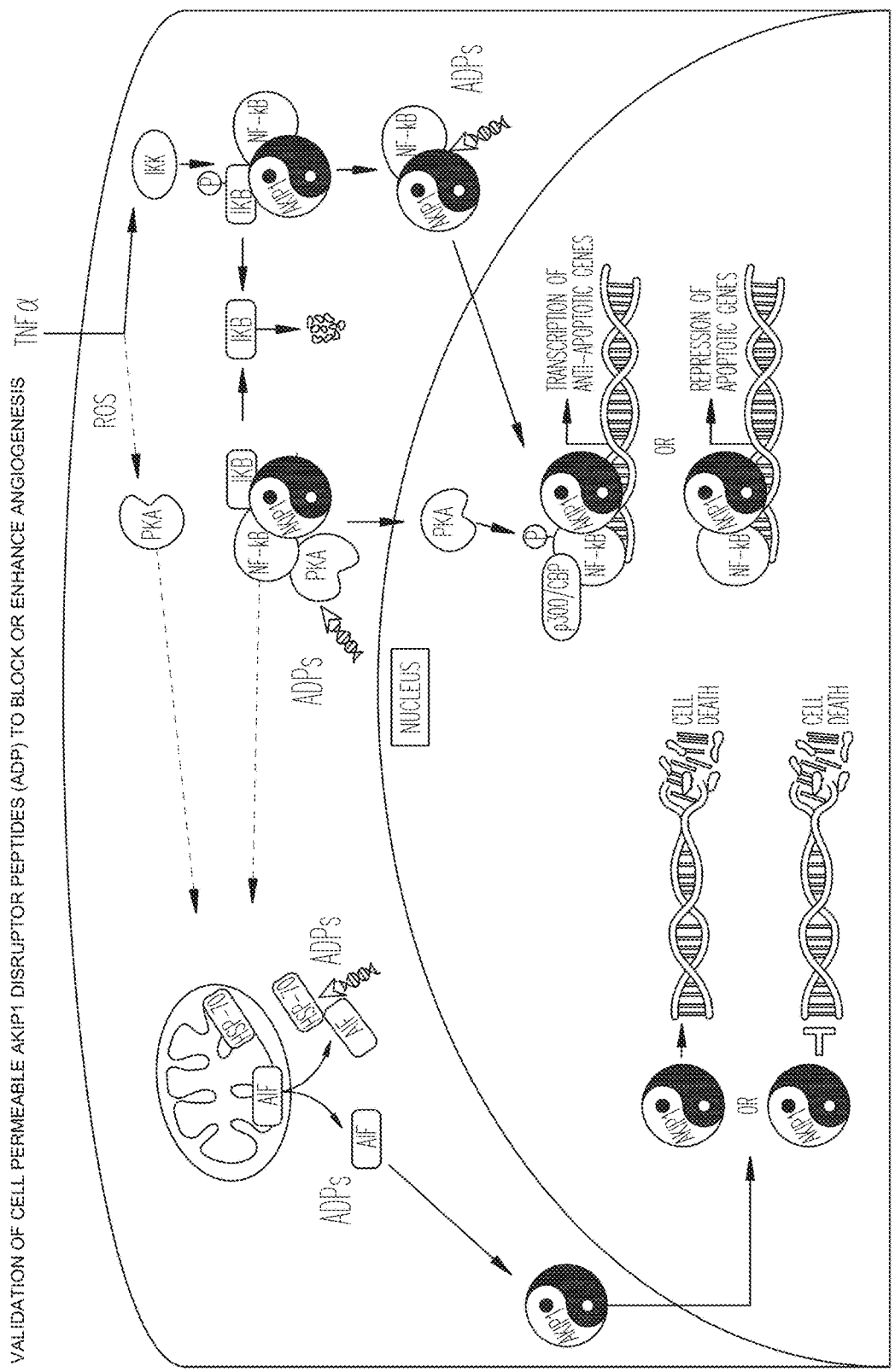

| | | | | | | |
|---|---|---|---|---|---|---|
| AKIP1a | MDNCLAAAAL | NGVDRRSLQR | SAKLALEVLE | RAKRRAVDWH | ALERPRGCMG | VLAREAPHLE |
| AKIP1b | MDNCLAAAAL | NGVDRRSLQR | SAKLALEVLE | RAKRRAVDWH | ALERPRGCMG | VLAREAPHLE |
| AKIP1c | MDNCLAAAAL | NGVDRRSLQR | SAKLALEVLE | RAKRRAVDWH | ALERPRGCMG | VLAREAPHLE |
| AKIP1d | MDNCLAAAAL | NGVDRRSLQR | SAKLALEVLE | RAKRRAVDWH | ALERPRGCMG | VLAREAPHLE |
| mAKIP1 | MEYCLAAAAL | NGVDRRSLQR | SARLGREVLE | RAKRRAVDWH | SPERSRGNVG | VLRQGPYQE |
| rAKIP1 | MEYCLAAAAL | NAVDPRRSLQR | SARLGREVLE | RAKRRAVDWH | SPERSRGCVG | VLYGQDPYQE |

| | | | | | | |
|---|---|---|---|---|---|---|
| AKIP1a | KQPAAGPQRV | LPGEREERPP | TLSASPRTMA | EMDYTSSQC | GKYTSSVPEE | GGATHVYRYH |
| AKIP1b | KQPAAGPQRV | LPGE------ | ---------- | ---------- | -KYTSSVPEE | GGATHVYRYH |
| AKIP1c | KQPAAGPQRV | LPGE------ | ---------- | ---------- | -KYTSSVPEE | GGATHVYRYH |
| AKIP1d | KQPAAGPQRV | LPGEREERPP | TLSASPRTMA | EMDYTSSQC | GKYTSSVPEE | GGATHVYRYH |
| mAKIP1 | RWSVPGSQRL | L-GEREERCP | TLSSSPGAMA | EMDYTSSQC | GKYILSMPEE | GGATHVYRYH |
| rAKIP1 | RWSVPGQSL | L-GEREERRP | TLSTSPRTMA | EMDYTSSQC | GKYILSTPEE | GGATHVYRYH |

| | | | | | | |
|---|---|---|---|---|---|---|
| AKIP1a | RGES-KLHMC | LDIGNGQ--R | KDRKKTSLGP | GGSYQISEHA | PEASQPAENI | SKDLYIEVYP |
| AKIP1b | RGES-KLHMC | LDIGNGQ--R | KDRKKTSLGP | GGSYQISEHA | PEASQPAENI | SKDLYIEVYP |
| AKIP1c | RGES-KLHMC | LDIGNGQ--- | ---------- | ---------- | ------AENI | SKDLYIEVYP |
| AKIP1d | RGES-KLHMC | LDIGNGQ--- | ---------- | ---------- | ------AENI | SKDLYIEVYP |
| mAKIP1 | RRKPFMHMY | SDTGHSQEQR | NCRGETSVGQ | ESIYQTSEHS | QESSWPTENI | SKDLYIEVYP |
| rAKIP1 | RRKPAEVHVC | SDSGHREAQR | NCRGETSVGP | GSIYQTSEHS | QESSWPIENI | SKDLYIEVYP |

| | | | |
|---|---|---|---|
| AKIP1a | GTYSVTVGSN | DLTKKTHVVA | VDSGQSVDLV FPV |
| AKIP1b | GTYSVTVGSN | DLTKKTHVVA | VDSGQSVDLV FPV |
| AKIP1c | GTYSVTVGSN | DLTKKTHVVA | VDSGQSVDLV FPV |
| AKIP1d | GTYSVTVGSN | DLTKKTHVVA | VDSGQSVDLV FPV |
| mAKIP1 | GTYSVTVGSS | ALSKKTHVVA | VDPGQSVDLV FPV |
| rAKIP1 | GTYSVTVGSN | DLTKKTHVVA | VDSGQSVDLV FPV |

Fig. 2B

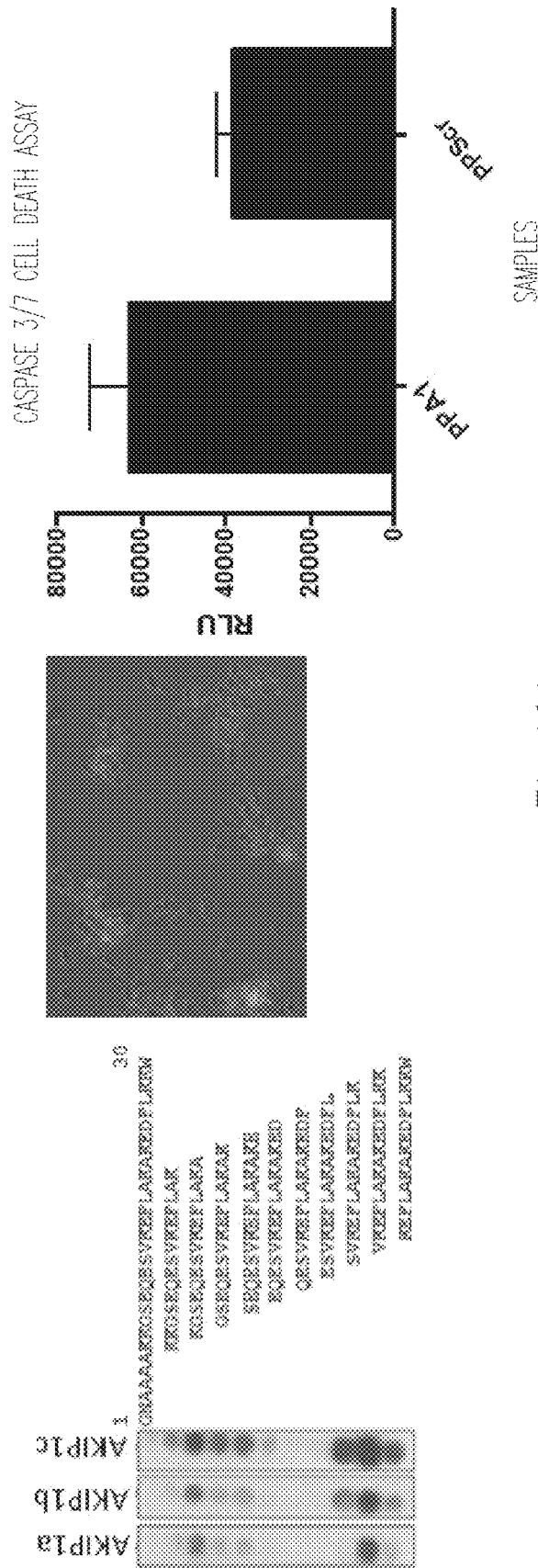

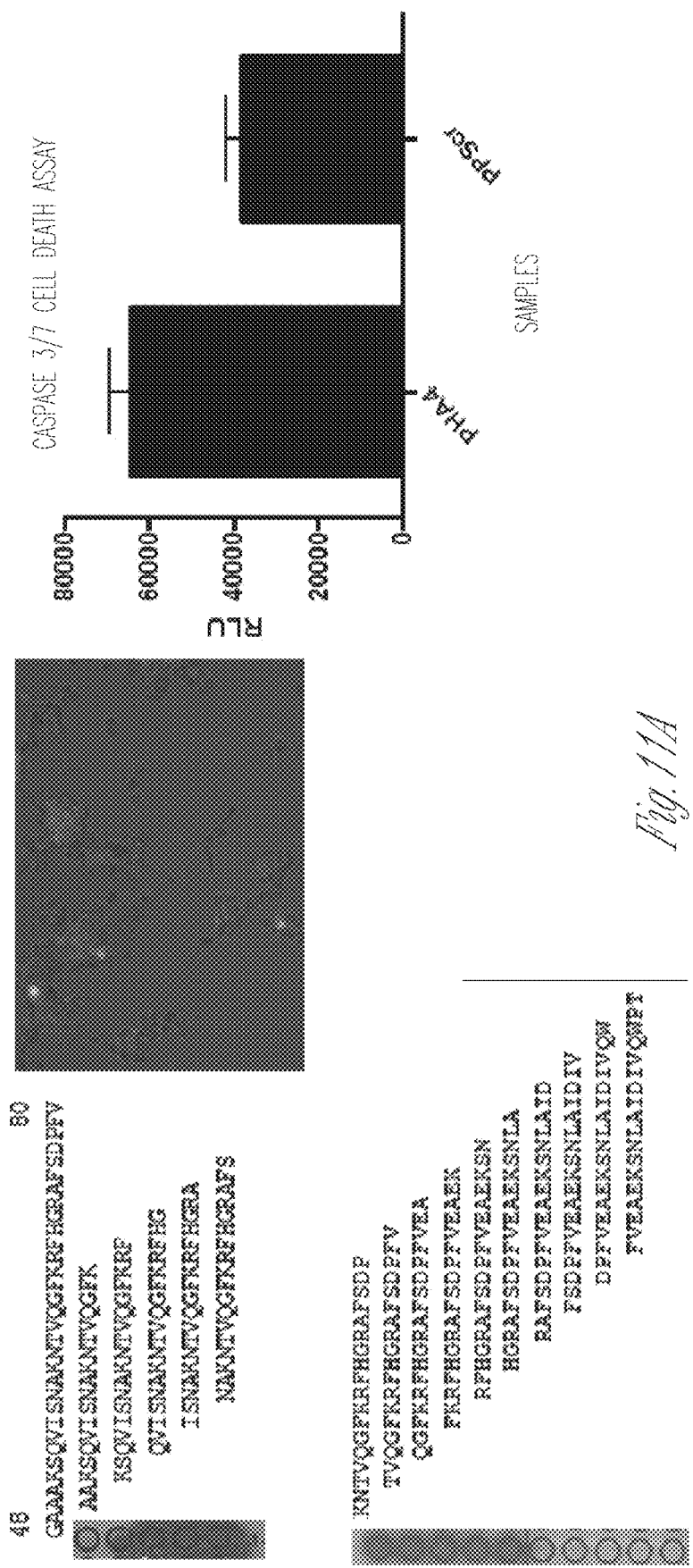

PHA5    Hsp-70 Pep5    PEPTIDE Hsp 70 THAT BINDS AKIP    MAKRGARSTAMQDKLEKERNDAKNAVEEYVYEMRDKLSGEYEKFVSEDDRNSFTLKLEDTENWL

TEV site

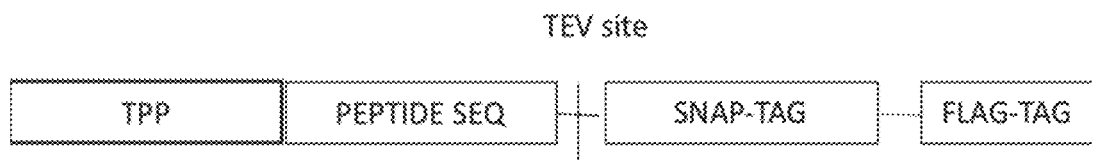

Figure 19

PEPTIDE6: NSTDPAVFTDLASVDNSEFQQLLNQGIPVAPHTTEPMLMEYPEAITRLV

```
            454                            484
            GNSTDPAVFTDLASVDNSEFQQLLNQGIPV
              PAVFTDLASVDNSEF
              AVFTDLASVDNSEFQ
               VFTDLASVDNSEFQQ
                FTDLASVDNSEFQQL
                 TDLASVDNSEFQQLL
                  DLASVDNSEFQQLLN
                   LASVDNSEFQQLLNQ
                    ASVDNSEFQQLLNQG
```

Figure 20A.

PEPTIDE9: KYYSSVPEEGGATHVYRYHRGESKLHM

```
     95                                136
     YTSSQCGKYYSSVPEEGGATHVYRYHRGESKLHMCLDIGNGQ
                  EGGATHVYRYHRGESKLH
                   GGATHVYRYHRGESKLHM
                    GATHVYRYHRGESKLHMC
                     ATHVYRYHRGESKLHMCL
                      THVYRYHRGESKLHMCLD
                       HVYRYHRGESKLHMCLDI
                        VYRYHRGESKLHMCLDIG
                         YRYHRGESKLHMCLDIGN
                          RYHRGESKLHMCLDIGNG
                           YHRGESKLHMCLDIGNGQ
```

Figure 20B.

PEPTIDES FOR ANGIOGENIC THERAPY

CROSS-REFERENCE TO RELATED APPLICATIONS

This application is a U.S. National Stage Filing under 35 U.S.C. 371 from International Application No. PCT/US2019/015210, filed on Jan. 25, 2019, which claims the benefit of the filing date of U.S. application No. 62/622,012, filed on Jan. 25, 2018, the disclosure of each of which is incorporated by reference herein in its entirety.

BACKGROUND

Angiogenesis and lymphanogensis, formation of new blood and lymph vessels, is an essential component in health. While physiological angiogenesis is needed for maintenance of normal tissue growth, remodeling, and regeneration, disease states co-opt this process resulting in dysregulated angiogenesis in a number of disorders including cancer, inflammatory, infectious and eye diseases as well as impaired cardiac and neuronal function (Carmeliet, 2005; Osherov et al., 2016).

In cancer, angiogenic processes are hijacked to feed the growing tumors with oxygen and nutrients (Kerbel, 2009; Achen et al., 2002). Therefore, anti-angiogenics in combination with chemotherapy have shown considerable promise. However, anti-angiogenics such as Avastin (anti-VEGF inhibitors) can induce various signaling pathways that result in drug resistance and recurrence of invasion and metastasis, thereby resulting in poor outcomes of overall survival (Jayson et al., 2016).

Glioblastoma MultiForme (GBM) is the most aggressive brain cancer, constituting 38% of primary tumors. The diverse nature of the tumor microenvironment with highly diffused invasive margins has rendered traditional methods of surgical resection followed by chemotherapy and radiation ineffective.

GBM has one of the most dysfunctional tumor vasculatures due to its unique angiogenic pathologies developed by the breakdown of intratumoral blood brain barrier.

In contrast to cancer, conditions such as myocardial infarction, peripheral vascular disease and neurodegenerative diseases have the feature of faulty and leaky vasculature due to attenuated angiogenesis, which can lead to organ and tissue failure particularly under ischemic injury. Proangiogenic therapies have proven intractable due to unfavorable pharmacokinetic profiles of angiogenic factors such as VEGF due to their inherent instability (De Rosa et al., 2018).

A-kinase-interacting protein 1 (AKIP1, aka BCA3) may be a potent oncogenic agent promoting angiogenesis and lymphanogenesis in a number of cancers such as breast, small cell lung, esophageal squamous and heptocellular carcinomas (Guo et al., 2017; Lin et al., 2015; Mo et al., 2016; Ma et al., 2018). AKIP1 was first identified as a protein highly expressed in breast and prostate cancers with little to no expression in normal breast and prostate tissues (Kitching et al., 2003).

AKIP1 is upregulated upon ischemia-reperfusion injury (i/R injury), increases in PKA signaling, improves cardiac function, and enhances mitochondrial protection upon ischemic stress (Sastri et al., 2013). AKIP1 also may play a role in infectious disease. AKIP1 interacts with HIV-protease (HIV-PR) and enhances p53 mediated apoptosis (Rumlova et al., 2014). Further, AKIP1 is incorporated into the HIV virions and may be essential for HIV replication (Rumlova et al., 2018). In a similar manner, AKIP1 is binding partner of Mason-Pfizer monkey virus (MPMV) protease (PR) and is incorporated into its virions (Rumlova et al., 2014). In addition, AKIP1 has been shown to interact with the Ring Finger domain of *Trypanosoma cruzi* (Hashimoto et al., 2010) as well as with Hepatitis B Virus Core protein (Lin et al., 2006). These studies show that AKIP1 may be involved in viral/parasitical pathogenicity.

AKIP1 scaffolds key signaling molecules including Apotosis inducing factor (AIF), Heat shock protein 70 (HSP-70), protein kinase A (PKA) and nuclear factor kappa-B (NF-kappaB) (Sastri et al., 2013; King et al., 2011; Sastri et al., 2005; Gao et al., 2008; Gao et al., 2010). In normal cells, there is an interplay of these molecules in different signaling pathways leading to cell growth and differentiation. But under pathophysiological conditions, proteins such as NF-kappaB and PKA have seminal roles in tumor development, progression, metastasis, and have been implicated in both intrinsic and acquired chemotherapy resistance (Liu et al., 2014; Perez Pinero et al., 2012; Hanahan et al., 3000; Nakagawa et al., 2015; Prasad et al., 2009).

AKIP1 is a relatively small protein (between 17-23 kDa) and in humans, there are three major splice variants of AKIP1: AKIP1a, AKIP1b, which lacks the third exon, and the predominant AKIP1c, which lacks the third and fifth exon (AKIP1c). A recent study identified another uncharacterized splice variant that lacks only the fifth exon (Zhang et al., 2014), which variant is referred to as AKIP1d herein.

SUMMARY

AKIP1 is involved in angiogenesis via signaling proteins such as PKAc, AIF, HSP-70 and p65 subunit of NF-κB. Additionally, AKIP1 isoforms show differential binding to these proteins. As disclosed herein, isoform specific-expression of AKIP1 may be involved in angiogenesis, e.g., as a driver of tumor recalcitrance and metastasis in cancer. Peptides were identified, e.g., peptides of AKIP1, PKAc, HSP-70 and p65, including peptides having SEQ ID Nos. 1-25, that showed angiogenic and/or apoptotic activity, e.g., as a result of binding to AKIP1 or AKIP interacting proteins, thus disrupting AKIP1 mediated signaling. Thus, peptide and peptide mimetics derived from AKIP1 and its interacting proteins including but not limited to PKAc, RelA (p65 NF-κB), AIF and HSP70 may be employed prophylactically or therapeutically. For example, peptides with anti-angiogenic or apoptotic activity may be useful in angiogenic therapies including treating cancer. Thus, the present disclosure provides peptides that inhibit the growth of tumors, e.g., AKIP1-positive tumors. For instance, specific isoforms of AKIP1 involved in oncogenesis were identified and these or factors that interact with AKIP1 may be used to prevent, inhibit or treat diseases, e.g., angiogenesis and lymphangiogenesis diseases, including ischemic heart diseases, and cancer. The peptides may be tested in various CRISPR derived AKIP1 isoform specific cell lines for their efficacy. Stable cell lines of the peptides may be used in xenograft models. Peptides with angiogenic or anti-apoptotic activity may be useful in other diseases or disorders.

The disclosure provides a pharmaceutical composition comprising an effective amount of any one of SEQ ID Nos. 1-25, or a fragment thereof that alters angiogenesis or apoptosis, or a peptide having the length of and at least 85% amino acid sequence identity to any one of SEQ ID Nos. 1-25. In one embodiment, the peptide is fused to another peptide, thereby forming a fusion peptide. In one embodiment, the fusion peptide is a N-terminal or a C-terminal fusion. In one embodiment, the fusion peptide is a N-terminal and a C-terminal fusion. In one embodiment, the other peptide is a cell or tissue targeting peptide. In one embodiment, the composition comprises a pharmaceutically acceptable carrier. In one embodiment, the composition is in a liposome. In one embodiment, the composition of is in a nanoparticle. In one embodiment, the peptide is PEGylated. In one embodiment, the peptide has 5, 6, 7, 10, 12, or 15 fewer amino acid residues relative to SEQ ID Nos. 1-25. In one embodiment, the peptide has 4 or fewer amino acid residues relative to SEQ ID Nos. 1-25. In one embodiment, the peptide has at least 88%, 90%, 95%, 96%, 97%, 98% or 99% amino acid sequence identity to one of SEQ ID Nos. 1-25.

The disclosure further provides a pharmaceutical composition comprising an effective amount of, in one embodiment, PEPTIDE1 (SEQ ID NO:1), PEPTIDE2 (SEQ ID NO:2), PEPTIDE3 (SEQ ID NO:3), PEPTIDE4 (SEQ ID NO:4), PEPTIDE5 (SEQ ID NO:5), PEPTIDE7 (SEQ ID NO:7), PEPTIDE8 (SEQ ID NO:8), PEPTIDE9 (SEQ ID NO:9), PEPTIDE10 (SEQ ID NO:10), PEPTIDE11 (SEQ ID NO:11), PEPTIDE13 (SEQ ID NO:13), PEPTIDE14 (SEQ ID NO:14), PEPTIDE15 (SEQ ID NO:15), PEPTIDE16 (SEQ iD NO:16), PEPTIDE17 (SEQ ID NO:17), PEPTIDE18 (SEQ ID NO:18), or a fragment thereof that induces apoptosis or is anti-angiogenic, or a peptide having the length of and at least 85% amino acid sequence identity to the sequence of PEPTIDE1, PEPTIDE2, PEPTIDE3, PEPTIDE4, PEPTIDE5, PEPTIDE7, PEPTIDE8, PEPTIDE9, PEPTIDE10, PEPTIDE11, PEPTIDE13, PEPTIDE14, PEPTIDE15, PEPTIDE16, PEPTIDE17, PEPTIDE18, or a fragment thereof that induces apoptosis or is anti-angiogenic, or any combination hereof. In one embodiment, the peptide is fused to another peptide, thereby forming a fusion peptide. In one embodiment, the fusion peptide is a N-terminal or a C-terminal fusion. In one embodiment, the fusion peptide is a N-terminal and a C-terminal fusion. In one embodiment, the other peptide is a cell or tissue targeting peptide. In one embodiment, the composition comprises a pharmaceutically acceptable carrier. In one embodiment, the composition is in a liposome. In one embodiment, the composition of is in a nanoparticle. In one embodiment, the peptide is PEGylated. In one embodiment, the peptide has 5, 6, 7, 10, 12, or 15 fewer amino acid residues relative to SEQ ID Nos. 1-5, 7-11, or 13-18. In one embodiment, the peptide has 4 or fewer amino acid residues relative to SEQ ID Nos. 1-5, 7-11, or 13-18. In one embodiment, the peptide has at least 88%, 90%, 95%, 96%, 97%, 98% or 99% amino acid sequence identity to one of SEQ ID Nos. 1-5, 7-11, or 13-18.

Also provided is a pharmaceutical composition comprising an effective amount of PEPTIDE4 (SEQ ID NO:4), PEPTIDE6 (SEQ ID NO:6), PEPTIDE8 (SEQ ID NO:8), PEPTIDE10 (SEQ ID NO:10), PEPTIDE11 (SEQ ID NO:11), PEPTIDE12 (SEQ ID NO:12), PEPTIDE16 (SEQ ID NO:16), or a fragment thereof that induces angiogenesis or enhances cell survival, or a peptide having the length of and at least 85% amino acid sequence identity to the sequence of PEPTIDE4, PEPTIDE8, PEPTIDE10, PEPTIDE11 or PEPTIDE16, or a fragment thereof that induces angiogenesis or enhances cell survival. In one embodiment, the peptide is fused to another peptide, thereby forming a fusion peptide. In one embodiment, the fusion peptide is a N-terminal or a C-terminal fusion. In one embodiment, the fusion peptide is a N-terminal and a C-terminal fusion. In one embodiment, the other peptide is a cell or tissue targeting peptide. In one embodiment, the composition comprises a pharmaceutically acceptable carrier. In one embodiment, the composition is in a liposome. In one embodiment, the composition of is in a nanoparticle. In one embodiment, the peptide is PEGylated. In one embodiment, the peptide has 5, 6, 7, 10, 12, or 15 fewer amino acid residues relative to SEQ ID Nos. 2, 4, 6, 8, 10-12, or 16. In one embodiment, the peptide has 4 or fewer amino acid residues relative to SEQ ID Nos. 2, 4, 6, 8, 10-12, or 16. In one embodiment, the peptide has at least 88%, 90%, 95%, 96%, 97%, 98% or 99% amino acid sequence identity to one of SEQ ID Nos. 2, 4, 6, 8, 10-12, or 16.

The peptides may be stabilized for drug delivery, for example, using modifications including but not limited to synthesis as PEGylated peptides, retro-inverso peptides and stapled peptides or may be delivered as cargos on lentiviruses, adenoviruses and the like as disclosed below.

Also provided is a viral vector comprising nucleic acid comprising a nucleotide sequence encoding any one of SEQ ID Nos. 1-25, or a fragment thereof that alters angiogenesis or apoptosis, or a peptide having the length of and at least 85% amino acid sequence identity to any one of SEQ ID Nos. 1-25, or a fragment thereof that alters angiogenesis or apoptosis. In one embodiment, the vector is a lentivirus vector or an adenovirus vector.

A recombinant virus comprising nucleic acid comprising a nucleotide sequence encoding any one of SEQ ID Nos. 1-25, or a fragment thereof that alters angiogenesis or apoptosis, or a peptide having the length of and at least 85% amino acid sequence identity to any one of SEQ ID Nos. 1-25, or a fragment thereof that alters angiogenesis or apoptosis, is provided. In one embodiment, the virus is a lentivirus or an adenovirus.

The disclosure provides a method to prevent, inhibit or treat aberrant angiogenesis in a mammal, comprising: administering to a mammal in need thereof an effective amount of the composition, the vector, or the virus described herein. In one embodiment, the mammal has cancer. In one embodiment, the mammal has an infectious disease, neutropenia, ocular neovascularization, retinal vascular disease, neovascular glaucoma, meningitis, encephalitis, sleep apnea, obesity, gestational diabetes mellitus, proliferative diabetic retinopathy, diabetic macular edema, familial hypercholesterolemia, a skin or subcutaneous disorder such as cutaneous inflammation, psorisis, phototoxicity, chronic skin inflammation, atopic dermatitis, eczema, or polymyositisidermatomyositis, a chronic inflammatory disease such as inflammatory bowel disease, rheumatoid arthritis, osteoarthritis, Crohn's disease, Lyme disease, multiple sclerosis, Type 1 diabetes, psoriatic arthritis, restless legs syndrome (RLS), fibromyalgia, dermatitis herpetiformis, Sjögren's syndrome, systemic lupus erythematosus, or gout, a respiratory disease such as asthma, chronic obstructive pulmonary disease (COPD), or atypical lymphoid disorders, an inflammatory disease of the genitourinary system disease such as endometriosis, an inflammatory disease of the digestive system, such as liver fibrosis, a neonatal or perinatal disease such as retinopathy of prematurity, infant respiratory distress syndrome, cyanosis, neonatal conjunctivitis, intraventricular hemorrhage, Coat's disease, childhood Interstitial lung disease, Fifth disease, hand, foot, and mouth disease, croup, scarlet fever, impetigo, Kawasaki Disease, Reye's Syndrome, diphtheria, an age-related disease such as age-related macular degeneration, or frontotemporal dementias like Pick disease, Gorham-Stout Disease, adrenoleukodystrophy, abetalipoproteinernia arthrogryposis, adrenomyeloneuropathy, antisynthetase syndrome, ancylostomiasis, Addison's Disease, amyloidosis, birdshot chorioretinopathy, malignant peripheral nerve sheath tumors, Moyamoya, sarcoidosis, systemic capillary leak syndrome, or plasma cell dyscrasia. In one embodiment, the mammal is a human.

A method to decrease apoptosis in a mammal, comprising: administering to a mammal in need thereof an effective amount of the composition, the vector, or the virus described herein is provided. In one embodiment, the mammal has a vascular or cardiovascular disorder. In one embodiment, the mammal has a genitourinary system disease including male infertility or erectile dysfunction, a disease of the digestive system such as nonalcoholic steatohepatitis, a newborn or prenatal condition such as fetal hypoxia, respiratory distress syndrome, bronchopulmonary dysplasia, sudden infant death syndrome (SIDS), perinatal Asphyxia, necrotizing enterocolitis, patent ductus arteriosus, or erythroblastosis (blue baby syndrome), an age-related disease such as Parkinson's, Presbycusis and age-related hearing loss, osteoporosis, vascular dementia, Lewy Body dementia, or ataxia, common variable immunodeficiency, neonatal respiratory distress syndrome, preeclampsia or a congenital circulatory abnormality (e.g., Tetralogy of Fallot), In one embodiment, the mammal is a human.

In one embodiment, pro-angiogenic peptides are useful in treating certain anti-angiogenic cardiovascular diseases, e.g., CAD, and anti-angiogenic peptides are useful in treating pro-angiogenic cardiovascular diseases such as neonatal intraventricular hemorrhage.

Also provided is a mammalian host cell, the genome of which is augmented by a vector comprising nucleic acid comprising a nucleotide sequence encoding a peptide having one of SEQ ID Nos. 1-25, or a fragment thereof with apoptotic or angiogenic activity, or a peptide having the length of and at least 85% amino acid sequence identity to one of SEQ ID Nos. 1-25, or a fragment thereof with apoptotic or angiogenic activity.

BRIEF DESCRIPTION OF THE FIGURES

FIG. 1. Overview of AKP1 in cancer. AKIP1 is involved in various signaling pathways both at the nucleus and at the mitochondria. AKIP disrupting peptides (ADPs) could disrupt the various signaling molecules/complexes (such as PKA-NF-κB, AIF, HSP-70 etc).

FIGS. 2A-B. The various splice variants of AKIP1 and its sequences. A) Schematic of variants, B) The protein accession numbers for the variants are as follows AKIP1a: NP_001193575.1, AKIP1b: NP 001193575.1, AKIP1c: NP 001193576.1, and AKIP1d: NP_001193577.1 (SEQ ID Nos. 60-63), aligned with human and rat AKIP (SEQ ID Nos. 64-65), which sequences are incorporated by reference herein.

FIGS. 10A-C show the sequences mapped, peptide blots, imaging to show expression and cell death assays for these three peptides. A) PPA-1 (PEPTIDE23) (SEQ ID NO:23), B) PPA4 (PEPTIDE19) (SEQ ID NO:19), C) PPA10 (PEPTIDE16 including FF at C-terminus) (SEQ ID NO:16).

FIGS. 11A-B show the sequences mapped, peptide blots, imaging to show expression and cell death assays for these HSP-70 peptides. A) PHA4 (PEPTIDE5) (SEQ IDNO:5), B) PHA5 (PEPTIDE13 plus C-terminal L) (SEQ ID NO:13).

FIG. 19 shows the general design of with a cell penetrating peptide (TPP: tumor penetrating peptide (LinTT1) (Sharma et al., 2017); SNAP tag and FLAG tag attached to C-terminus to visualize the peptides in cells. A TEV site was engineered between the peptide sequence and SNAP tag.

FIGS. 20A-B shows blots for peptides related to PEPTIDE6 (A) (SEQ ID Nos. 36-45) and PEPTIDE9 (B) (SEQ ID Nos. 46-57).

DETAILED DESCRIPTION

Definitions

Figure 2A:
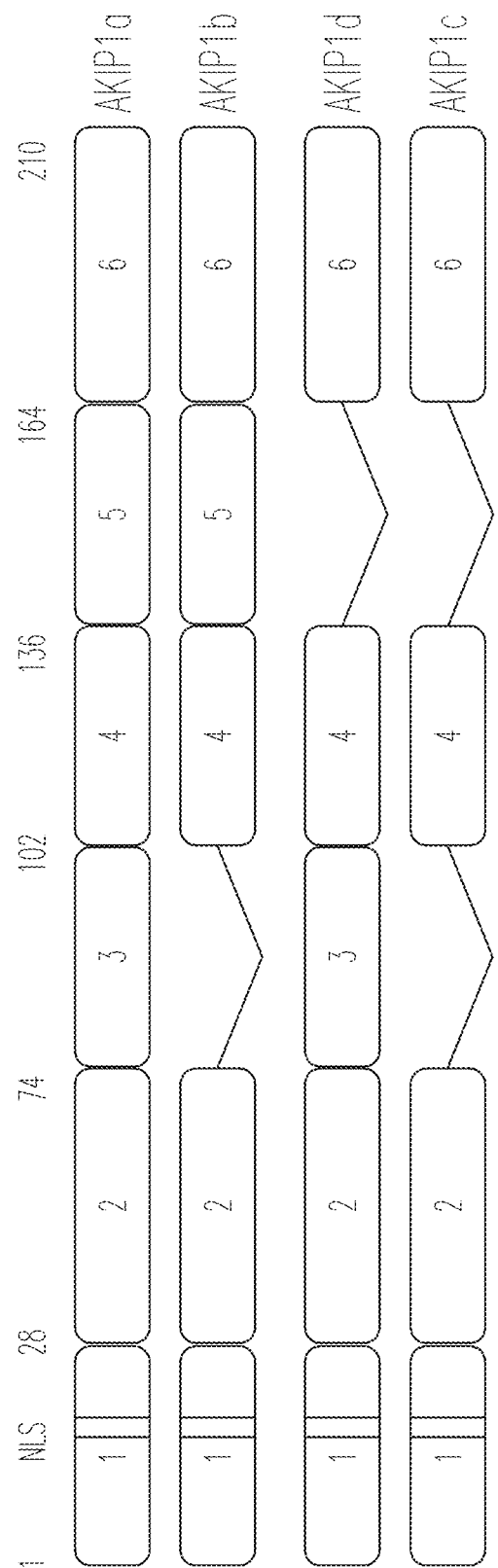
Figure 3B:
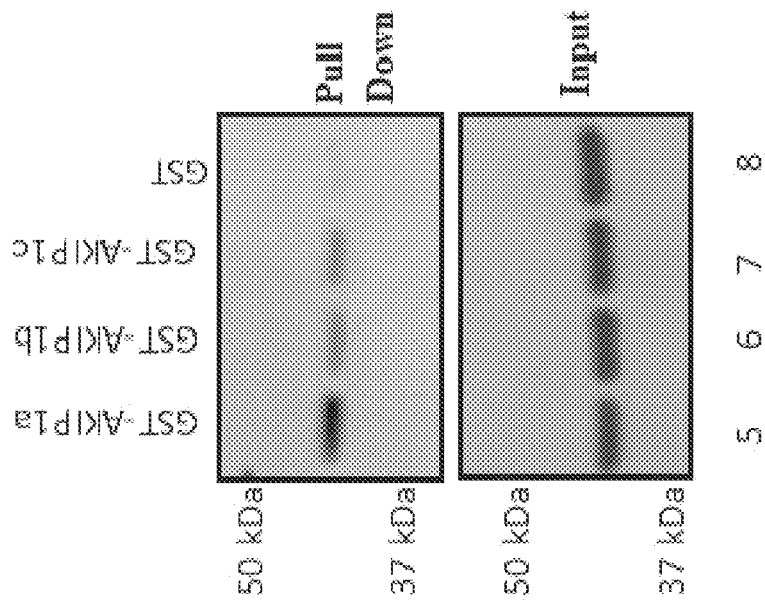
FIGS. 3A-D. AKIP1 binds to PKAc, AIF, HSP-70 and p^% of NF-kB. GST pull downs of the various isoforms. Panel 2 shows binding to PKAc. Panel 3 shows binding to AIF and HSP-70 and Panel 4 shows binding to p65 of NF-κB.
Figure 3A:
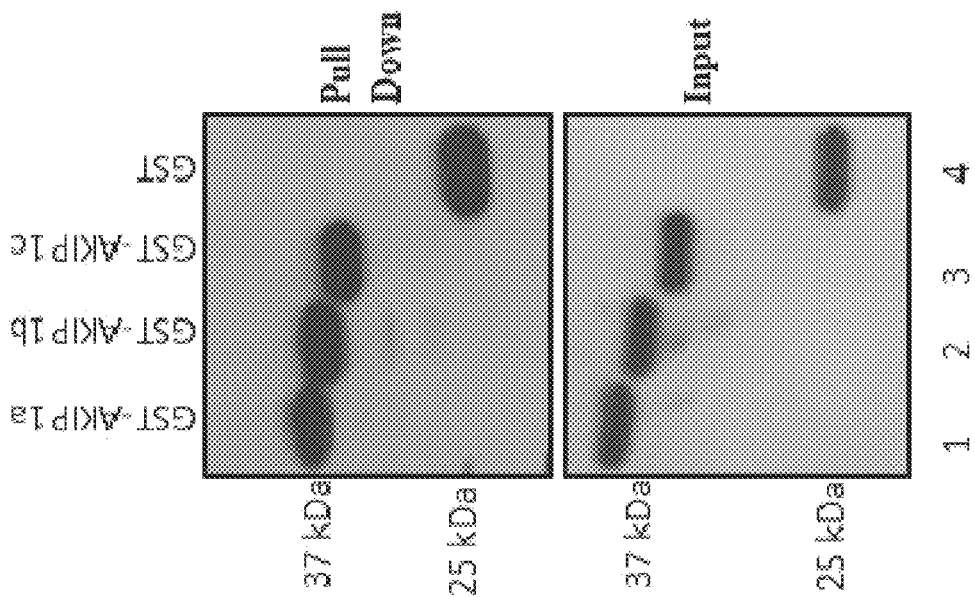
Figure 3C:
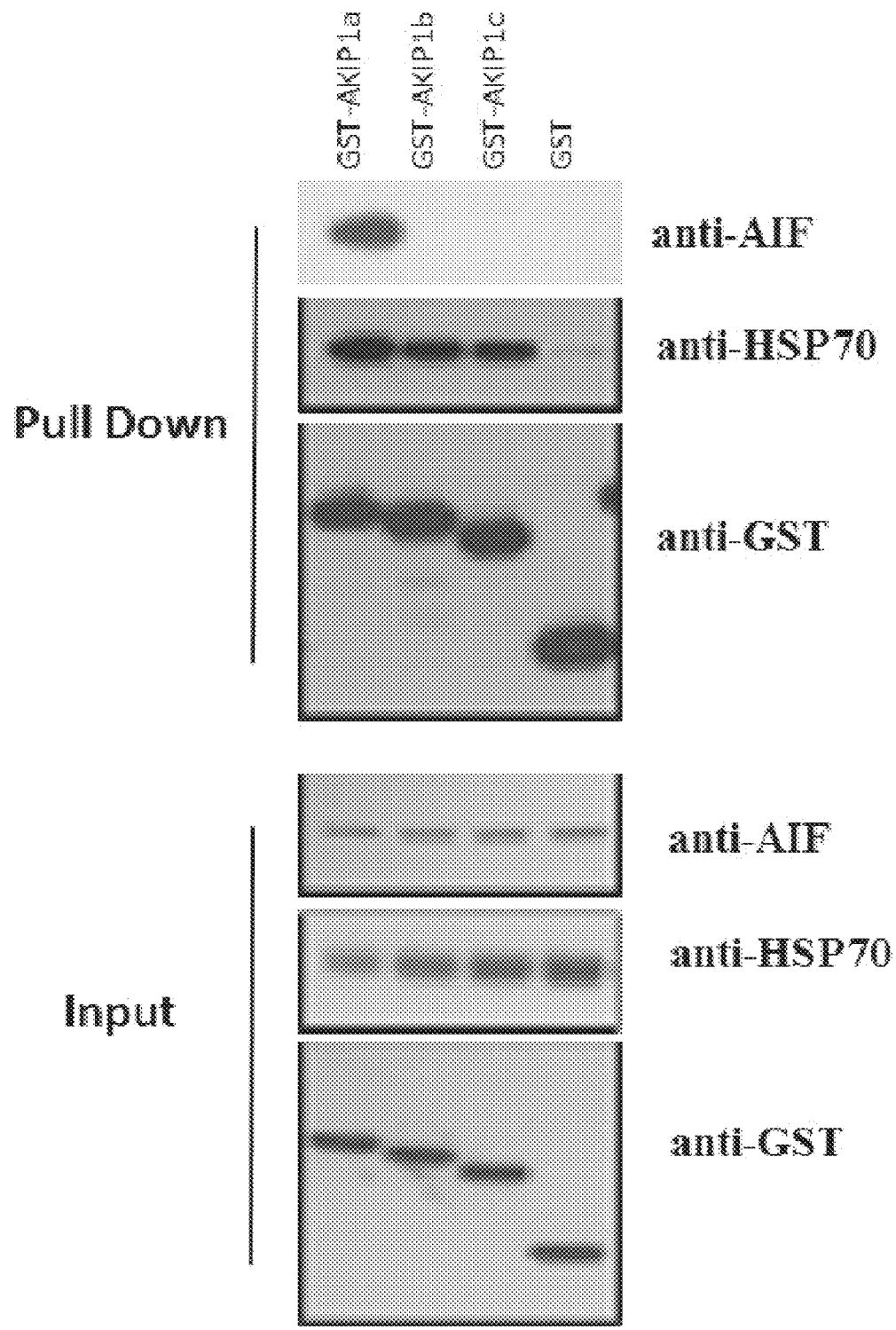
Figure 3D:
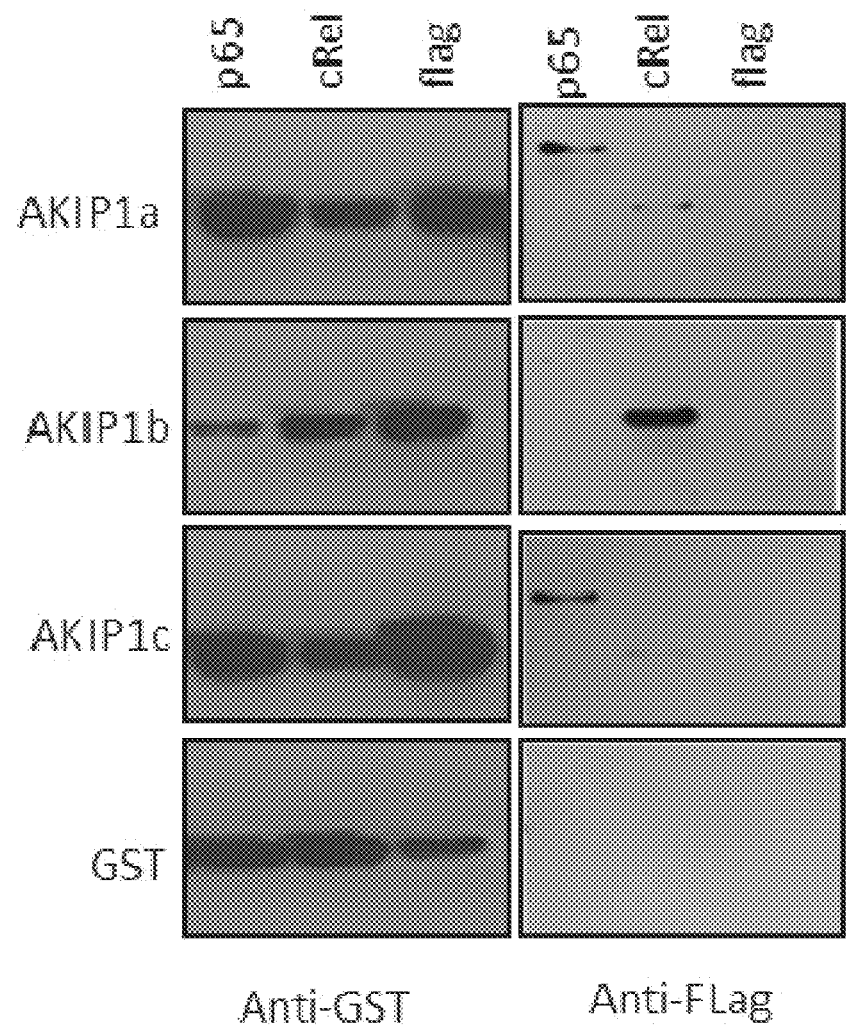
Figure 4A:
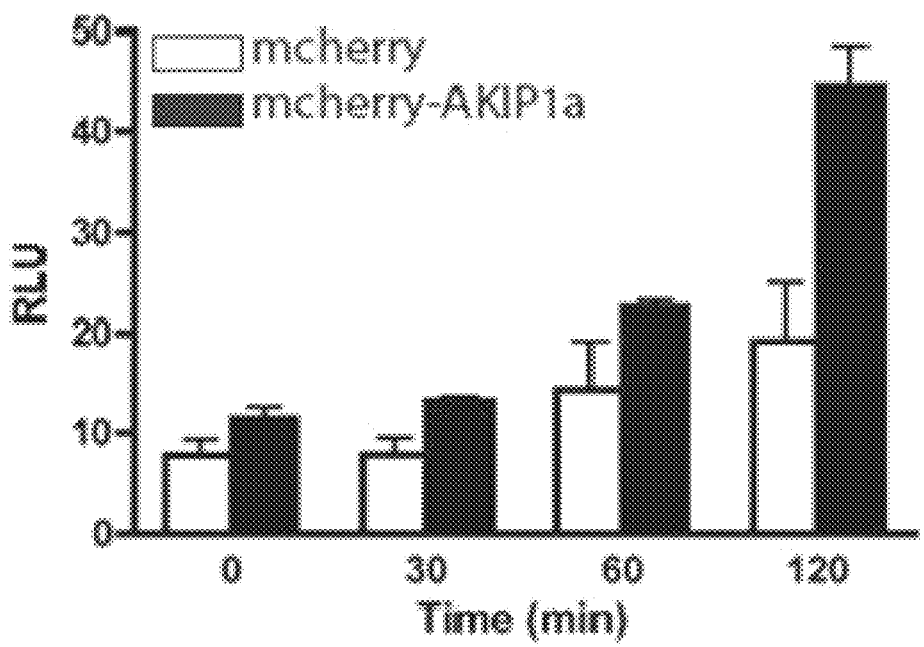
FIGS. 4A-C. AKIP1 shows differential activation of PKAc and AKIP1c is constitutively active.
Figure 4B:
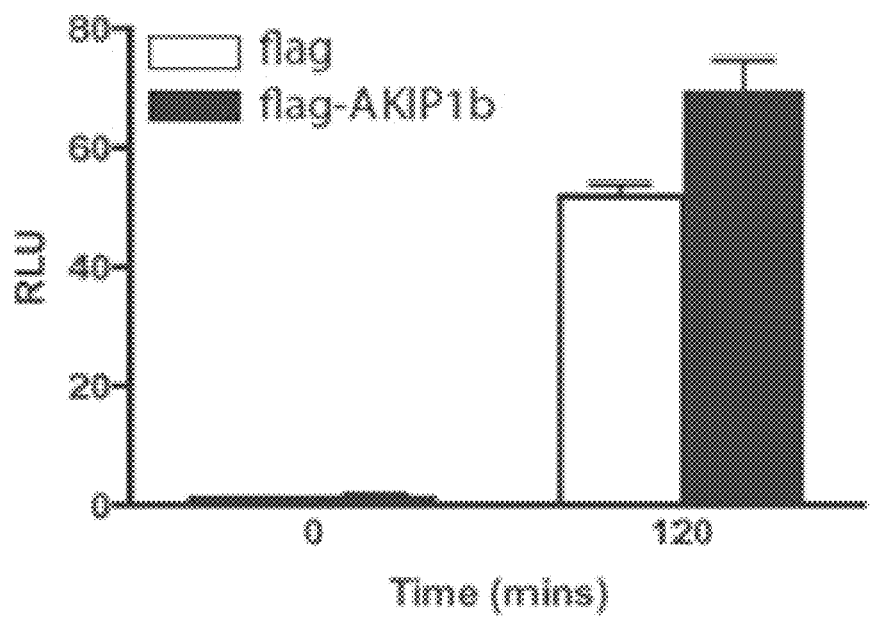
Figure 4C:
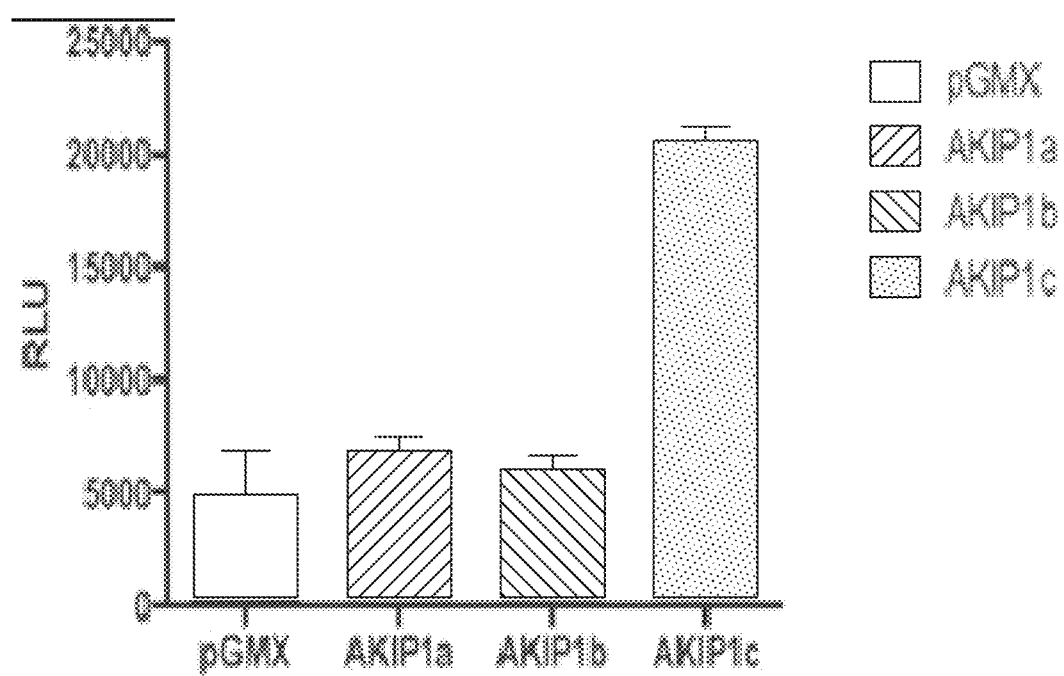
Figure 5:
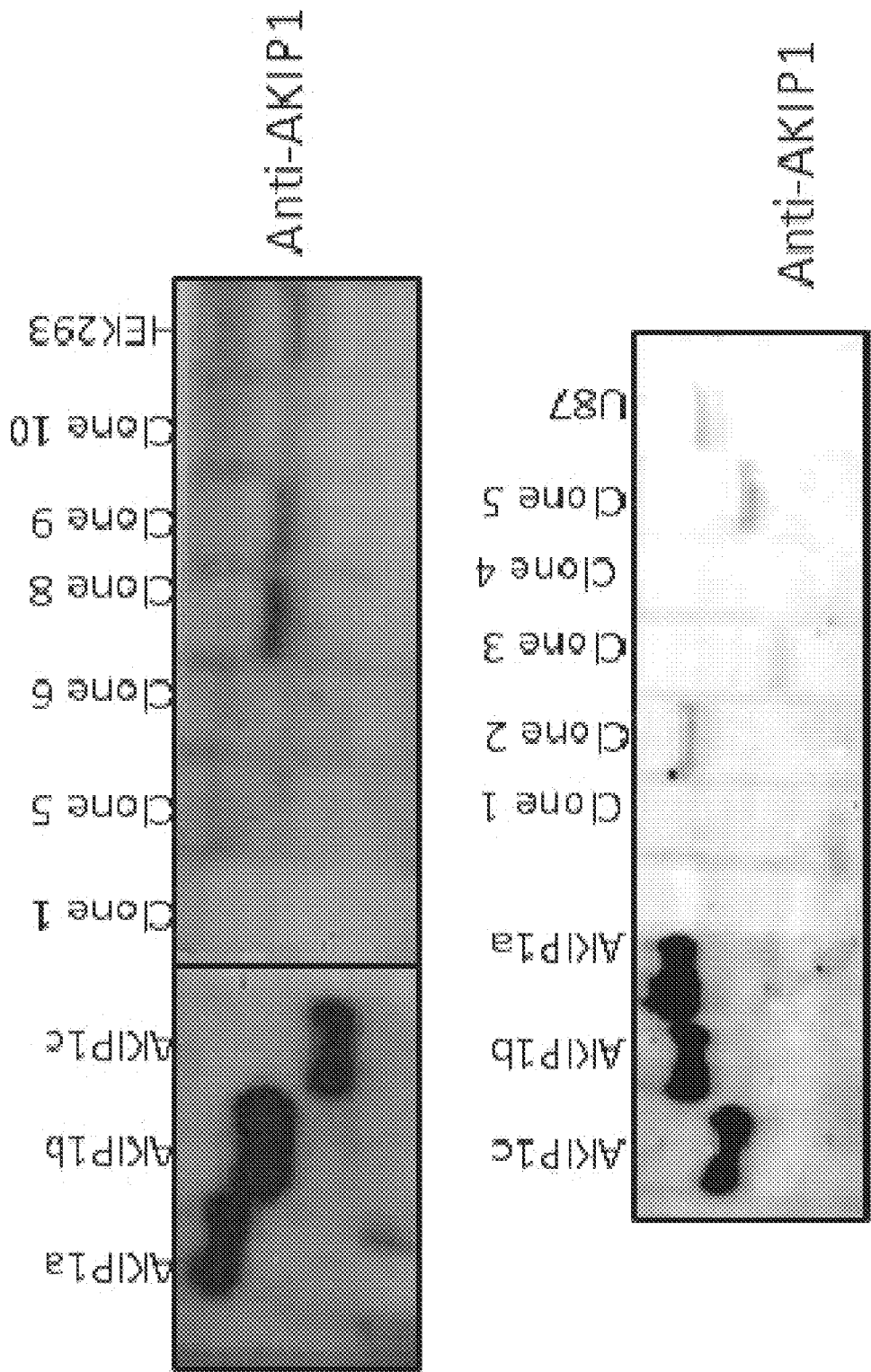
FIG. 5. Generation of HEK-293 and U87 MG glioblastoma derived cell line CRISPR AKIP1 Knockout cell lines.
Figure 6:
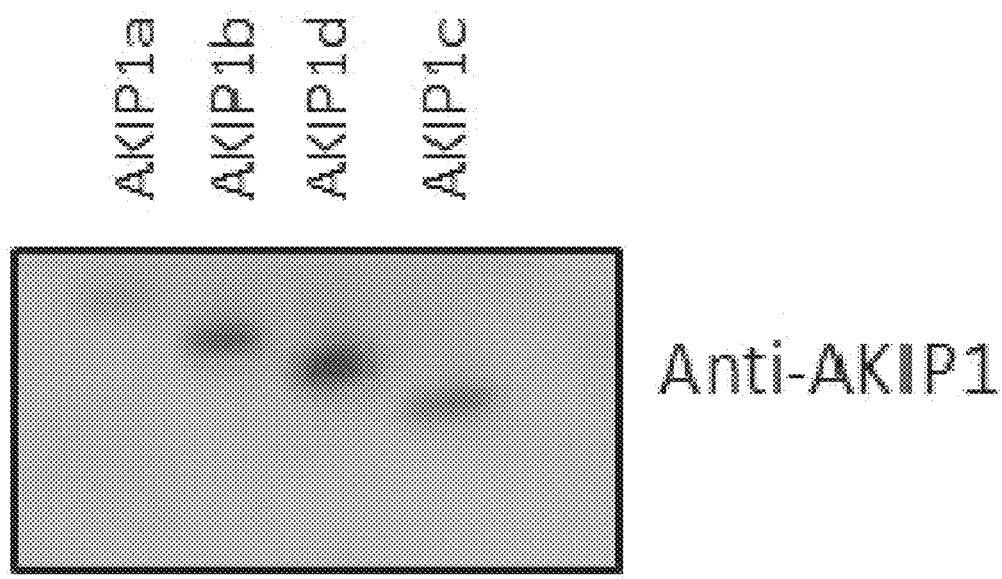
FIG. 6. U87 MG was then used to generate CRISPR knockout and isoform specific Knock-in lines.
Figure 7A:
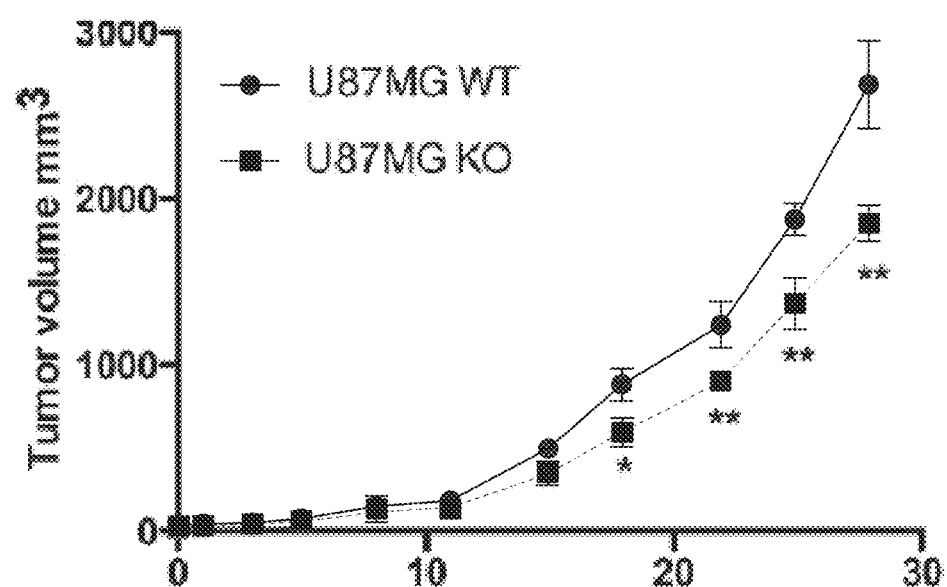
FIGS. 7A-C. Xenograft models of the CRISPR based Knock out cell lines of AKIP1. KO of AKIP1 causes tumor regression FIGS. 8A-C. Xenograft models of the CRISPR based Knock out and isoform specific cell lines of AKIP1. Reintroduction of the splice variant AKIP1a restores tumorgenesis. 2.7 denotes the KO while 906 denotes AKIP1a, 907 denotes AKIP1b, 908 denotes AKIP1d and 909 denotes AKIP1c. A) Xenograft sizes. B) Tumor volume over time. C) Schematic of isoforms.
Figure 7B:
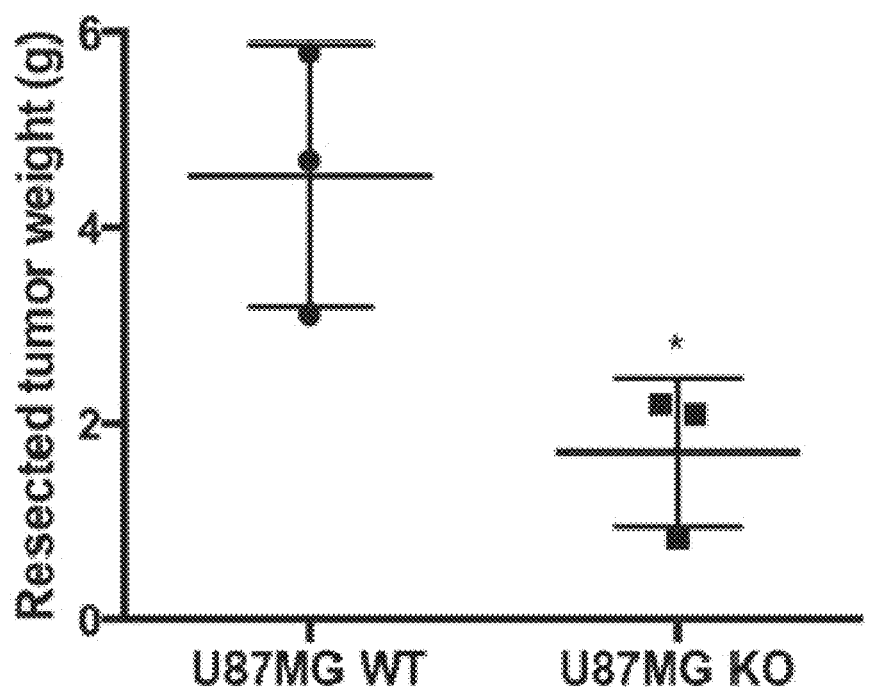
Figure 7C:
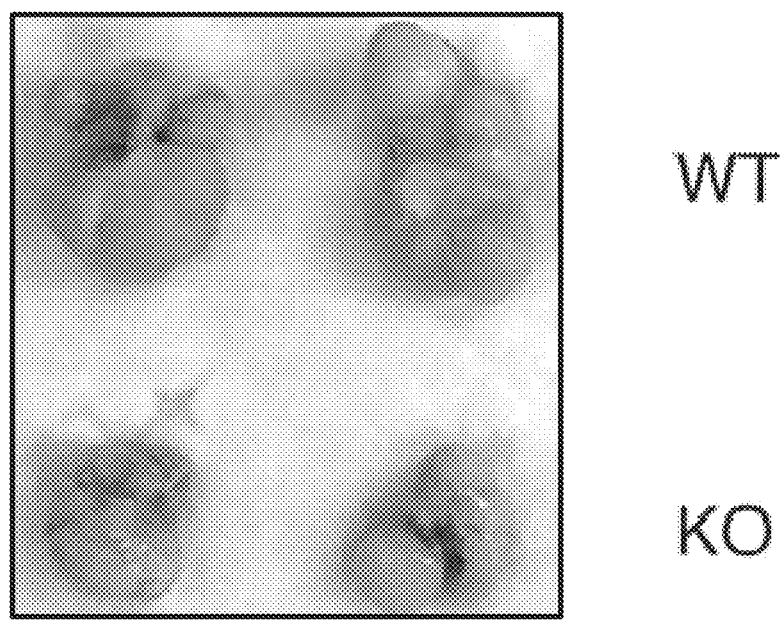
Figure 8A:
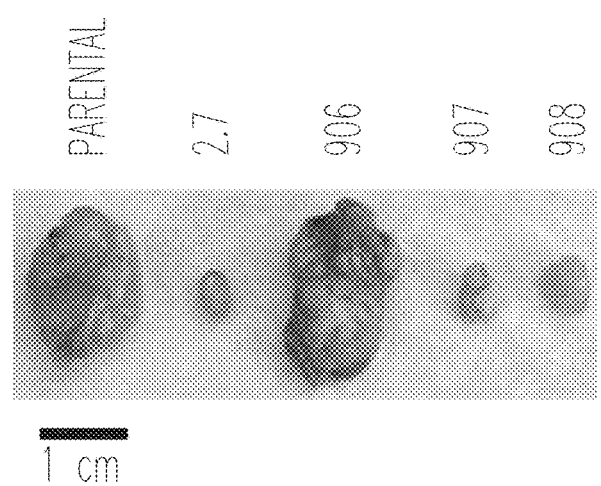
Figure 8B:
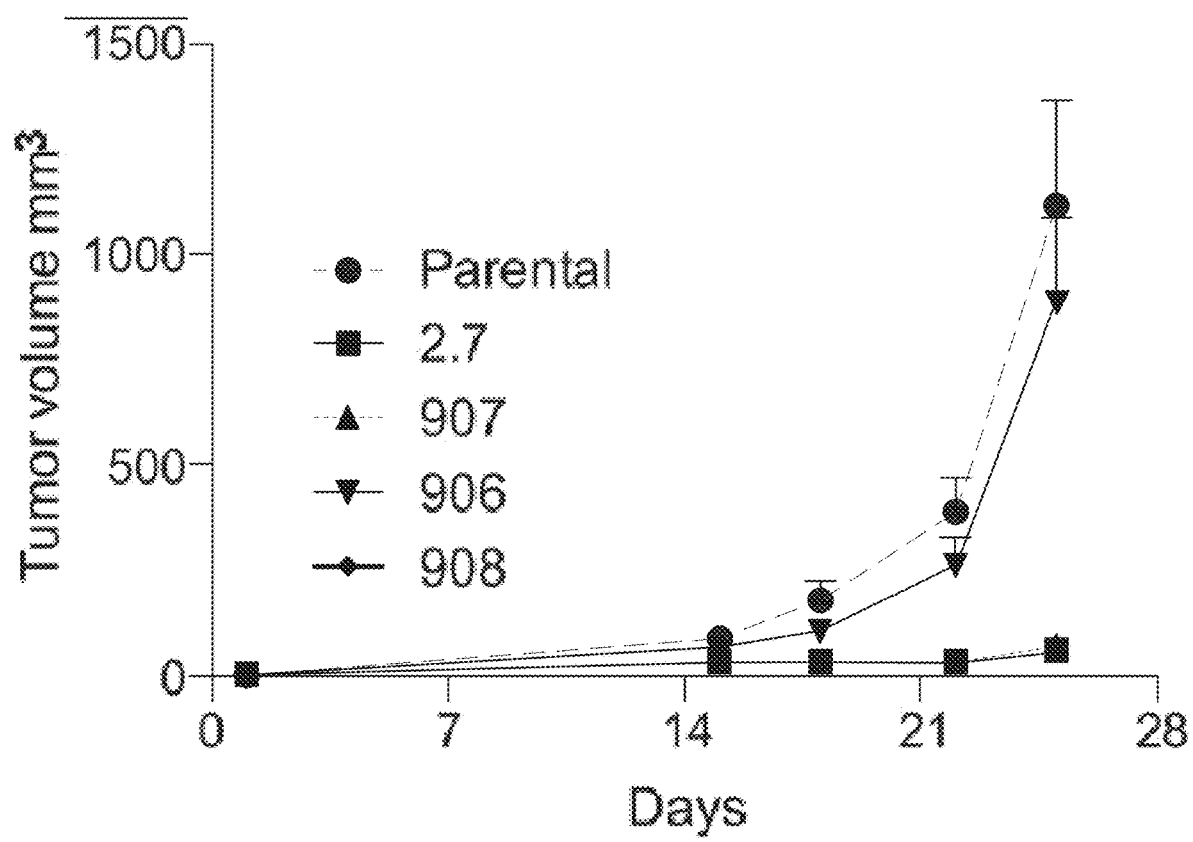
Figure 8C:
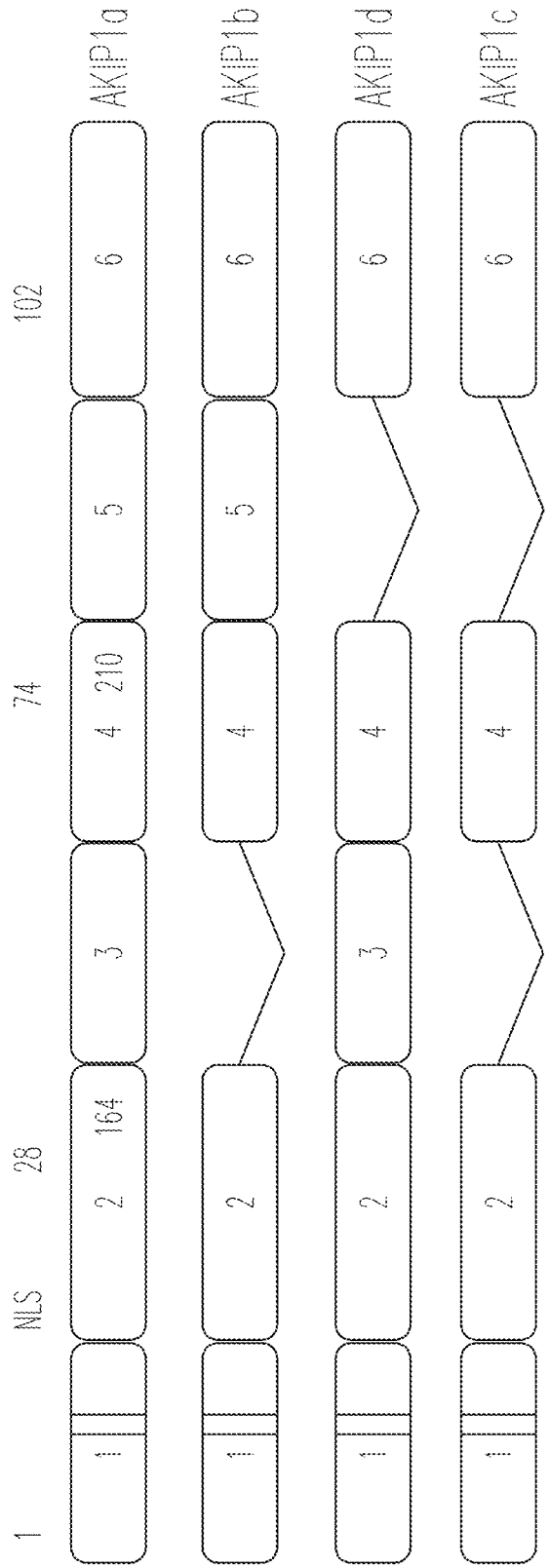

A "vector" refers to a macromolecule or association of macromolecules that comprises or associates with a polynucleotide, and which can be used to mediate delivery of the polynucleotide to a cell, either in vitro or in vivo. Illustrative vectors include, for example, plasmids, viral vectors, liposomes and other gene delivery vehicles. The polynucleotide to be delivered, sometimes referred to as a "target polynucleotide" or "transgene," may comprise a coding sequence of interest in gene therapy (such as a gene encoding a protein of therapeutic interest), a coding sequence of interest in vaccine development (such as a polynucleotide expressing a protein, polypeptide or peptide suitable for eliciting an immune response in a mammal), and/or a selectable or detectable marker.

"Transduction," "transfection," "transformation" or "transducing" as used herein, are terms referring to a process for the introduction of an exogenous polynucleotide into a host cell leading to expression of the polynucleotide, e.g., the transgene in the cell, and includes the use of recombinant virus to introduce the exogenous polynucleotide to the host cell. Transduction, transfection or transformation of a polynucleotide in a cell may be determined by methods well known to the art including, but not limited to, protein expression (including steady state levels), e.g., by ELISA, flow cytometry and Western blot, measurement of DNA and RNA by hybridization assays, e.g., Northern blots, Southern blots and gel shift mobility assays. Methods used for the introduction of the exogenous polynucleotide include well-known techniques such as viral infection or transfection, lipofection, transformation and electroporation, as well as other non-viral gene delivery techniques. The introduced polynucleotide may be stably or transiently maintained in the host cell.

"Gene delivery" refers to the introduction of an exogenous polynucleotide into a cell for gene transfer, and may encompass targeting, binding, uptake, transport, localization, replicon integration and expression.

"Gene transfer" refers to the introduction of an exogenous polynucleotide into a cell which may encompass targeting, binding, uptake, transport, localization and replicon integration, but is distinct from and does not imply subsequent expression of the gene.

"Gene expression" or "expression" refers to the process of gene transcription, translation, and post-translational modification.

An "infectious" virus or viral particle is one that comprises a polynucleotide component which it is capable of delivering into a cell for which the viral species is trophic. The term does not necessarily imply any replication capacity of the virus.

The term "polynucleotide" refers to a polymeric form of nucleotides of any length, including deoxyribonucleotides or ribonucleotides, or analogs thereof. A polynucleotide may comprise modified nucleotides, such as methylated or capped nucleotides and nucleotide analogs, and may be interrupted by non-nucleotide components. If present, modifications to the nucleotide structure may be imparted before or after assembly of the polymer. The term polynucleotide, as used herein, refers interchangeably to double- and single-stranded molecules. Unless otherwise specified or required, any embodiment of the invention described herein that is a polynucleotide encompasses both the double-stranded form and each of two complementary single-stranded forms known or predicted to make up the double-stranded form.

A "transcriptional regulatory sequence" refers to a genomic region that controls the transcription of a gene or coding sequence to which it is operably linked. Transcriptional regulatory sequences generally include at least one transcriptional promoter and may also include one or more enhancers and/or terminators of transcription.

"Operably linked" refers to an arrangement of two or more components, wherein the components so described are in a relationship permitting them to function in a coordinated manner. By way of illustration, a transcriptional regulatory sequence or a promoter is operably linked to a coding sequence if the TRS or promoter promotes transcription of the coding sequence. An operably linked TRS is generally joined in cis with the coding sequence, but it is not necessarily directly adjacent to it.

"Heterologous" means derived from a genotypically distinct entity from the entity to which it is compared. For example, a polynucleotide introduced by genetic engineering techniques into a different cell type is a heterologous polynucleotide (and, when expressed, can encode a heterologous polypeptide). Similarly, a transcriptional regulatory element such as a promoter that is removed from its native coding sequence and operably linked to a different coding sequence is a heterologous transcriptional regulatory element.

A "terminator" refers to a polynucleotide sequence that tends to diminish or prevent read-through transcription (e.g., it diminishes or prevent transcription originating on one side of the terminator from continuing through to the other side of the terminator). The degree to which transcription is disrupted is typically a function of the base sequence and/or the length of the terminator sequence. In particular, as is well known in numerous molecular biological systems, particular DNA sequences, generally referred to as "transcriptional termination sequences" are specific sequences that tend to disrupt read-through transcription by RNA polymerase, presumably by causing the RNA polymerase molecule to stop and/or disengage from the DNA being transcribed. Typical example of such sequence-specific terminators include polyadenylation ("polyA") sequences, e.g., SV40 polyA. In addition to or in place of such sequence-specific terminators, insertions of relatively long DNA sequences between a promoter and a coding region also tend to disrupt transcription of the coding region, generally in proportion to the length of the intervening sequence. This effect presumably arises because there is always some tendency for an RNA polymerase molecule to become disengaged from the DNA being transcribed, and increasing the length of the sequence to be traversed before reaching the coding region would generally increase the likelihood that disengagement would occur before transcription of the coding region was completed or possibly even initiated. Terminators may thus prevent transcription from only one direction ("uni-directional" terminators) or from both directions ("bi-directional" terminators), and may be comprised of sequence-specific termination sequences or sequence-non-specific terminators or both. A variety of such terminator sequences are known in the art; and illustrative uses of such sequences within the context of the present invention are provided below.

"Host cells," "cell lines." "cell cultures," "packaging cell line" and other such terms denote higher eukaryotic cells, such as mammalian cells including human cells, useful in the present invention, e.g., to produce recombinant virus or recombinant fusion polypeptide. These cells include the progeny of the original cell that was transduced. It is understood that the progeny of a single cell may not necessarily be completely identical (in morphology or in genomic complement) to the original parent cell.

"Recombinant," as applied to a polynucleotide means that the polynucleotide is the product of various combinations of cloning, restriction and/or ligation steps, and other procedures that result in a construct that is distinct from a polynucleotide found in nature. A recombinant virus is a viral particle comprising a recombinant polynucleotide. The terms respectively include replicates of the original polynucleotide construct and progeny of the original virus construct.

A "control element" or "control sequence" is a nucleotide sequence involved in an interaction of molecules that contributes to the functional regulation of a polynucleotide, including replication, duplication, transcription, splicing, translation, or degradation of the polynucleotide. The regulation may affect the frequency, speed, or specificity of the process, and may be enhancing or inhibitory in nature.

Control elements known in the art include, for example, transcriptional regulatory sequences such as promoters and enhancers. A promoter is a DNA region capable under certain conditions of binding RNA polymerase and initiating transcription of a coding region usually located downstream (in the 3' direction) from the promoter. Promoters include AAV promoters, e.g., P5, P19, P40 and AAV ITR promoters, as well as heterologous promoters.

An "expression vector" is a vector comprising a region which encodes a gene product of interest, and is used for effecting the expression of the gene product in an intended target cell. An expression vector also comprises control elements operatively linked to the encoding region to facilitate expression of the protein in the target. The combination of control elements and a gene or genes to which they are operably linked for expression is sometimes referred to as an "expression cassette," a large number of which are known and available in the art or can be readily constructed from components that are available in the art.

The terms "polypeptide" and "protein" are used interchangeably herein to refer to polymers of amino acids of any length. The terms also encompass an amino acid polymer that has been modified; for example, disulfide bond formation, glycosylation, acetylation, phosphonylation, lipidation, or conjugation with a labeling component.

An "isolated" polynucleotide, e.g., plasmid, virus, polypeptide or other substance refers to a preparation of the substance devoid of at least some of the other components that may also be present where the substance or a similar substance naturally occurs or is initially prepared from. Thus, for example, an isolated substance may be prepared by using a purification technique to enrich it from a source mixture. Isolated nucleic acid, peptide or polypeptide is present in a form or setting that is different from that in which it is found in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. The isolated nucleic acid molecule may be present in single-stranded or double-stranded form. When an isolated nucleic acid molecule is to be utilized to express a protein, the molecule will contain at a minimum the sense or coding strand (e.g., the molecule may single-stranded), but may contain both the sense and anti-sense strands (e.g., the molecule may be double-stranded). Enrichment can be measured on an absolute basis, such as weight per volume of solution, or it can be measured in relation to a second, potentially interfering substance present in the source mixture. Thus, for example, a 2-fold enrichment, 10-fold enrichment, 100-fold enrichment, or a 1000-fold enrichment is envisioned.

The term "exogenous," when used in relation to a protein, gene, nucleic acid, or polynucleotide in a cell or organism refers to a protein, gene, nucleic acid, or polynucleotide which has been introduced into the cell or organism by artificial or natural means. An exogenous nucleic acid may be from a different organism or cell, or it may be one or more additional copies of a nucleic acid which occurs naturally within the organism or cell. By way of a non-limiting example, an exogenous nucleic acid is in a chromosomal location different from that of natural cells or is otherwise flanked by a different nucleic acid sequence than that found in nature, e.g., an expression cassette which links a promoter from one gene to an open reading frame for a gene product from a different gene.

"Transformed" or "transgenic" is used herein to include any host cell or cell line, which has been altered or augmented by the presence of at least one recombinant DNA sequence. The host cells of the present invention are typically produced by transfection with a DNA sequence in a plasmid expression vector, as an isolated linear DNA sequence, or infection with a recombinant viral vector.

The term "sequence homology" means the proportion of base matches between two nucleic acid sequences or the proportion amino acid matches between two amino acid sequences. When sequence homology is expressed as a percentage, e.g., 50%, the percentage denotes the proportion of matches over the length of a selected sequence that is compared to some other sequence. Gaps (in either of the two sequences) are permitted to maximize matching: gap lengths of 15 bases or less are usually used, 6 bases or less or 2 bases or less. When using oligonucleotides as probes or treatments, the sequence homology between the target nucleic acid and the oligonucleotide sequence is generally not less than 17 target base matches out of 20 possible oligonucleotide base pair matches (85%); not less than 9 matches out of 10 possible base pair matches (90%), or not less than 19 matches out of 20 possible base pair matches (95%).

Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less or 2 or less. Alternatively, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. The two sequences or parts thereof are more homologous if their amino acids are greater than or equal to 50% identical when optimally aligned using the ALIGN program.

The term "corresponds to" is used herein to mean that a polynucleotide sequence is structurally related to all or a portion of a reference polynucleotide sequence, or that a polypeptide sequence is structurally related to all or a portion of a reference polypeptide sequence, e.g., they have at least 80%, 85%, 90%, 95% or more, e.g., 99% or 100%, sequence identity. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The term "sequence identity" means that two polynucleotide sequences are identical (e.g., on a nucleotide-by-nucleotide basis) over the window of comparison. The term "percentage of sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I)

occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denote a characteristic of a polynucleotide sequence, wherein the polynucleotide comprises a sequence that has at least 85 percent sequence identity, at least 90 to 95 percent sequence identity, or at least 99 percent sequence identity as compared to a reference sequence over a comparison window of at least 20 nucleotide positions, frequently over a window of at least 20-50 nucleotides, wherein the percentage of sequence identity is calculated by comparing the reference sequence to the polynucleotide sequence which may include deletions or additions which total 20 percent or less of the reference sequence over the window of comparison.

As used herein, "substantially pure" or "purified" means an object species is the predominant species present (e.g., on a molar basis it is more abundant than any other individual species in the composition), for instance, a substantially purified fraction is a composition wherein the object species comprises at least about 50 percent (on a molar basis) of all macromolecular species present. Generally, a substantially pure composition will comprise more than about 80 percent of all macromolecular species present in the composition, or more than about 85%, about 90%, about 95%, and about 99%. The object species may be purified to essential homogeneity (contaminant species cannot be detected in the composition by conventional detection methods) wherein the composition consists essentially of a single macromolecular species.

"Lymphangiogenesis" means the process of formation of lymphatic vessels from pre-existing lymphatic vessels and "angiogenesis" means the process of formation of blood vessels from pre-existing blood vessels. As used herein, "angiogenic" includes angiogenic and lymphangiogenic. For example, a composition is angiogenic if it causes the formation of new blood vessels and anti-angiogenic if it reduces the formation of new blood vessels.

As used herein, "apoptosis"—programmed cell death—means the genetically directed process of cell self-destruction that is marked by the fragmentation of nuclear DNA, is activated either by the presence of a stimulus or removal of a suppressing agent or stimulus, is a normal physiological process eliminating DNA-damaged, superfluous, or unwanted cells, and when halted (as by genetic mutation) may result in uncontrolled cell growth and tumor formation. Therefore, a composition is pro-apoptotic if it increases cell death and anti-apoptotic if it increases cell survival (reduces cell death).

As used herein, "subject" means an individual to whom compositions of the invention are administered. In some embodiments, the subject is a human. In other embodiments, the subject is a non-human mammal, e.g., a horse, cow, sheep, pig, deer, dog, cat, rat, or a mouse.

Exemplary Peptides Useful for Angiogenic Therapies

AKIP1 is expressed in numerous cancer cell types including lung (A541), breast (MD-MBA231), eye (OMM1-3) and brain (U87-MG) cancer cell lines. AKIP1 expression is minimal in normal brain but highly expressed in Glioblastoma Multiforme (GBM) cell lines. By evaluating AKIP1 knockout cell lines, it was found that AKIP1 is essential for tumor progression (see examples below) and that the specific isoforms (splice variants) of AKIP1 show differential binding to key interacting proteins such as PKAc, AIF, HSP-70 and p65 subunit of NF-kappaB. Furthermore, AKIP1a, which has both third and fifth exons intact, is the only isoform that causes tumorigenesis (as opposed to AKIP1b, AKIP1c, and AKIP1d). Consequently, peptides corresponding to regions of AKIP1 and to regions of interacting proteins, PKAc, AiF, HSP-70 and p65 subunit of NF-kappaB, that disrupt these interactions are useful in the treatment of subjects with or at risk of angiogenic disorders.

Provided herein are compositions including peptides and nucleic acids encoding the peptides referred herein as AKIP1 Disrupting Peptides (ADPs), Exemplary peptides are shown in Table 1.

TABLE 1

| Peptide Name | Protein | SEQ ID No. | Amino Acid Sequence | Length |
|---|---|---|---|---|
| PEPTIDE1 | AKIP1 | 1 | REERPPTLSASFRTMAEFMDYTSSQCG (SEQ ID NO: 1) | 27 |
| PEPTIDE2 | AKIP1 | 2 | RKDRKKTSLGPGGSYQISEHAPEASQP (SEQ ID NO: 2) | 27 |
| PEPTIDE3 | AKIP1 | 3 | RRAVDWHALERPKGCMGVLAREAPHLEKQPAAGPQRVLPGE (SEQ ID NO: 3) | 41 |
| PEPTIDE4 | AKIP1 | 4 | VTVGSNDLTKKTHVVAVDSGQSVDLVFPV (SEQ ID NO: 4) | 29 |
| PEPTIDE5 | AKIP1 | 5 | DIGNGQRKDRKKTSLGPGGSYQISEHA (SEQ ID NO: 5) | 27 |
| PEPTIDE6 | p65 | 6 | NSTDPAVFTDLASVDNSEFQQLLNQGIPVAPHTTEPMLMEYPEAITRLV (SEQ ID NO: 6) | 49 |
| PEPTIDE7 | AKIP1 | 7 | GGSYQISEHAPEASQPAENISKDLYIEVYPGTYS (SEQ ID NO: 7) | 34 |
| PEPTIDE8 | p65 | 8 | VKKRDLEQAISQRIQTNNNPFQVPIEEQRGDYDLNAVR (SEQ ID NO: 8) | 38 |
| PEPTIDE9 | AKIP1 | 9 | KYYSSVPEEGGATHVYRYHRGESKLHM (SEQ ID NO: 9) | 27 |

TABLE 1-continued

| Peptide Name | Protein | SEQ ID No. | Amino Acid Sequence | Length |
|---|---|---|---|---|
| PEPTIDE10 | PKAc beta1 | 10 | SHFSEHTALWDRSMKEFLAKAKEDFLK K (SEQ ID NO: 10) | 28 |
| PEPTIDE11 | AKIP1 | 11 | LNGVDRRSLQRSARLALEVLERAK (SEQ ID NO: 11) | 24 |
| PEPTIDE12 | AKIP1 | 12 | DNCLAAAALNGVDRRSLQRSARLALEV LERAKR (SEQ ID NO: 12) | 33 |
| PEPTIDE13 | HSP-70 | 13 | IMQDKLEKERNDAKNAVEEYVYEMRD KLSGEYEKFVSEDDRNSFTLKLEDTEN WLY (SEQ ID NO: 13) | 56 |
| PEPTIDE14 | p65 | 14 | PLIFPAEPAQASGPYVEIIEQPKQ (SEQ ID NO: 14) | 24 |
| PEPTIDE15 | HSP-70 | 15 | KSQVISNAKNTVQGFKRFHGRAFSDPF VEAEKSNLAYDIVQWPTGLTGIKVTYM EEERNFTTEQVTAMLLSKLKETAESVL KKPVV (SEQ ID NO: 15) | 86 |
| PEPTIDE16 | PKAc alpha | 16 | TWTLCGTPEYLAPEIILSKGYNKAVDW WALGVLIYEMAAGYPP (SEQ ID NO: 16) | 43 |
| PEPTIDE17 | PKAc alpha | 17 | DWWALGVLIYEMAAGYPP (SEQ ID NO: 17) | 18 |
| PEPTIDE18 | p65 | 18 | VKKRDLEQAISQRIQTNNN (SEQ ID NO: 18) | 19 |

The disclosed peptides, in some cases, correlate with specific domains of AKIP1 or one of the interacting proteins.

TABLE 2

| Peptide | Protein | Domain | Domain Region |
|---|---|---|---|
| PEPTIDE1 | AKIP1 | — | — |
| PEPTIDE2 | AKIP1 | — | — |
| PEPTIDE3 | AKIP1 | — | — |
| PEPTIDE4 | AKIP1 | COG1470 super family | 168-207 |
| PEPTIDE5 | AKIP1 | — | — |
| PEPTIDE6 | p65 | Transcriptional activation domain 1 | 415-476 |
| PEPTIDE7 | AKIP1 | COG1470 super family | 168-207 |
| PEPTIDE8 | p65 | Rel Homology Domain | 21-186 |
| PEPTIDE9 | AKIP1 | — | — |
| PEPTIDE10 | PKAc beta1 | — | — |
| PEPTIDE11 | AKIP1 | — | — |
| PEPTIDE12 | AKIP1 | — | — |
| PEPTIDE13 | HSP-70 | — | — |
| PEPTIDE14 | p65 | Rel Homology Domain | 21-186 |
| PEPTIDE15 | HSP-70 | Nucleotide Binding Domain | 2-384 |
| PEPTIDE16 | PKAc alpha | Protein Kinase Domain | 44-298 |
| PEPTIDE17 | PKAc alpha | Protein Kinase Domain | 44-298 |
| PEPTIDE18 | p65 | Rel Homology Domain | 21-186 |

Provided herein are pharmaceutical compositions that include an effective amount of an AKIP1-disrupting peptide, the peptide comprising at least 85% amino acid sequence identity to one of the amino acid sequences selected from the group consisting of PEPTIDE1, PEPTIDE2, PEPTIDE3, PEPTIDE4, PEPTIDE5, PEPTIDE7, PEPTIDE8, PEPTIDE9, PEPTIDE10, PEPTIDE11, PEPTIDE13, PEPTIDE14, PEPTIDE15, PEPTIDE16, PEPTIDE17 and PEPTIDE18, wherein the peptide induces apoptosis or cell death.

Provided herein are pharmaceutical compositions that include an effective amount of an AKIP1-disrupting peptide, the peptide comprising at least 85% amino acid sequence identity to one of the amino acid sequences selected from the group consisting of PEPTIDE4, PEPTIDE6, PEPTIDE8, PEPTIDE10, PEPTIDE11, PEPTIDE12 and PEPTIDE16, wherein the peptide induces (enhances) cell survival.

In certain embodiments, the peptide has substantial identity, e.g., at least 85%, at least 90%, at least 92%, at least 94%, at least 95%, at least 96%, at least 97%, at least 98%, or at least 99% sequence identity to a peptide listed in Table 1.

Conservative amino acid substitutions relative to the sequences in Table 1 may be employed—that is, for example, aspartic-glutamic as acidic amino acids; lysine/arginine/histidine as polar basic amino acids; leucine/isoleucine/methionine/valine/alanine/proline/glycine non-polar or hydrophobic amino acids; serine/threonine as polar or hydrophilic amino acids. Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting peptide, polypeptide or fusion polypeptide. Whether an amino acid change results in a functional peptide, polypeptide or fusion polypeptide can readily be determined by assaying the specific activity of the peptide, polypeptide or fusion polypeptide.

Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, or (c) the bulk of the side chain. Naturally occurring residues are divided into groups based on common side-chain properties:

Alternative embodiments also include a peptide, polypeptide or fusion polypeptide with non-conservative substitutions. Non-conservative substitutions entail exchanging a member of one of the classes described above for another.

The peptides can include additional peptide sequence as fusions. The peptide or fusion proteins of the invention can be synthesized in vitro, e.g., by the solid phase peptide synthetic method, or by recombinant DNA approaches, both methods known in the art. The peptides or fusion proteins can be purified by fractionation on immunoaffinity or ion-exchange columns; ethanol precipitation; reverse phase HPLC; chromatography on silica or on an anion-exchange resin such as DEAE; chromatofocusing; SDS-PAGE; ammonium sulfate precipitation; gel filtration using, for example. Sephadex G-75; or ligand affinity chromatography.

The disclosed peptides may include a fusion with a tissue-penetrating peptide (TPP) or cell-penetrating peptide (CPP) sequence, including, but not limited to, Protein Transduction Domains (PTDs), elastin like polypeptide for delivery to CNS, CPP-Adaptor Systems including non-covalent and reversible conjugations to calmodulin, and activatable cell penetrating nanocarriers sensitive to metalloproteinases. Other examples include, but are not limited to, those in the table below.

TABLE 3

| Type | Name |
| --- | --- |
| Amphipathic | Transportan |
|  | Pep-1 |
|  | MPG |
|  | [FΦR4-A5]Rho |
|  | MAP(Aib) |
|  | pVEC |
| Cationic | Tat(48-60) |
|  | Penetratin |
|  | Oligo-D-arginine |
|  | Cyc-r7 |
|  | [D]-K6L9 |
|  | cyclic [W(RW)4] |
|  | NrTP5 |
|  | hPP3 |
| Hydrophobic | C105Y |
|  | PFV |
| Anionic | PepNeg |
|  | p28 |

In certain embodiments, the peptide fusion is with a linear tumor or cardiac penetrating peptide sequence (TPP/CTP) for delivery to cancer or heart cells. The TPP sequence—MAKRGARSTA—(SEQ ID No:58) has an embedded CendR motif (R/K/XXR/K) to induce both cellular uptake and tissue penetration.

Cardiovascular delivery vehicles for the peptides, polypeptides and/or fusion polypeptides include but are not limited to hydrogels, peptide nanofibers, and cardiac targeting peptides.

Tissue targeting peptides may include CPP-Ts such as from scorpion venom CPPs for brain drug delivery including but not limited to those in Table 4:

TABLE 4

| Proposed transport(s) | Peptide BBB |
| --- | --- |
| nAChRs | RVG29 |
|  | CDX |
|  | CDX |
| LRP/LDLR | Angiopep-2 |
|  | ApoB (3371-3409) |
|  | ApoE (159-167)2 |
|  | Peptide-22 |
| TfR | TfR B6 |
|  | T7 |
|  | THR |
| Leptin receptor | Leptin 30 |
| KCa channel | Apamin |
|  | ApOO |
|  | MiniAp-4 |
| GSH transporter | GSH |
| GM1 | G23 |
| Opioid receptor | g7 |
| Unknown receptor | Tat(47-57) |
|  | SynB1 |
| Passive transport | Diketopiperazines |
|  | Phenylproline oligomers |
| Active transport | PepH3 |
| Passive & active transport | PepNeg |

In some embodiments, the disclosed peptides are included in a non-antibody scaffold. A non-antibody scaffold includes, but is not limited to, adnectins, affibodies, affilins, anticalins, atrimers, avimers bicyclic peptides, Centyrin, Cys-knots, DARPins, fynomers, Kunitz domain, O-bodies, pronectins, and Tn3. A table of representative uses for specific scaffolds is provided below.

TABLE 5

| Scaffold | Target protein | Indications |
| --- | --- | --- |
| Adnectins | PCSK9 | Hypercholesterolemia |
|  | VEGFR2 | Cancer |
|  | Myostatin | Cachexia |
|  | EGFR/IGF-1R | Cancer |
| Affibodies | HER2 | Cancer (PET imaging) |
|  | Complement protein C5 | Inflammation |
|  | IL-17 | Autoimmunity |
|  | TNF/IL-6 (AffiMab) | Inflammation |
|  | EGFR, IGF-1R, PDGFRβ, HER3, VEGFR2 | Cancer |
| Affilins | Fibronectin EDB splice variant | Cancer |
|  | CTLA-4 | Cancer |
|  | VEGF-A | Cancer |
| Anticalins | Hepcidin | Anemia |
|  | IL-4Rα | Asthma |
|  | HGFR | Cancer |
|  | CD137/HER2 | Cancer |
|  | IL-23/IL-17 | Autoimmunity |
| Atrimers | IL-23 | Inflammation |
|  | DR4 | Cancer |
| Avimers | IL-6 | Crohn's disease |
| Bicyclic peptides | Kallikrein uPA HER2 | Hereditary angioedema Cancer |
| Centyrin | HGFR | Cancer |
|  | IL-17 | Autoimmunity |
|  | TNF-α | Inflammation |
| Cys-knots | NaV1.7 | Pain |
| DARPins | VEGF-A | Macular degeneration Macular edema |
|  | VEGF-A/PDGF-B | Macular degeneration |
|  | VEGF/HGF | Cancer |
|  | HER2 | Cancer |
| Fynomers | TNF/IL-17A (FynomAb) | Plaque psoriasis |
|  | HER2 (FynomAb) | Cancer |
| Kunitz domains | Kallikrein | Hereditary angioedema |
|  | Neutrophil elastase | Acute respiratory distress syndrome |
|  | Plasmin | Cancer |

TABLE 5-continued

| Scaffold | Target protein | Indications |
| --- | --- | --- |
| Pronectins | VEGFR2, AXL tyrosine kinase, TNF-α, FZD receptors | Cancer, Autoimmunity |
| Tn3 | CD40L TRAILR2 | Autoimmunity |

Chemically modified derivatives of a given peptide or fusion thereof can be readily prepared by methods known in the art. For example, amides of the peptide or fusion thereof can be prepared by techniques for converting a carboxylic acid group or precursor, to an amide. For example, the peptide or fusion can be cleaved from a solid support with an appropriate amine, or in the presence of an alcohol, yielding an ester, followed by aminolysis with the desired amine.

Salts of carboxyl groups of a peptide or fusion thereof may be prepared in the usual manner by contacting the peptide, polypeptide, or fusion thereof with one or more equivalents of a desired base such as, for example, a metallic hydroxide base, e.g., sodium hydroxide; a metal carbonate or bicarbonate base such as, for example, sodium carbonate or sodium bicarbonate; or an amine base such as, for example, triethylamine, triethanolamine, and the like.

In some embodiments, the peptide can include N- or C-terminal modifications. N-acyl derivatives of an amino group of the peptide or fusion thereof may be prepared by utilizing an N-acyl protected amino acid for the final condensation, or by acylating a protected or unprotected peptide, polypeptide, or fusion thereof. O-acyl derivatives may be prepared, for example, by acylation of a free hydroxy polypeptide or polypeptide resin. Either acylation may be carried out using standard acylating reagents such as acyl halides, anhydrides, acyl imidazoles, and the like. Both N- and O-acylation may be carried out together, if desired.

Formyl-methionine, pyroglutarine and trimethyl-alanine may be substituted at the N-terminal residue of the polypeptide. Other amino-terminal modifications include aminooxypentane modifications. Other N-terminal modifications include, but are not limited to, methylation, acetylation, biotinylation, dansylation, 2, 4-dinitrophenyl, formylation, propionylation, pyroglutamate, myristoylation, palmitoylation, mono-methylation, 7-methoxycoumarin acetic acid (Mca), fluorophores and fluorescent dyes.

Amino acid substitutions may include D amino acids, as well as other analogs, e.g., unnatural amino acids such as alpha,alpha-disubstituted amino acids, N-alkyl amino acids, lactic acid, and the like. These analogs include, but are not limited to, phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, alpha-methyl-alanine, para-benzoyl-phenylalanine, phenylglycine, propargylglycine, sarcosine, epsilon-N,N,N-trimethyllysine, epsilon-N-acetyllysine, N-acetylserine, N-formylmethionine, 3-methylhistidine, 5-hydroxylysine, omega-N-methylarginine, and other similar amino acids and imino acids and tert-butylglycine. Internal amino acid sequence modifications include, but are not limited to, cyclization (disulfide bonds), cysteine carbamidomethylation (CAM), and phosphorylation.

C-terminal modification include, but are not limited to, C-terminal glycosyl phosphatidylinositol (GPI) anchor, methylation, alpha-amidation, fluorophores and fluorescent dyes.

In some embodiments, the peptide can be a peptidomimetic. Peptidomimetics refer to a synthetic chemical compound which has substantially the same structural and/or functional characteristics of the peptides of the invention. The mimetic can be entirely composed of synthetic, non-natural amino acid analogues, or can be a chimeric molecule including one or more natural peptide amino acids and one or more non-natural amino acid analogs. The mimetic can also incorporate any number of natural amino acid conservative substitutions as long as such substitutions do not destroy the activity of the mimetic. Routine testing can be used to determine whether a mimetic has the requisite activity, e.g., that it induces apoptosis or cell death.

The peptide can be linear, cyclic or branched. Cyclic peptides can be synthesized by methods known in the art such as disclosed in U.S. Pat. No. 9,035,022. Branched peptides can be synthesized by methods known in the art such as disclosed in U.S. Pat. No. 8,440,794.

In some embodiments, the composition can be formulated as a pro-drug. As used herein, the term "pro-drug" refers to a pharmacological substance (drug) that is administered in an inactive (or significantly less active) form. Once administered, the pro-drug is metabolized in vivo into an active metabolite. The rationale behind the use of a pro-drug is generally for absorption, distribution, metabolism, and excretion (ADME) optimization. Pro-drugs are usually designed to improve oral bioavailability, with poor absorption from the gastrointestinal tract usually being the limiting factor. Additionally, the use of a pro-drug strategy increases the selectivity of the drug for its intended target. The peptide can be formulated as a pro-drug by, for example, esterification or perbutyrylation.

In some embodiments, the peptide is conjugated to one or more other peptides or polypeptides, including, but not limited to, bovine serum albumin, ovalbumin, or keyhole limpet hemocyanin.

In some embodiments, the peptide is conjugated to polyethylene glycol (PEGylated). Methods for pegylating peptides are known in the art. See, for example, U.S. Patent Publication No. 20170232111.

In some embodiments, the peptide includes a bridging peptide in association with another peptide or protein. Bridging peptides can be synthesized by methods known in the art such as disclosed in U.S. Patent Publication No. 20110092677.

Acid addition salts of the peptide, polypeptide or fusion polypeptide or of amino residues of the peptide, polypeptide or fusion polypeptide may be prepared by contacting the polypeptide or amine with one or more equivalents of the desired inorganic or organic acid, such as, for example, hydrochloric acid. Esters of carboxyl groups of the polypeptides may also be prepared by any of the usual methods known in the art.

Provided herein are pharmaceutical compositions that include an effective amount of an isolated nucleic acid comprising a nucleotide sequence encoding an AKIP1-disrupting peptide comprising at least 85% amino acid sequence identity to one of the amino acid sequences selected from the group consisting of PEPTIDE1, PEPTIDE2, PEPTIDE3, PEPTIDE4, PEPTIDE5, PEPTIDE7, PEPTIDE8, PEPTIDE9, PEPTIDE10, PEPTIDE11, PEPTIDE13, PEPTIDE14, PEPTIDE15, PEPTIDE16, PEPTIDE17 and PEPTIDE18, wherein the peptide induces apoptosis or cell death, or alters angiogenesis.

Provided herein are pharmaceutical compositions that include an effective amount of an isolated nucleic acid comprising a nucleotide sequence encoding an AKIP1- disrupting peptide, the peptide comprising at least 85% amino acid sequence identity to one of the amino acid sequences selected from the group consisting of PEPTIDE4, PEPTIDE6, PEPTIDE8, PEPTIDE10, PEPTIDE11, PEPTIDE12 and PEPTIDE16, wherein the peptide induces (enhances) cell survival.

The nucleic acids encoding an AKIP1-disrupting peptide disclosed herein can be incorporated into delivery vectors for administration to a subject. Delivery vectors include, for example, viral vectors, liposomes and other lipid-containing complexes, and other macromolecular complexes capable of mediating delivery of a gene to a host cell. Vectors can also comprise other components or functionalities that further modulate gene delivery and/or gene expression, or that otherwise provide beneficial properties. Such other components include, for example, components that influence binding or targeting to cells (including components that mediate cell-type or tissue-specific binding); components that influence uptake of the vector by the cell; components that influence localization of the transferred gene within the cell after uptake (such as agents mediating nuclear localization); and components that influence expression of the gene. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. Selectable markers can be positive, negative or bifunctional. Positive selectable markers allow selection for cells carrying the marker, whereas negative selectable markers allow cells carrying the marker to be selectively eliminated. A variety of such marker genes have been described, including bifunctional (e.g., positive/negative) markers (see, e.g., WO 92/08796; and WO 94/28143). Such marker genes can provide an added measure of control that can be advantageous in gene therapy contexts.

A large variety of such vectors are known in the art and are generally available. Vectors within the scope of the invention include, but are not limited to, isolated nucleic acid, e.g., plasmid-based vectors which may be extrachromosomally maintained, and viral vectors, e.g., recombinant adenovirus, retrovirus, lentivirus, herpesvirus, poxvirus, papilloma virus, or adeno-associated virus, including viral and non-viral vectors which are present in liposomes, e.g., neutral or cationic liposomes, such as DOSPA/DOPE, DOGS/DOPE or DMRIE/DOPE liposomes, and/or associated with other molecules such as DNA-anti-DNA antibody-cationic lipid (DOTMA/DOPE) complexes. Exemplary gene viral vectors are described below. Vectors may be administered via any route including, but not limited to, intramuscular, buccal, rectal, intravenous or intracoronary administration, and transfer to cells may be enhanced using electroporation and/or iontophoresis.

Any of the above compositions (peptide or nucleic acid) can further include a carrier system for cargo delivery. These include, but are not limited to, polymer matrices, polymeric nanoparticles, nanoworms, hydrogels, liposomes, phosphorodiamidate morpholino oligomers (PMOs) and peptide nucleic acids (PNAs).

Exemplary Methods

Provided herein are methods for the treatment or prevention of angiogenic conditions or angiogenic disorders, or inhibition of one or more symptoms thereof, by administering the compositions disclosed above to a subject that has or is at risk of having an angiogenic condition or angiogenic disorder.

In some embodiments, a method for the treatment of angiogenic conditions or angiogenic disorders is provided that includes administering a therapeutically effective amount of the disclosed compositions herein to a subject in need or at risk thereof, in such amounts and for such time as is necessary to achieve the desired result. In certain embodiments of the present invention a "therapeutically effective amount" of an inventive targeted particle is that amount effective for treating, alleviating, ameliorating, relieving, delaying onset of, inhibiting progression of, reducing severity of, and/or reducing incidence of one or more symptoms or features of an angiogenic conditions or angiogenic disorders.

In some embodiments, a method for administering disclosed compositions to a subject suffering from angiogenic conditions or angiogenic disorders or relapse is provided. In some embodiments, disclosed compositions are administered to a subject in such amounts and for such time as is necessary to achieve the desired result. In certain embodiments, a "therapeutically effective amount" of the disclosed compositions is that amount effective for treating, alleviating, ameliorating, relieving, delaying onset of, inhibiting progression of, reducing severity of, and/or reducing incidence of one or more symptoms or features of an angiogenic condition or angiogenic disorder. In some embodiments, the disclosed compositions are administered to a subject previously treated for an angiogenic condition or angiogenic disorder. In some embodiments, the disclosed compositions are administered to a subject with a family history of an angiogenic condition or angiogenic disorder. In some embodiments, the disclosed compositions are administered to a subject with a predisposition for an angiogenic condition or angiogenic disorder. For example, a subject who is BRCA-positive is genetically predisposed to certain forms of breast cancer.

A therapeutically effective amount of the disclosed compositions can be administered to a healthy individual (e.g., a subject who does not display any symptoms of cancer and/or who has not been diagnosed with cancer). For example, healthy individuals may be "immunized" with the disclosed compositions prior to development of an angiogenic condition or angiogenic disorder and/or onset of symptoms of an angiogenic condition or angiogenic disorder; at risk individuals (e.g., patients who have a family history of an angiogenic condition or angiogenic disorder; patients carrying one or more genetic mutations associated with development of an angiogenic condition or angiogenic disorder; patients having a genetic polymorphism associated with development of an angiogenic condition or angiogenic disorder; patients infected by a virus associated with development of an angiogenic condition or angiogenic disorder; patients with habits and/or lifestyles associated with development of an angiogenic condition or angiogenic disorder; etc.) can be treated substantially contemporaneously with (e.g., within 48 hours, within 24 hours, or within 12 hours of) the onset of symptoms of an angiogenic condition or angiogenic disorder.

Provided herein are methods for the treatment or prevention of an angiogenic disorder in a subject by administering any of the compositions disclosed herein.

In some embodiments, the angiogenic condition can be treated with an anti-angiogenic composition of the invention. In some embodiments, provided herein are methods to prevent, inhibit or treat an angiogenic disorder by administering to a subject an effective amount of an AKIP1-disrupting peptide, the peptide comprising at least 85% amino acid sequence identity to one of the amino acid sequences selected from the group consisting of PEPTIDE1, PEPTIDE2, PEPTIDE3, PEPTIDE4, PEPTIDE5, PEPTIDE7, PEPTIDE8, PEPTIDE9, PEPTIDE10, PEPTIDE11, PEPTIDE13, PEPTIDE14, PEPTIDE15, PEPTIDE16, PEPTIDE17 and PEPTIDE18, wherein the peptide induces apoptosis or cell death, or alters angiogenesis.

In some embodiments, provided herein are methods to prevent, inhibit or treat an angiogenic disorder by administering to a subject an effective amount of a nucleic acid comprising a nucleotide sequence encoding an AKIP1-disrupting peptide, the peptide comprising at least 85% amino acid sequence identity to one of the amino acid sequences selected from the group consisting of PEPTIDE1, PEPTIDE2, PEPTIDE3, PEPTIDE4, PEPTIDE5, PEPTIDE7, PEPTIDE8, PEPTIDE9, PEPTIDE10, PEPTIDE11, PEPTIDE13, PEPTIDE14, PEPTIDE15, PEPTIDE16, PEPTIDE17 and PEPTIDE18, wherein the peptide induces apoptosis or cell death, or alters angiogenesis.

In some embodiments, the angiogenic condition that can be treated with an anti-angiogenic composition is cancer. Exemplary cancers to which the compositions and methods of the invention apply include a solid tumor including, but not limited to, brain, ovary, breast, lung, thyroid, lymph node, kidney, ureter, bladder, teste, prostate, skin, bone, skeletal muscle, bone marrow, stomach, esophagus, small bowel, colon, rectum, pancreas, liver, smooth muscle, spinal cord, nerves, ear, eye, nasopharynx, oropharynx, salivary gland, blood vessels, or the heart, and including leukemia. Examples of brain cancers include, but are not limited to, neuroma, anaplastic astrocytoma, neuroblastoma, glioma, glioblastoma multiforme, astrocytoma, meningioma, pituitary adenoma, primary CNS lymphoma, medulloblastoma, ependymoma, sarcoma, oligodendroglioma, medulloblastomrna, spinal cord tumor, and schwannoma. Ovarian cancers include, but are not limited to, ovarian epithelial carcinoma and germ cell tumors. Breast cancers include, but are not limited to, ductal carcinoma in situ (DCIS), infiltrating (or invasive) ductal carcinoma (IDC), or infiltrating (or invasive) lobular carcinoma (ILC). Lung cancers include, but are not limited to, small cell and non-small cell primary lung cancer as well as cancers that metastasize to the lungs or the lung lymphatics. Thyroid cancers include, but are not limited to, papillary and/or mixed papillary/follicular, follicular and/or Hurthle cell, medullary and anaplastic. Kidney cancers include, but are not limited to, renal cell carcinoma, transitional cell carcinoma, Wilms tumor, and renal sarcoma. Types of bladder cancers include squamous cell carcinoma and adenocarcinoma. Skin cancers include, but are not limited to, squamous cell carcinoma, Kaposi's sarcoma, malignant melanoma, Merkel cell skin cancer, and non-melanoma skin cancer. Bone cancers include, but are not limited to, osteosarcoma, chondrosarcoma, and the Ewing Sarcoma Family of Tumors (ESFTs). Pancreatic cancers include, but are not limited to, exocrine pancreatic cancers and endocrine pancreatic cancers. Exocrine pancreatic cancers include, but are not limited to, adenocarcinomas, acinar cell carcinomas, adenosquamous carcinomas, colloid carcinomas, undifferentiated carcinomas with osteoclast-like giant cells, hepatoid carcinomas, intraductal papillary-mucinous neoplasms, mucinous cystic neoplasms, pancreatoblastomas, serous cystadenomas, signet ring cell carcinomas, solid and pseudopapillary tumors, pancreatic ductal carcinomas, and undifferentiated carcinomas. Endocrine pancreatic cancers include, but are not limited to, insulinomas and glucagonomas. Liver cancers include, but are not limited to, hepatocellular carcinoma (liver cell carcinomas with or without fibrolamellar variant), cholangiocarcinomrna (intrahepatic bile duct carcinoma), and mixed hepatocellular cholangiocarcinoma. Eye cancers include, but are not limited to, intraocular melanoma and retinoblastoma. Blood vessel cancers include hemangiomas. Other cancers include von Hippel-Lindau disease, Castleman's disease, lymphadenopathy, X-linked lymphoproliferative disorder, and Non-Hodgkin's Lymphoma.

In other embodiments, the disclosed compositions can be used to inhibit the growth of cancer cells, e.g., glioblastoma cells. As used herein, the term "inhibits growth of cancer cells" or "inhibiting growth of cancer cells" refers to any slowing of the rate of cancer cell proliferation and/or migration, arrest of cancer cell proliferation and/or migration, or killing of cancer cells, such that the rate of cancer cell growth is reduced in comparison with the observed or predicted rate of growth of an untreated control cancer cell. The term 'inhibits growth' can also refer to a reduction in size or disappearance of a cancer cell or tumor, as well as to a reduction in its metastatic potential. Such an inhibition at the cellular level may reduce the size, deter the growth, reduce the aggressiveness, or prevent or inhibit metastasis of a cancer in a patient. Those skilled in the art can readily determine, by any of a variety of suitable indicia, whether cancer cell growth is inhibited.

Inhibition of cancer cell growth may be evidenced, for example, by arrest of cancer cells in a particular phase of the cell cycle, e.g., arrest at the G2/M phase of the cell cycle. Inhibition of cancer cell growth can also be evidenced by direct or indirect measurement of cancer cell or tumor size. In human cancer patients, such measurements generally are made using well known imaging methods such as magnetic resonance imaging, computerized axial tomography and X-rays. Cancer cell growth can also be determined indirectly, such as by determining the levels of circulating carcinoembryonic antigen, prostate specific antigen or other cancer-specific antigens that are correlated with cancer cell growth. Inhibition of cancer growth is also generally correlated with prolonged survival and/or increased health and well-being of the subject.

Compositions of this disclosure can be administered in combination with at least a further pharmaceutically effective anti-cancer agent. Chemotherapeutic agents, radiation, anti-angiogenic molecules, or other agents may also be utilized. For example, in treating metastatic breast cancer, useful chemotherapeutic agents include cyclophosphamide, doxorubicin, paclitaxel, docetaxel, navelbine, capecitabine, and mitomycin C, among others. Combination chemotherapeutic regimens have also proven effective including cyclophosphamide+methotrexate+5-fluorouracil; cyclophospharnide+doxorubicin+5-fluorouracil; or, cyclophosphamide+doxorubicin, for example. Other compounds such as prednisone, a taxane, navelbine, mitomycin C, or vinblastine have been utilized for various reasons. A majority of breast cancer patients have estrogen-receptor positive (ER+) tumors and in these patients, endocrine therapy (e.g., tamoxifen) is usually employed over chemotherapy. For such patients, tamoxifen or, as a second line therapy, progestins (medroxyprogesterone acetate or megestrol acetate) are employed. Aromatase inhibitors (e.g., aminoglutethimide and analogs thereof such as letrozole) decrease the availability of estrogen needed to maintain tumor growth and may be used as second or third line endocrine therapy in certain patients.

Other cancers may require different chemotherapeutic regimens. For example, metastatic colorectal cancer is typically treated with Camptosar (irinotecan or CPT-11), 5-fluorouracil or leucovorin, alone or in combination with one another. Proteinase and integrin inhibitors such as the MMP inhibitors marimastate (British Biotech), COL-3 (Collagenex), Neovastat (Aeterna), AG3340 (Agouron), BMS-275291 (Bristol Myers Squibb), CGS 27023A (Novartis) or the integrin inhibitors Vitaxin (Medimmune), or MED1522 (Merck KgaA) may also be suitable for use.

In some embodiments, the angiogenic condition that can be treated with an anti-angiogenic composition of the invention is an infectious disease, which can include cholera, typhoid, tuberculosis, human immunodeficiency virus (HIV), *Leishmania major* Infection, herpetic stromal keratitis, dengue hemorrhagic fever, dengue shock syndrome, hantavirus pulmonary syndrome, hemorrhagic fever with renal syndrome, pustular skin disease, smallpox, dracunculiasis, Human African trypanosomiasis, leishmaniasis, leprosy, pneumonia, HPV, gonorrhea, syphilis, anthrax, mononucleosis, viral conjunctivitis, lymphatic filariasis, onchocerciasis, schistosomiasis, soil-transmitted helminthiases, trachorna, acute viral encephalitis, West Nile fever, Zika, malaria, Japanese encephalitis, tularemia, Chagas, sandfly fever, plague, rickettsiosis, influenza, cervicovaginal infections, and decubitus ulcers.

In some embodiments, the angiogenic condition that can be treated with an anti-angiogenic composition of the invention is neutropenia, ocular neovascularization, retinal vascular disease, or neovascular glaucoma.

In some embodiments, the angiogenic condition that can be treated with an anti-angiogenic composition of the invention is meningitis, encephalitis, or sleep apnea.

In some embodiments, the angiogenic condition that can be treated with an anti-angiogenic composition of the invention is obesity, gestational diabetes mellitus, proliferative diabetic retinopathy, diabetic macular edema, familial hypercholesterolernia.

In some embodiments, the angiogenic condition that can be treated with an anti-angiogenic composition of the invention is a skin or subcutaneous disorder such as cutaneous inflammation, psorisis, phototoxicity, chronic skin inflammation, atopic dermatitis, eczema, and polymyositisidermatomyositis.

In some embodiments, the angiogenic condition that can be treated with an anti-angiogenic composition of the invention is a chronic inflammatory disease such as inflammatory bowel disease, rheumatoid arthritis, osteoarthritis, Crohn's disease, Lyme disease, multiple sclerosis, Type 1 diabetes, psoriatic arthritis, restless legs syndrome (RLS), fibromyalgia, dermatitis herpetiformis, Sjdgren's syndrome, systemic lupus erythematosus, and gout.

In some embodiments, the angiogenic condition that can be treated with an anti-angiogenic composition of the invention is a respiratory disease such as asthma, chronic obstructive pulmonary disease (COPD), and atypical lymphoid disorders.

In some embodiments, the angiogenic condition that can be treated with an anti-angiogenic composition of the invention is an inflammatory disease of the genitourinary system disease such as endometriosis.

In some embodiments, the angiogenic condition that can be treated with an anti-angiogenic composition of the invention is an inflammatory disease of the digestive system, such as liver fibrosis.

In some embodiments, the angiogenic condition that can be treated with an anti-angiogenic composition of the invention is a neonatal or perinatal disease such as retinopathy of prematurity, infant respiratory distress syndrome, cyanosis, neonatal conjunctivitis, or intraventricular hemorrhage.

In some embodiments, the angiogenic condition that can be treated with an anti-angiogenic composition of the invention is a childhood disease such as Coat's disease, childhood Interstitial lung disease, Fifth disease, hand, foot, and mouth disease, croup, scarlet fever, impetigo, Kawasaki Disease, Reye's Syndrome, or diphtheria.

In some embodiments, the angiogenic condition that can be treated with an anti-angiogenic composition of the invention is an age-related disease such as age-related macular degeneration, or frontotemporal dementias like Pick disease.

In some embodiments, the angiogenic condition that can be treated with an anti-angiogenic composition of the invention is Gorham-Stout Disease, adrenoleukodystrophy, abetalipoproteinemia arthrogryposis, adrenomyeloneuropathy, antisynthetase syndrome, ancylostomiasis, Addison's Disease, amyloidosis, birdshot chorioretinopathy, malignant peripheral nerve sheath tumors, Moyamoya, sarcoidosis, systemic capillary leak syndrome, or plasma cell dyscrasia.

Many anti-angiogenic agents are known in the art and would be suitable for co-administration. Such agents include, for example, physiological agents such as growth factors (e.g., ANG-2, NK1, 2, 4 (HGF), transforming growth factor beta (TGF-β)), cytokines (e.g., interferons such as IFN-α, -β, -γ, platelet factor 4 (PF-4), PR-39), proteases (e.g., cleaved AT-III, collagen XVIII fragment (Endostatin)), HmwKallikrein-d5 plasmin fragment (Angiostatin), pro-thrombin-F1-2, TSP-1), protease inhibitors (e.g., tissue inhibitor of metalloproteases such as TIMP-1, -2, or -3; maspin; plasminogen activator-inhibitors such as PAI-1; pigment epithelium derived factor (PEDF)), Tumstatin (available through *ILEX*. Inc.), antibody products (e.g., the collagen-binding antibodies HUIV26, HU177, XL313; anti-VEGF: anti-integrin (e.g., Vitaxin, (Lxsys))), and glycosidases (e.g., heparinase-I or -II). Molecules that are antagonists to angiogenesis-associated antigens (including proteins and polypeptides) are also suitable and can include, but are not limited to, molecules directed against VEGF, VEGF receptor, EGFR, bFGF, PDGF-B, PD-ECGF, TGFs including TGF-.alpha., endoglin, Id proteins, various proteases, nitric oxide synthase, aminopeptidase, thrombospondins, k-ras, Wnt, cyclin-dependent kinases, microtubules, heat shock proteins, heparin-binding factors, synthases, collagen receptors, integrins, and surface proteoglycan NG2. "Chemical" or modified physiological agents known or believed to have anti-angiogenic potential include, for example, vinblastine, taxol, ketoconazole, thalidomide, dolestatin, combrestatin A, rapamycin (Guba, et al. 2002, Nature Med., 8: 128-135), CEP-7055 (available from Cephalon, Inc.), flavone acetic acid, Bay 12-9566 (Bayer Corp.), AG3340 (Agouron, Inc.). CGS. 27023A (Novartis), tetracylcne derivatives (e.g., COL-3 (Collagenix, Inc.)), Neovastat (Aeterna), BMS-275291 (Bristol-Myers Squibb), low dose 5-FU, low dose methotrexate (MTX), irsofladine, radicicol, cyclosporine, captopril, celecoxib, D45152-sulphated polysaccharide, cationic protein (Protarnine), cationic peptide-VEGF, Suramin (polysulphonated napthyl urea), compounds that interfere with the function or production of VEGF (e.g., SU5416 or SU6668 (Sugen), PTK787/ZK22584 (Novartis)), Distamycin A, Angiozyme (ribozyme), isoflavinoids, staurosporine derivatives, genistein, EMD121974 (Merck KcgaA), tyrphostins, isoquinolones, retinoic acid, carboxyamidotriazole, TNP-470, octreotide, 2-methoxyestradiol, aminosterols (e.g., squalamine), glutathione analogues (e.g., N-actey-L-cysteine), combretastatin A-4 (Oxigene), Eph receptor blocking agents (Nature, 414:933-938, 2001), Rh-Angiostatin, Rh-Endostatin (WO 01/93897), cyclic-RGD peptide, accutin-disintegrin, benzodiazepenes, humanized anti-avb3 Ab, Rh-PAI-2, amiloride, p-amidobenzamidine, anti-uPA ab, anti-uPAR Ab, L-phenylalanine-N-methylamides (e.g., Batimistat, Marimastat), AG3340, and minocycline. Many other suitable agents are known in the art and would suffice in practicing the present invention.

In some embodiments, the angiogenic condition can be treated with a pro-angiogenic composition of the invention. In some embodiments, provided herein are methods to prevent, inhibit or treat vascular disease by administering to a subject an effective amount of an AKIP1-disrupting peptide, the peptide comprising at least 85% amino acid sequence identity to one of the amino acid sequences selected from the group consisting of PEPTIDE4, PEPTIDE6, PEPTIDE8, PEPTIDE10, PEPTIDE11, PEPTIDE12 and PEPTIDE16, wherein the peptide induces (enhances) cell survival.

In some embodiments, provided herein are methods to prevent, inhibit or treat vascular disease by administering to a subject an effective amount of a nucleic acid encoding an AKIP1-disrupting peptide, the peptide comprising at least 85% amino acid sequence identity to one of the amino acid sequences selected from the group consisting of PEPTIDE4, PEPTIDE6, PEPTIDE8, PEPTIDE10, PEPTIDE11, PEPTIDE12 and PEPTIDE16, wherein the peptide induces (enhances) cell survival.

In some embodiments, the angiogenic condition that can be treated with a pro-angiogenic composition as described herein is an anti-angiogenic vascular condition or vascular disease including cardiovascular diseases such as ischemic heart disease, CAD (coronary heart disease), heart failure, myocardial infarction, congenital heart block, cardiomyopathy, pericarditis, endocarditis, arrhythmias and atrial fibrillations.

In some embodiments, the angiogenic condition that can be treated with a pro-angiogenic composition of the invention is a vascular or circulatory disease such as PAD (peripheral arterial disease), peripheral vascular disease, hypovolemia, deep vein thrombosis, atherosclerosis, hemorrhage, Raynaud's disease, and anemia.

In some embodiments, the angiogenic condition that can be treated with a pro-angiogenic composition of the invention is a neurological disease such as amyotrophic lateral sclerosis (ALS), Alzheimer's (AD), Parkinson's (PD), Hungtington's, diabetic neuropathy, cerebral autosomal dominant arteriopathy (CADASIL), stroke, Prion disease, cerebral ischemia, sleep apnea, and hypoxia during sleep.

In some embodiments, the angiogenic condition that can be treated with a pro-angiogenic composition of the invention is wound healing, stem cell related therapies including in wound angiogenesis, blood vessel repair, as well as reconstructive surgery, and regional perfusion deficits (e.g., limb, gut, renal ischemia).

In some embodiments, the angiogenic condition that can be treated with a pro-angiogenic composition of the invention is an endocrine or metabolic disease such as diabetes mellitus, impaired wound healing in diabetes, proliferative diabetic retinopathy, diabetic macular edema, renal failure, and diabetic nephropathy In some embodiments, the angiogenic condition that can be treated with a pro-angiogenic composition of the invention is a pulmonary disorder such as asthma, chronic obstructive pulmonary disease (COPD), and interstitial lung disease.

In some embodiments, the angiogenic condition that can be treated with a pro-angiogenic composition of the invention is a hypertensive disease such as primary hypertension or pulmonary hypertension.

In some embodiments, the angiogenic condition that can be treated with a pro-angiogenic composition of the invention is a respiratory disease such as acute respiratory distress syndrome In some embodiments, the angiogenic condition that can be treated with a pro-angiogenic composition of the invention is a glomerular disease such as renal failure.

In some embodiments, the angiogenic condition that can be treated with a pro-angiogenic composition of the invention is a genitourinary system disease including male infertility and erectile dysfunction.

In some embodiments, the angiogenic condition that can be treated with a pro-angiogenic composition of the invention is a disease of the digestive system such as nonalcoholic steatohepatitis.

In some embodiments, the angiogenic condition that can be treated with a pro-angiogenic composition of the invention is a newborn or prenatal condition such as fetal hypoxia, respiratory distress syndrome, bronchopulmonary dysplasia, sudden infant death syndrome (SIDS), perinatal Asphyxia, necrotizing enterocolitis, patent ductus arteriosus, or erythroblastosis (blue baby syndrome).

In some embodiments, the angiogenic condition that can be treated with a pro-angiogenic composition of the invention is an age-related disease such as Parkinson's, Presbycusis and age-related hearing loss, osteoporosis, vascular dementia, Lewy Body dementia, or ataxia.

In some embodiments, the angiogenic condition that can be treated with a pro-angiogenic composition of the invention is common variable immunodeficiency or neonatal respiratory distress syndrome.

In some embodiments, the angiogenic condition that can be treated with a pro-angiogenic composition of the invention is preeclampsia or a congenital circulatory abnormality (e.g., Tetralogy of Fallot).

Examples of vascular conditions or vascular diseases which may be prevented or treated using the disclosed compositions include but are not limited to atherosclerosis, preeclampsia, peripheral vascular disease, erectile dysfunction, cancers, renal failure, heart disease, stroke, maternal hypoxia (e.g., placental hypoxia, preeclampsia), abnormal pregnancy, peripheral vascular disease (e.g., arteriosclerosis), transplant accelerated arlteriosclerosis, deep vein thrombosis, erectile dysfunction, cancers, renal failure, stroke, heart disease, sleep apnea, hypoxia during sleep, female sexual dysfunction, fetal hypoxia, smoking, anemia, hypovolemia, vascular or circulatory conditions which increase risk of metastasis or tumor progression, hemorrhage, hypertension, diabetes, vasculopathologies, surgery (e.g., per-surgical hypoxia, post-operative hypoxia), Raynaud's disease, endothelial dysfunction, regional perfusion deficits (e.g., limb, gut, renal ischemia), myocardial infarction, stroke, thrombosis, frost bite, decubitus ulcers, asphyxiation, poisoning (e.g., carbon monoxide, heavy metal), altitude sickness, pulmonary hypertension, sudden infant death syndrome (SIDS), asthma, chronic obstructive pulmonary disease (COPD), congenital circulatory abnormalities (e.g., Tetralogy of Fallot) and Erythroblastosis (blue baby syndrome). In one embodiment, the compositions of the invention are employed to prevent, inhibit or treat stroke, atherosclerosis, acute coronary syndromes including unstable angina, thrombosis and myocardial infarction, plaque rupture, both primary and secondary (in-stent) restenosis in coronary or peripheral arteries, transplantation-induced sclerosis, peripheral limb disease, intermittent claudication and diabetic complications (including ischemic heart disease, peripheral artery disease, congestive heart failure, retinopathy, neuropathy and nephropathy), or thrombosis.

Formulations and Dosages

The disclosed compositions can be formulated as pharmaceutical compositions and administered to a mammalian host, such as a human patient in a variety of forms adapted to the chosen route of administration, e.g., orally or parenterally, by intravenous, intramuscular, topical or subcutaneous routes.

The disclosed compositions may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral administration, the peptides or fusions thereof, or nucleic acid encoding the peptide or fusion, may be combined with one or more excipients and used in the form of ingestible tablets, buccal tablets, troches, capsules, elixirs, suspensions, syrups, wafers, and the like. Such compositions and preparations should contain at least 0.1% of active agent. The percentage of the compositions and preparations may, of course, be varied and may conveniently be between about 2 to about 60% of the weight of a given unit dosage form. The amount of active agent in such useful compositions is such that an effective dosage level will be obtained.

Tablets, troches, pills, capsules, and the like may also contain binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The disclosed compositions may also be administered intravenously or intraperitoneally by infusion or injection. Solutions of the peptides or fusions thereof, or nucleic acid encoding the peptide or fusion or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, isotonic agents, for example, sugars, buffers or sodium chloride are included. Prolonged absorption of the injectable compositions can be brought about by the use in the compositions of agents delaying absorption, for example, aluminum monostearate and gelatin.

Sterile injectable solutions are prepared by incorporating the active agent in the required amount in the appropriate solvent with various of the other ingredients enumerated above, as required, followed by filter sterilization. In the case of sterile powders for the preparation of sterile injectable solutions, the methods of preparation include vacuum drying and the freeze drying techniques, which yield a powder of the active ingredient plus any additional desired ingredient present in the previously sterile-filtered solutions.

For topical administration, the disclosed compositions may be applied in pure form, e.g., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the disclosed compositions can be determined by comparing their in vitro activity and in vivo activity in animal models. Methods for the extrapolation of effective dosages in mice, and other animals, to humans are known to the art; for example, see U.S. Pat. No. 4,938,949.

Generally, the concentration of the peptides or fusions thereof, or nucleic acid encoding the peptide or fusion, in a liquid composition, such as a lotion, may be from about 0.1-25 wt-%, e.g., from about 0.5-10 wt-%. The concentration in a semi-solid or solid composition such as a gel or a powder may be about 0.1-5 wt-%, e.g., about 0.5-2.5 wt-%.

The amount of the disclosed compositions required for use alone or with other agents will vary with the route of administration, the nature of the condition being treated and the age and condition of the patient and will be ultimately at the discretion of the attendant physician or clinician.

The disclosed compositions may be conveniently administered in unit dosage form; for example, containing 5 to 1000 mg, conveniently 10 to 750 mg, or conveniently 50 to 500 mg of active ingredient per unit dosage form.

In general, however, a suitable dose may be in the range of from about 0.5 to about 100 mg/kg, e.g., from about 10 to about 75 mg/kg of body weight per day, such as 3 to about 50 mg per kilogram body weight of the recipient per day, for example in the range of 6 to 90 mg/kg/day, e.g., in the range of 15 to 60 mg/kg/day.

EXEMPLARY EMBODIMENTS

A1. A pharmaceutical composition comprising an effective amount of an AKIP1-disrupting peptide, the peptide comprising at least 85% amino acid sequence identity to one of the amino acid sequences selected from the group consisting of PEPTIDE1, PEPTIDE2, PEPTIDE3, PEPTIDE4, PEPTIDE5. PEPTIDE7, PEPTIDE8, PEPTIDE9, PEPTIDE10, PEPTIDE11, PEPTIDE13, PEPTIDE14, PEPTIDE15, PEPTIDE16, PEPTIDE17 and PEPTIDE18, wherein the peptide induces apoptosis or cell death, or alters angiogenesis.

A2. The pharmaceutical composition of embodiment A1, comprising an effective amount of an AKIP1-disrupting peptide, the peptide comprising at least 90%, at least 92%, at least 94%, at least 95%, at least 96%, at least 97%, at least 98%, or at least 99% amino acid sequence identity to one of the amino acid sequences selected from the group consisting of PEPTIDE1, PEPTIDE2, PEPTIDE3, PEPTIDE4, PEPTIDE5, PEPTIDE7, PEPTIDE8, PEPTIDE9, PEPTIDE10, PEPTIDE11. PEPTIDE13, PEPTIDE14, PEPTIDE15, PEPTIDE16, PEPTIDE17 and PEPTIDE18, wherein the peptide induces apoptosis or cell death, or alters angiogenesis.

A3. The pharmaceutical composition of embodiment A1 or A2, comprising a fusion.

A4. The pharmaceutical composition of embodiment A3, wherein the fusion comprises a tissue-penetrating peptide (TPP) or cell-penetrating peptide (CPP) sequence.

A5. The pharmaceutical composition of embodiment A4, wherein the tissue-penetrating peptide (TPP) or cell-penetrating peptide (CPP) sequence is selected from the group consisting of: amphipathic, cationic, hydrophobic and anionic type.

A6. The pharmaceutical composition of embodiment A4, comprising MAKRGARSTA (SEQ ID NO:58).

A7. The pharmaceutical composition of embodiment A4, wherein the CPP is selected from the group consisting of: RVG29, CDX, Angiopep-2, ApoB (3371-3409), ApoE (159-167)2, Peptide-22, TfR B6, T7, THR, Leptin 30, Apamin, ApOO, MiniAp-4, GSH, G23, g7, Tat(47-57), SynB1, Diketopiperazine, Phenylproline oligomer, PepH3, and PepNeg.

A8. The pharmaceutical composition of any of the embodiments A1 to A7, comprising a non-antibody scaffold.

A9. The pharmaceutical composition of embodiment A8, wherein the non-antibody scaffold is selected from the group consisting of: adnectins, affibodies, affilins, anticalins, atrimers, avimers bicyclic peptides, Centyrin, Cys-knots, DARPins, fynomers, Kunitz domain, O-bodies, pronectins, and Tn3.

A10. The pharmaceutical composition of any of the embodiments A1 to A9, comprising a salt of the carboxyl group.

A11. The pharmaceutical composition of any of the embodiments A1 to A10, comprising an N- or C-terminal modification.

A12. The pharmaceutical composition of any of the embodiments A1 to A11, comprising an amino acid substitution.

A13. The pharmaceutical composition of embodiment A12, wherein the amino acid substitution is selected from the group consisting of: phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, alpha-methyl-alanine, para-benzoyl-phenylalanine, phenylglycine, propargylglycine, sarcosine, epsilon-N,N,N-trimethyllysine, epsilon-N-acetyllysine, N-acetylserine, N-formylmethionine, 3-methylhistidine, 5-hydroxylysine, and omega-N-methylarginine.

A14. The pharmaceutical composition of any of the embodiments A1 to A13, wherein the peptide is cyclic.

A15. The pharmaceutical composition of any of the embodiments A1 to A13, wherein the peptide is branched.

A16. The pharmaceutical composition of embodiment A1, wherein the peptide comprises a peptidomimetic.

A17. The pharmaceutical composition of any of the embodiments A1 to A16, wherein the peptide is conjugated to bovine serum albumin, ovalbumin, or keyhole limpet hemocyanin.

A18. The pharmaceutical composition of any of the embodiments A1 to A17, wherein the peptide is conjugated to polyethylene glycol.

A19. The pharmaceutical composition of any of the embodiments A1 to A18, wherein the composition is formulated as a pro-drug.

B1. A pharmaceutical composition comprising an effective amount of a nucleic acid encoding an AKIP1-disrupting peptide, the peptide comprising at least 85% amino acid sequence identity to one of the amino acid sequences selected from the group consisting of PEPTIDE1, PEPTIDE2, PEPTIDE3, PEPTIDE4, PEPTIDE5, PEPTIDE7, PEPTIDE8, PEPTIDE9, PEPTIDE10, PEPTIDE11, PEPTIDE13, PEPTIDE14, PEPTIDE15, PEPTIDE16, PEPTIDE17 and PEPTIDE18, wherein the peptide induces apoptosis or cell death, or alters angiogenesis.

B2. The pharmaceutical composition of embodiment B1, comprising a delivery vector.

B3. The pharmaceutical composition of embodiment B2, wherein the delivery vector comprises a plasmid vector.

B4. The pharmaceutical composition of embodiment B2, wherein the delivery vector comprises a viral vector.

B5. The pharmaceutical composition of embodiment 84, wherein the viral vector is selected from the group consisting of: recombinant adenovirus, retrovirus, lentivirus, herpesvirus, poxvirus, papilloma virus, and adeno-associated virus.

B6. The pharmaceutical composition of embodiment B1, comprising a liposome.

B7. The pharmaceutical composition of embodiment B6, wherein the liposome is selected from the group consisting of: DOSPA/DOPE, DOGS/DOPE, DMRIE/DOPE and DOTMA/DOPE.

B8. The pharmaceutical composition of embodiment B1, comprising a carrier system for cargo delivery.

B9. The pharmaceutical composition of embodiment B8, wherein the carrier system for cargo delivery is selected from the group consisting of: a polymer matrix, a polymeric nanoparticle, a nanoworm, a hydrogel, a phosphorodiamidate morpholino oligomer, and a peptide nucleic acid.

C1. A method for to prevent, inhibit or treat an angiogenic disorder by administering to a subject an effective amount of a pharmaceutical composition of any of the embodiments A1-A19 or B1-B9.

C2. The method of embodiment C1, wherein the angiogenic disorder comprises cancer.
C3. The method of embodiment C2, wherein the cancer is a solid tumor cancer.
C4. The method of embodiment C3, wherein the solid tumor cancer is a cancer of an organ selected from the group consisting of: nervous system, ovary, breast, lung, thyroid, lymph node, kidney, ureter, bladder, teste, prostate, skin, bone, skeletal muscle, bone marrow, stomach, esophagus, small bowel, colon, rectum, pancreas, liver, smooth muscle, ear, eye, nasopharynx, oropharynx, salivary gland, blood vessels, and heart.
C5. The method of embodiment C4, wherein the cancer comprises brain cancer.
C6. The method of embodiment C4, wherein the cancer comprises cancer of the nervous system and selected from the group consisting of: glioblastoma multiforme, neuroma, anaplastic astrocytoma, neuroblastoma, glioma, astrocytoma, meningioma, pituitary adenoma, primary CNS lymphoma, medulloblastoma, ependymoma, sarcoma, oligodendroglioma, medulloblastoma, spinal cord tumor, and schwannoma.
C7. The method of embodiment C4, wherein the cancer comprises ovarian cancer.
C8. The method of embodiment C7, wherein the cancer is selected from the group consisting of: ovarian epithelial carcinoma and germ cell tumor.
C9. The method of embodiment C4, wherein the cancer comprises breast cancer.
C10. The method of embodiment C9, wherein the cancer is selected from the group consisting of: ductal carcinoma in situ (DCIS), infiltrating ductal carcinoma, invasive ductal carcinoma, infiltrating lobular carcinoma, and invasive lobular carcinoma.
C11. The method of embodiment C4, wherein the cancer comprises lung cancer.
C12. The method of embodiment C11, wherein the cancer is selected from the group consisting of: small cell lung cancer, non-small cell lung cancer, metastatic lung cell cancer, and lung lymphatic cancer.
C13. The method of embodiment C4, wherein the cancer comprises thyroid cancer.
C14. The method of embodiment C13, wherein the cancer is selected from the group consisting of: papillary thyroid cancer, mixed papillary/follicular thyroid cancer, follicular thyroid cancer, Hurthle cell thyroid cancer, medullary thyroid cancer, and anaplastic thyroid cancer.
C15. The method of embodiment C4, wherein the cancer comprises kidney cancer.
C16. The method of embodiment C15, wherein the cancer is selected from the group consisting of: renal cell carcinoma, transitional cell carcinoma, Wilms tumor, and renal sarcoma.
C17. The method of embodiment C4, wherein the cancer comprises bladder cancer.
C18. The method of embodiment C17, wherein the cancer is selected from the group consisting of: squamous cell carcinoma and adenocarcinoma.
C19. The method of embodiment C4, wherein the cancer comprises skin cancer.
C20. The method of embodiment 019, wherein the cancer is selected from the group consisting of: squamous cell carcinoma, Kaposi's sarcoma, malignant melanoma, Merkel cell skin cancer, and non-melanoma skin cancer.
C21. The method of embodiment C4, wherein the cancer comprises bone cancer.
C22. The method of embodiment C21, wherein the cancer is selected from the group consisting of: osteosarcoma, chondrosarcoma, and the Ewing Sarcoma Family of Tumors (ESFTs).
C23. The method of embodiment C4, wherein the cancer comprises pancreatic cancer.
C24. The method of embodiment C23, wherein the cancer is selected from the group consisting of: exocrine pancreatic cancer and endocrine pancreatic cancer.
C25. The method of embodiment C24, wherein the cancer comprises exocrine pancreatic cancer and is selected from the group consisting of: adenocarcinoma, acinar cell carcinoma, adenosquamous carcinoma, colloid carcinoma, undifferentiated carcinoma with osteoclast-like giant cells, hepatoid carcinoma, intraductal papillary-mucinous neoplasm, mucinous cystic neoplasm, pancreatoblastoma, serous cystadenoma, signet ring cell carcinoma, pseuodpapillary tumor, pancreatic ductal carcinoma, and undifferentiated carcinoma.
C26. The method of embodiment C24, wherein the cancer comprises endocrine pancreatic cancer and is selected from the group consisting of: insulinoma and glucagonoma.
C27. The method of embodiment C4, wherein the cancer comprises liver cancer.
C28. The method of embodiment C27, wherein the cancer is selected from the group consisting of: hepatocellular carcinoma, cholangiocarcinoma, and mixed hepatocellular cholangiocarcinoma.
C29. The method of embodiment C4, wherein the cancer comprises eye cancer.
C30. The method of embodiment C29, wherein the cancer is selected from the group consisting of: intraocular melanoma and retinoblastoma.
C31. The method of embodiment C4, wherein the cancer comprises blood vessel cancer.
C32. The method of embodiment C31, wherein the cancer comprises hemangioma.
C33. The method of embodiment C3, wherein the cancer is selected from the group consisting of: von Hippel-Lindau disease, Castleman's disease, lymphadenopathy, X-linked lymphoproliferative disorder, and Non-Hodgkin's Lymphoma.
C34. The method of any of the embodiments of C1 to C33, further comprising a pharmaceutically effective anti-cancer agent.
C35. The method of embodiment C1, wherein the angiogenic disorder comprises an infectious disease.
C36. The method of embodiment C35, wherein the infectious disease is selected from the group consisting of: cholera, typhoid, tuberculosis, human immunodeficiency virus (HIV), *Leishmania major* infection, herpetic stromal keratitis, dengue hemorrhagic fever, dengue shock syndrome, hantavirus pulmonary syndrome, hemorrhagic fever with renal syndrome, pustular skin disease, smallpox, dracunculiasis, Human African trypanosomiasis, leishmaniasis, leprosy, pneumonia, HPV, gonorrhea, syphilis, anthrax, mononucleosis, viral conjunctivitis, lymphatic filariasis, onchocerciasis, schistosomiasis, soil-transmitted helminthiases, trachoma, acute viral encephalitis, West Nile fever, Zika, malaria, Japanese encephalitis, tularemia, Chagas, sandfly fever, plague, rickettsiosis, influenza, cervicovaginal infection, and decubitus ulcers.
C37. The method of embodiment C1, wherein the angiogenic disorder is selected from the group consisting of: neutropenia, ocular neovascularization, retinal vascular disease, or neovascular glaucoma.

C38. The method of embodiment C1, wherein the angiogenic disorder is selected from the group consisting of: meningitis, encephalitis, and sleep apnea.

C39. The method of embodiment C1, wherein the angiogenic disorder is selected from the group consisting of: obesity, gestational diabetes mellitus, proliferative diabetic retinopathy, diabetic macular edema, and familial hypercholesterolemia.

C40. The method of embodiment C1, wherein the angiogenic disorder is selected from the group consisting of: cutaneous inflammation, psorisis, phototoxicity, chronic skin inflammation, atopic dermatitis, eczema, and polymyositis/dermatomyositis.

C41. The method of embodiment C1, wherein the angiogenic disorder comprises a chronic inflammatory disease.

C42. The method of embodiment C40, wherein the chronic inflammatory disease is selected from the group consisting of: inflammatory bowel disease, rheumatoid arthritis, osteoarthritis, Crohn's disease, Lyme disease, multiple sclerosis, Type 1 diabetes, psoriatic arthritis, restless legs syndrome (RLS), fibromyalgia, dermatitis herpetiformis, Sjögren's syndrome, systemic lupus erythematosus, and gout.

C43. The method of embodiment C1, wherein the angiogenic disorder is selected from the group consisting of: asthma, chronic obstructive pulmonary disease (COPD), and atypical lymphoid disorder.

C44. The method of embodiment C1, wherein the angiogenic disorder comprises endometriosis.

C45. The method of embodiment C1, wherein the angiogenic disorder comprises liver fibrosis.

C46. The method of embodiment C1, wherein the angiogenic disorder is selected from the group consisting of: retinopathy of prematurity, infant respiratory distress syndrome, cyanosis, neonatal conjunctivitis, and intraventricular hemorrhage.

C47. The method of embodiment C1, wherein the angiogenic disorder is selected from the group consisting of: Coat's disease, childhood Interstitial lung disease, Fifth disease, hand, foot, and mouth disease, croup, scarlet fever, impetigo, Kawasaki Disease, Reye's Syndrome, or diphtheria.

C48. The method of embodiment C1, wherein the angiogenic disorder is selected from the group consisting of: age-related macular degeneration and frontotemporal dementia.

C49. The method of embodiment C1, wherein the angiogenic disorder is selected from the group consisting of: Gorham-Stout Disease, adrenoleukodystrophy, abetalipoproteinemia arthrogryposis, adrenomyeloneuropathy, antisynthetase syndrome, ancylostomiasis, Addison's Disease, amyloidosis, birdshot chorioretinopathy, malignant peripheral nerve sheath tumors, Moyamoya, sarcoidosis, systemic capillary leak syndrome, or plasma cell dyscrasia.

D1. A pharmaceutical composition comprising an effective amount of an AKIP1-disrupting peptide, the peptide comprising at least 85% amino acid sequence identity to one of the amino acid sequences selected from the group consisting of PEPTIDE4, PEPTIDE6, PEPTIDE8, PEPTIDE10, PEPTIDE11. PEPTIDE12 and PEPTIDE16, wherein the peptide induces cell survival.

D2. The pharmaceutical composition of embodiment D1, comprising an effective amount of an AKIP1-disrupting peptide, the peptide comprising at least 90%, at least 92%, at least 94%, at least 95%, at least 96%, at least 97%, at least 98%, or at least 99% amino acid sequence identity to one of the amino acid sequences selected from the group consisting of PEPTIDE4, PEPTIDE6, PEPTIDE8, PEPTIDE10, PEPTIDE11, PEPTIDE12 and PEPTIDE16, wherein the peptide induces cell survival.

D3. The pharmaceutical composition of embodiment D1 or D2, comprising a fusion.

D4. The pharmaceutical composition of embodiment 04, wherein the fusion comprises a tissue-penetrating peptide (TPP) or cell-penetrating peptide (CPP) sequence.

D5. The pharmaceutical composition of embodiment D4, wherein the tissue-penetrating peptide (TPP) or cell-penetrating peptide (CPP) sequence is selected from the group consisting of: amphipathic, cationic, hydrophobic and anionic type.

D6. The pharmaceutical composition of embodiment 04, comprising MAKRGARSTA (SEQ ID NO:58).

D07. The pharmaceutical composition of embodiment D4, wherein the CPP is selected from the group consisting of: RVG29, CDX, Angiopep-2, ApoB (3371-3409), ApoE (159-167)2, Peptide-22, TfR B6, T7, THR, Leptin 30, Apamin, ApOO, MiniAp-4, GSH, G23, g7, Tat(47-57), SynB1, Diketopiperazine, Phenylproline oligomer, PepH3, and PepNeg.

D8. The pharmaceutical composition of any of the embodiments D1 to 07, comprising a non-antibody scaffold.

D9. The pharmaceutical composition of embodiment D8, wherein the non-antibody scaffold is selected from the group consisting of: adnectin, affibody, affilin, anticalin, atrimer, avimer, bicyclic peptide, Centyrin, Cys-knot, DARPin, fynomer, Kunitz domain, O-body, pronectin, and Tn3.

D10. The pharmaceutical composition of any of the embodiments D1 to D9, comprising a salt of the carboxyl group.

D11. The pharmaceutical composition of any of the embodiments D1 to D10, comprising an N- or C-terminal modification.

D12. The pharmaceutical composition of any of the embodiments D1 to D11, wherein the peptide comprises an amino acid substitution relative to one of SEQ ID Nos. 1-25.

D13. The pharmaceutical composition of embodiment D12, wherein the amino acid substitution is selected from the group consisting of: phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, alpha-methyl-alanine, para-benzoyl-phenylalanine, phenylglycine, propargylglycine, sarcosine, epsilon-N,N,N-trimethyllysine, epsilon-N-acetyllysine, N-acetylserine, N-formylmethionine, 3-methylhistidine, 5-hydroxylysine, and omega-N-methylarginine.

D14. The pharmaceutical composition of any of the embodiments D1 to D13, wherein the peptide is cyclic.

D15. The pharmaceutical composition of any of the embodiments D1 to D13, wherein the peptide is branched.

D16. The pharmaceutical composition of embodiment D1, wherein the peptide comprises a peptidomimetic.

D17. The pharmaceutical composition of any of the embodiments D1 to D16, wherein the peptide is conjugated to bovine serum albumin, ovalbumin, or keyhole limpet hemocyanin.

D18. The pharmaceutical composition of any of the embodiments D1 to D17, wherein the peptide is conjugated to polyethylene glycol.

D19. The pharmaceutical composition of any of the embodiments D1 to D18, wherein the composition is formulated as a pro-drug.

E1. A pharmaceutical composition comprising an effective amount of a nucleic acid encoding an AKIP1-disrupting peptide, the peptide comprising at least 85% amino acid sequence identity to one of the amino acid sequences selected from the group consisting of PEPTIDE4, PEPTIDE6, PEPTIDE8, PEPTIDE10, PEPTIDE11, PEPTIDE12 and PEPTIDE16, wherein the peptide induces cell survival.

E2. The pharmaceutical composition of embodiment E1, comprising a delivery vector.

E3. The pharmaceutical composition of embodiment E2, wherein the delivery vector comprises a plasmid vector.

E4. The pharmaceutical composition of embodiment E2, wherein the delivery vector comprises a viral vector.

E5. The pharmaceutical composition of embodiment E4, wherein the viral vector is selected from the group consisting of: recombinant adenovirus, retrovirus, lentivirus, herpesvirus, poxvirus, papilloma virus, and adeno-associated virus.

E6. The pharmaceutical composition of embodiment E1, comprising a liposome.

E7. The pharmaceutical composition of embodiment E6, wherein the liposome is selected from the group consisting of: DOSPA/DOPE, DOGS/DOPE, DMRIE/DOPE and DOTMA/DOPE.

E8. The pharmaceutical composition of embodiment E1, comprising a carrier system for cargo delivery.

E9. The pharmaceutical composition of embodiment E8, wherein the carrier system for cargo delivery is selected from the group consisting of: a polymer matrix, a polymeric nanoparticle, a nanoworm, a hydrogel, a phosphorodiamidate morpholino oligomer, and a peptide nucleic acid.

F1. A method to prevent, inhibit or treat an angiogenic disorder by administering to a subject an effective amount of a pharmaceutical composition of any of the embodiments D1-D19 or E1-E9.

F2. The method of embodiment F1, wherein the angiogenic disorder comprises a vascular or circulatory disease.

F3. The method of embodiment F2, wherein the vascular or circulatory disease comprises a cardiovascular disease.

F4. The method of embodiment F3, wherein the cardiovascular disease is selected from the group consisting of: ischemic heart disease. CAD (coronary heart disease), heart failure, myocardial infarction, congenital heart block, cardiomyopathy, pericarditis, endocarditis, arrhythmia, and atrial fibrillation.

F5. The method of embodiment F2, wherein the vascular or circulatory disease is selected from the group consisting of: PAD (peripheral arterial disease), peripheral vascular disease, hypovolemia, deep vein thrombosis, artherosclerosis, hemorrhage, Raynaud's disease, and anemia.

F6. The method of embodiment F1, wherein the angiogenic disorder comprises a neurological disease.

F7. The method of embodiment F6, wherein the neurological disease is selected from the group consisting of: amyotrophic lateral sclerosis (ALS), Alzheimer's (AD), Parkinson's (PD), Hungtington's, diabetic neuropathy, cerebral autosomal dominant arteriopathy (CADASIL), stroke, Prion disease, cerebral ischemia, sleep apnea, and hypoxia during sleep.

F8. The method of embodiment F1, wherein the angiogenic disorder is selected from the group consisting of: wound healing, stem cell related therapy, blood vessel repair, reconstructive surgery, and regional perfusion deficit.

F9. The method of embodiment F1, wherein the angiogenic disorder comprises an endocrine or metabolic disease.

F10. The method of embodiment F9, wherein the endocrine or metabolic disease is selected from the group consisting of: diabetes mellitus, impaired wound healing in diabetes, proliferative diabetic retinopathy, diabetic macular edema, renal failure, and diabetic nephropathy.

F11. The method of embodiment F1, wherein the angiogenic disorder comprises a pulmonary disorder.

F12. The method of embodiment F11, wherein the pulmonary disorder is selected from the group consisting of: asthma, chronic obstructive pulmonary disease (COPD), and interstitial lung disease.

F13. The method of embodiment F1, wherein the angiogenic disorder comprises a hypertensive disease.

F14. The method of embodiment F13, wherein the hypertensive disease is selected from the group consisting of: primary hypertension and pulmonary hypertension.

F15. The method of embodiment F1, wherein the angiogenic disorder comprises a respiratory disease.

F16. The method of embodiment F15, wherein the respiratory disease comprises acute respiratory distress syndrome.

F17. The method of embodiment F1, wherein the angiogenic disorder comprises a glomerular disease.

F18. The method of embodiment F17, wherein the glomerular disease comprises renal failure.

F19. The method of embodiment F1, wherein the angiogenic disorder comprises a genitourinary system disease.

F20. The method of embodiment F19, wherein the genitourinary system disease is selected from the group consisting of: male infertility and erectile dysfunction.

F21. The method of embodiment F1, wherein the angiogenic disorder comprises a disease of the digestive system.

F22. The method of embodiment F21, wherein the disease of the digestive system comprises nonalcoholic steatohepatitis.

F23. The method of embodiment F1, wherein the angiogenic disorder is selected from the group consisting of: fetal hypoxia, respiratory distress syndrome, bronchopulmonary dysplasia, sudden infant death syndrome (SIDS), perinatal Asphyxia, necrotizing enterocolitis, patent ductus arteriosus, and erythroblastosis (blue baby syndrome).

F24. The method of embodiment F1, wherein the angiogenic disorder is selected from the group consisting of: Parkinson's. Presbycusis and age related hearing loss, osteoporosis, vascular dementia, Lewy Body dementia, and ataxia.

F25. The method of embodiment F1, wherein the angiogenic disorder is selected from the group consisting of: preeclampsia and congenital circulatory abnormality.

G1. A mammalian host cell, the genome of which is augmented by a vector comprising nucleic acid encoding an AKIP1-disrupting peptide, the peptide comprising at least 85% amino acid sequence identity to one of the amino acid sequences selected from the group consisting of PEPTIDE1, PEPTIDE2, PEPTIDE3, PEPTIDE4, PEPTIDE5, PEPTIDE7, PEPTIDE8, PEPTIDE9, PEPTIDE10, PEPTIDE11, PEPTIDE13, PEPTIDE14, PEPTIDE15, PEPTIDE16, PEPTIDE17 and PEPTIDE18, wherein the peptide induces apoptosis or cell death, or alters angiogenesis.

G2. A mammalian host cell, the genome of which is augmented by a vector comprising nucleic acid encoding an AKIP1-disrupting peptide, the peptide comprising at least 85% amino acid sequence identity to one of the amino acid sequences selected from the group consisting of PEPTIDE4, PEPTIDE6, PEPTIDE8, PEPTIDE10, PEPTIDE11, PEPTIDE12 and PEPTIDE16, wherein the peptide induces or enhances cell survival.

The invention will be described by the following non-limiting examples.

Example 1

Figure 9:
FIG. 9 shows the general design of peptides. A cell penetrating peptide was attached to the N-terminus of the ADPs for delivery and a fluorescent tag was attached at the C-terminus. TPP: tumor penetrating peptide (LinTT1) (Sharma et al., Nano. Lett., 17:1356 (2017)); CTP: cardiac penetrating peptide (Feinstein et al., Circ., 134:A18007 (2016)). SNAP tag was attached to C-terminus to visualize the peptides in cells. A TEV site was engineered between Adip and SNAP.
Figure 10B:
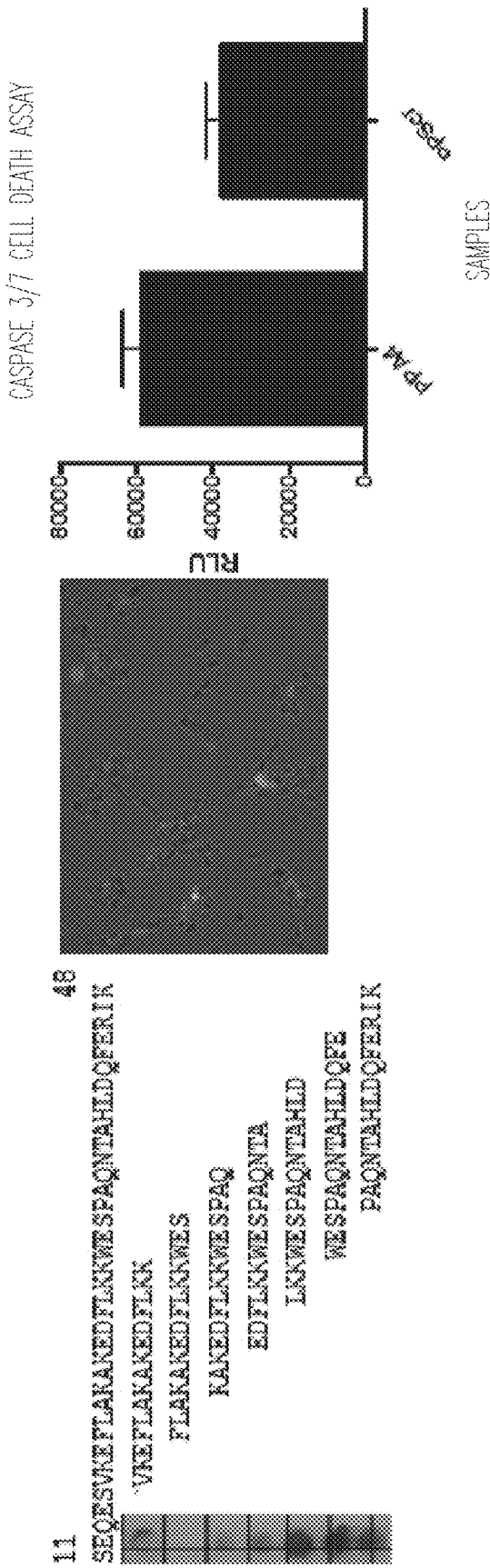
Figure 10C:
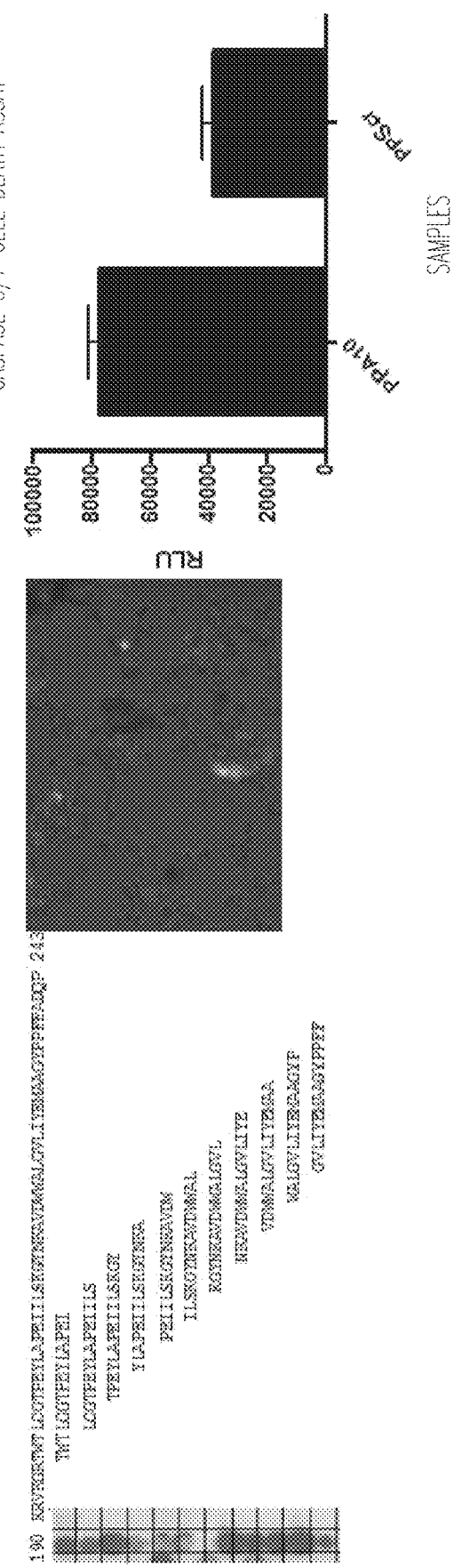
Figure 11B:
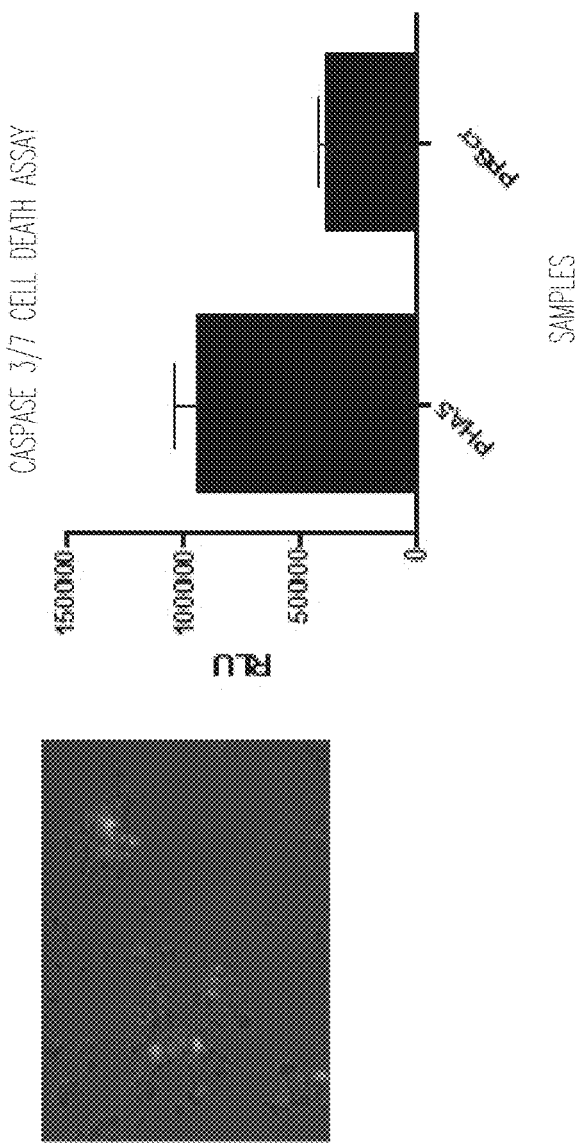
Figure 12A:
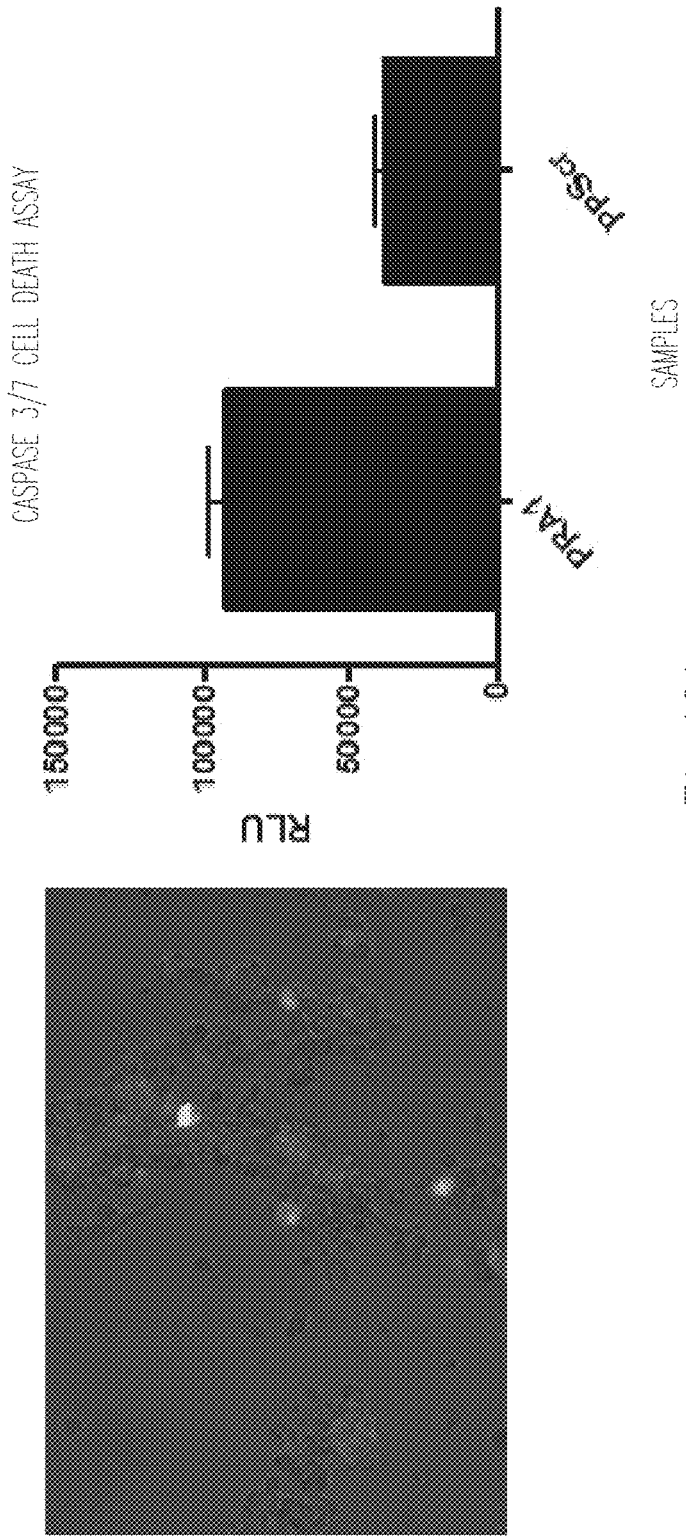
FIGS. 12A-C show the sequences mapped, peptide blots, imaging to show expression and cell death assays for these p65 (RELA) peptides. A) PRA1 (PEPTIDE14) (SEQ IDNO: 14), B) PRA8 (PEPTIDE8) (SEQ IDNO:8), C) PRA9 (SEQ ID Nos:33 and 37-45).
Figure 12B:
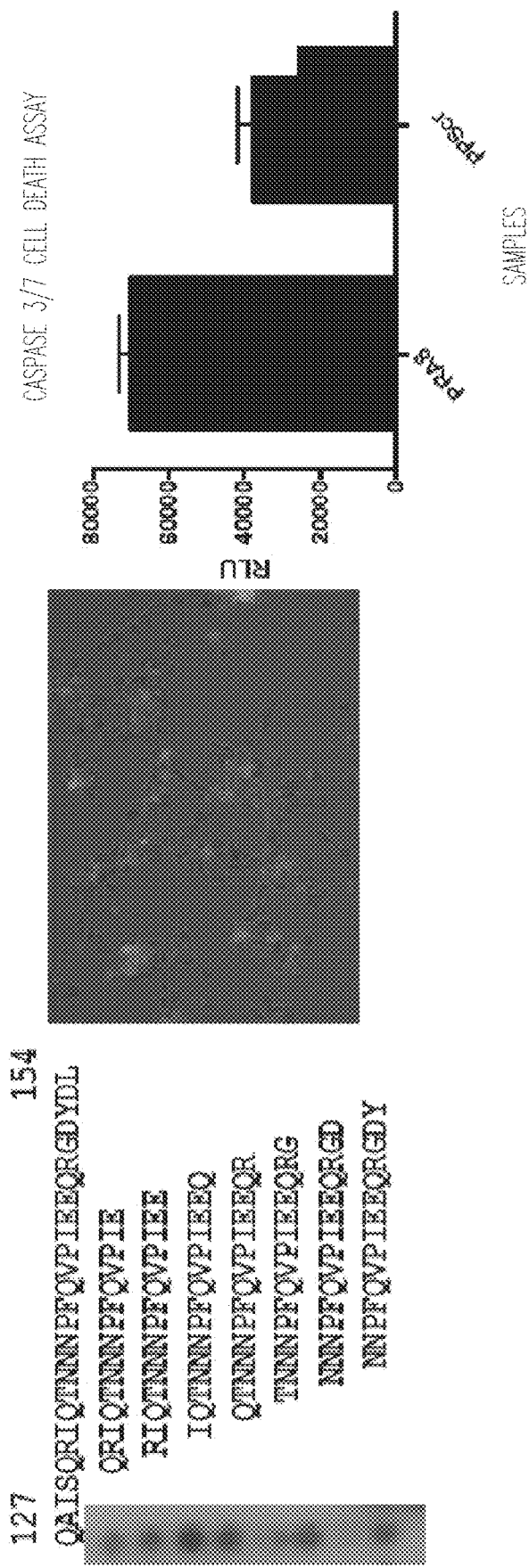
Figure 12C:
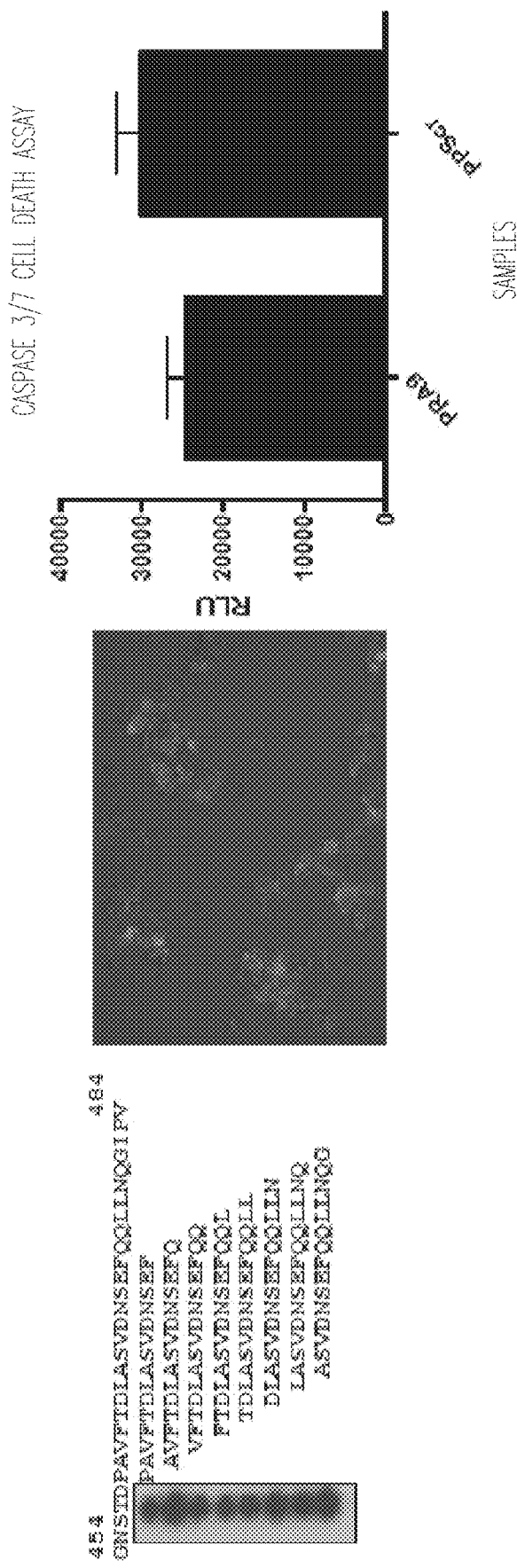
Figure 13A:
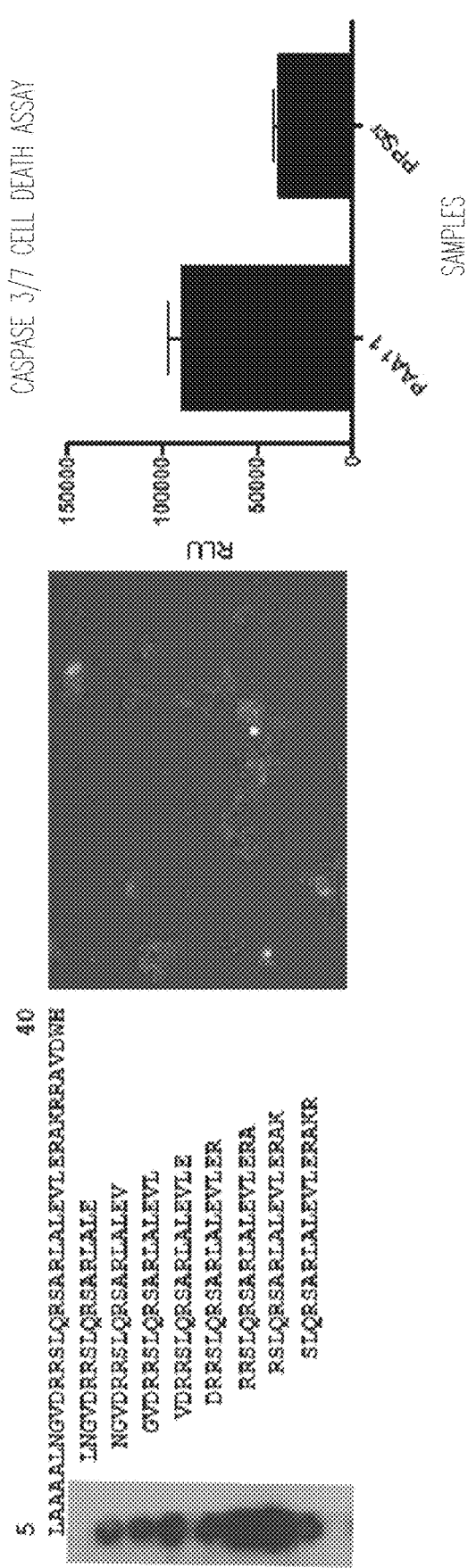
FIGS. 13A-D show the sequences mapped, peptide blots, imaging to show expression and cell death assays for these HSP-70 peptides. A) PAA1-1 (PEPTIDE11 (SEQ ID NO:11), B) PPA1-3 (PEPTIDE15) (SEQ ID NO:15), C) PAR1 (PEPTIDE19), D) Paint 1 (PEPTIDE7) (SEQ ID NO:7).
Figure 13B:
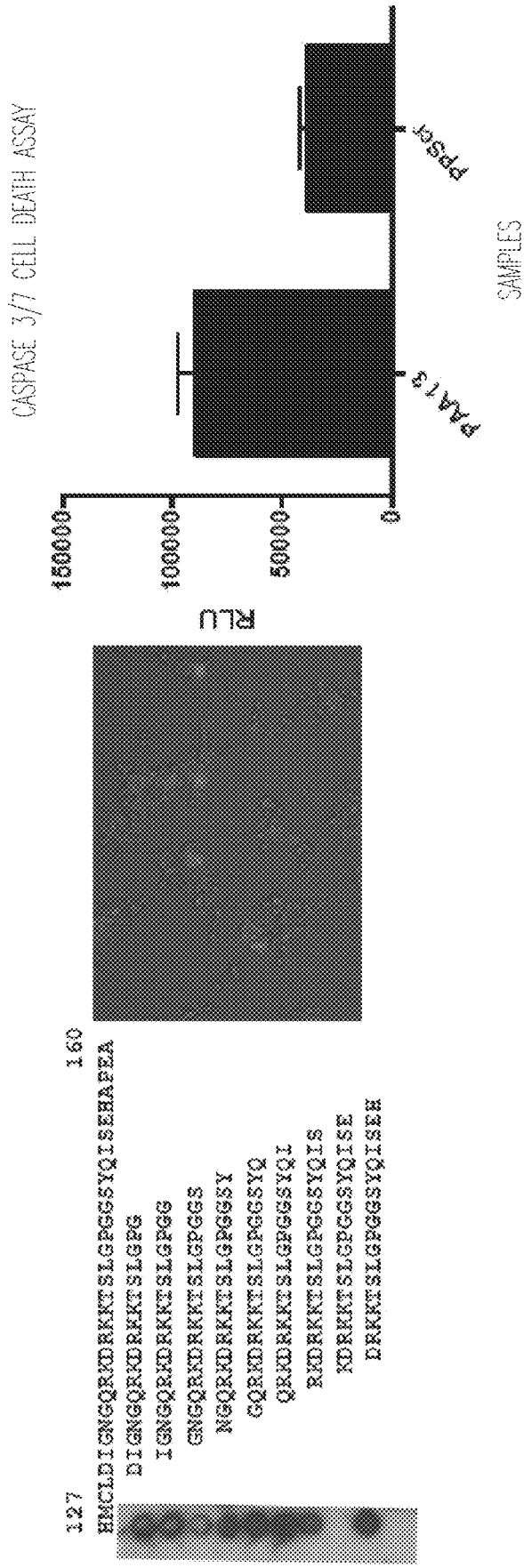
Figure 13C:
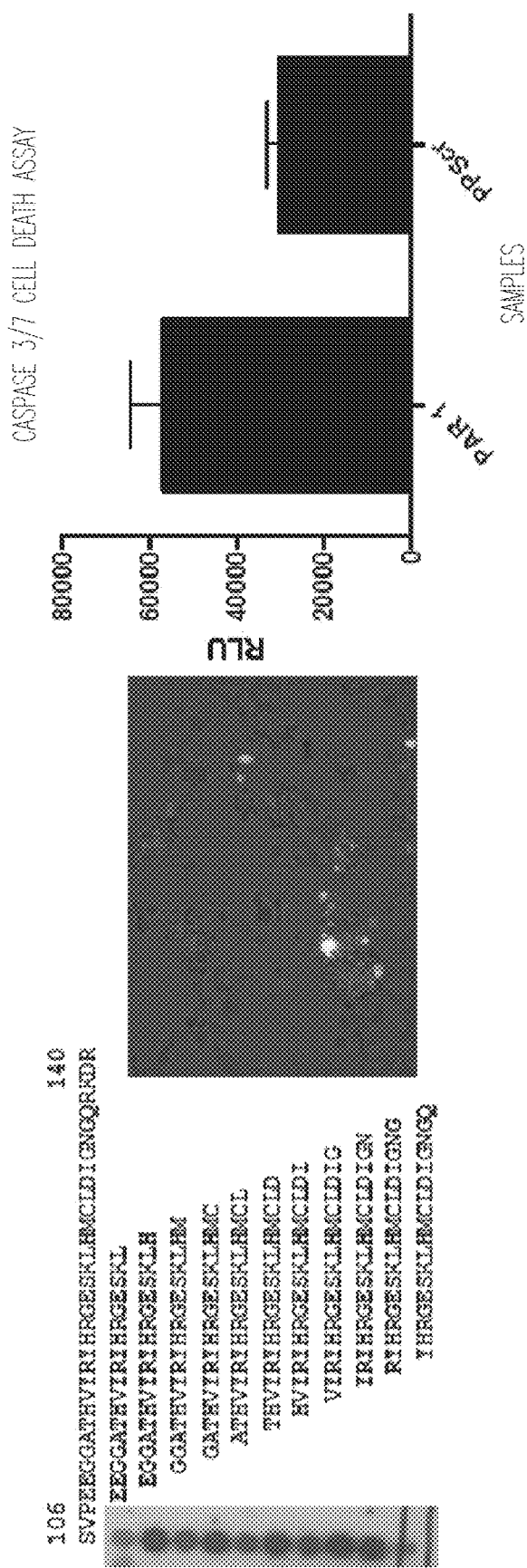
Figure 13D:
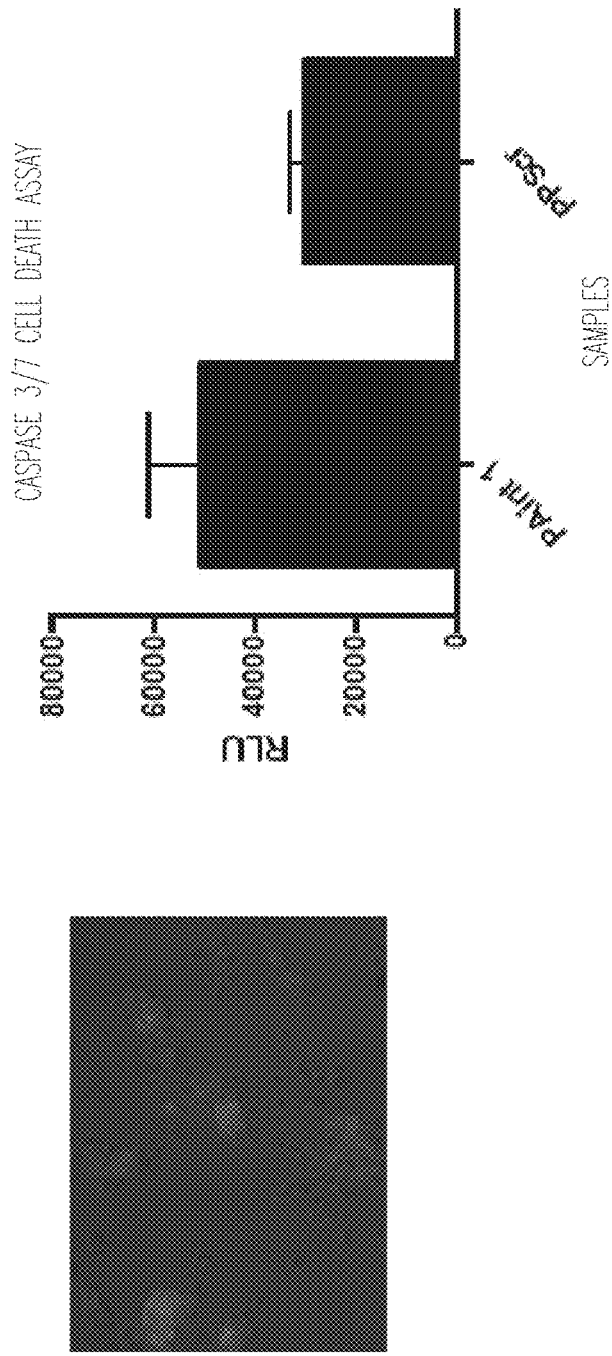

ADPs were first identified using Peptide SPOT analysis. Peptides were identified from AKIP1, PKAc. HSP-70 and p65 sequences. The identified ADPs were attached at the N-terminus to tumor penetrating peptide based on the CENDR rule (FIG. 9). A fluorescent tag was attached to the C-terminus for ease of visualization.

To test these ADPs, CRISPR based AKIP1 knock-out cell lines were generated in HEK 293 and glioblastoma cell lines. Further, all the isoforms of AKIP1 were reintroduced into the AKIP1 knock-out glioblastoma cell lines.

Cell-permeable ADPs may be particularly useful in anti-angiogenic therapies.

ADPs peptides from PKAc include but are not limited to:

```
ADPs peptides from PKAc include but are not
limited to:
PPA 1:
                                        (SEQ ID NO: 2)
GNAAAAKKGSEQESVKEFLAKAKEDFLKK PPA4:
                                       (SEQ ID NO: 19)
VKEFLAKAKEDFLKKWESPAQ PPA10:
                                       (SEQ ID NO: 26)
TWTLCGTPEYLAPEI ILSKGYN KAVDWWALGVLIYEMAAGYPPFF;

from HSP70 include but are not limited to:
PHA4:
                                       (SEQ ID NO: 28)
KSQVISNAKNTVQGFKRFHGRAFSDPFVEAEKSNLAYDIVQW

PTGLTGIKVIYMEEERNFTIEQVTAMLLSKLKETAESVLKKPW

PHA5:
                                       (SEQ ID NO: 27)
IMQDKLEKERNDAKNAVEEYVYEMRDKLSGEYEKFVSEDDRN

SFTLKLEDTENWL;

from p65 include but are not limited to:
PRA1:
                                       (SEQ ID NO: 14)
PLIFPAEPAQASGPYVEIIEQPKQ PRA8:
                                        (SEQ ID NO: 8)
VKKRDLEQAISQRIQTNNNPFQVPIEEQRG DYDLNAVR And from AKIP1 include but are not limited to:
PAAI 1:
                                       (SEQ ID NO: 11)
LNGVDRRSLQRSARLALEVLERAK PAAI 3:
                                        (SEQ ID NO: 5)
DIGNGQRKDRKKTSLGPGGSYQISEHA PAR1:
                                        (SEQ ID NO: 9)
KYYSSVPEEGGATHVYRYHRGESKLHM PAP1:
                                        (SEQ ID NO: 7)
GGSYQISEHAPEASQPAENISKDLYIEVYPGTYS Paint1:
                                       (SEQ ID NO: 30)
DNCLAAAALNGVDRRSLQRSAKLALEVLERAKRR
```

TABLE 6

| Peptide Name | Effectiveness |
| --- | --- |
| PPA 1 | Low to moderate |
| PPA 4 | Moderate |
| PPA 10 | Moderately high |
| PHA 4 | Moderate |
| PHA 5 | High |
| PRA 1 | High |
| PRA 8 | Moderate |
| PAA 11 | High |
| PAA 13 | High |
| PAR 1 | High |
| PAP 1 | Low |
| PAint | Moderate |

HumExemplary human sequences for AKIP. HSP70, p65 and PKAc are as follows: Akip Accession No. NP_065693 (bolded sequence show exemplary ADPs):

```
                                       (SEQ ID NO: 31)
mdnclaaaal ngvdrrslqr sarlalevle rakrravdwh alerpkgcmg vlareaphle kqpaagpqrv lpgereerpp tlsasfrtma efmdytssqc gkyyssvpee ggathvyryh rgesklhmcl dignggrkdr kktslgpggs ygisehapea sqpaeniskd lyievypgty svtvgsndlt kkthvvavds gqsvdlvfpv HSP70 Accession No. NP_002145:
                                       (SEQ ID NO: 32)
msvvgidlgf qscyvavara ggietianey sdrctpacis fgpknrsiga aaksqvisna kntvqgfkrf hgrafsdpfv eaeksnlayd ivqlptgltg ikvtymeeer nftteqvtam llsklketae svlkkpvvdc vvsvpcfytd aerrsvmdat qiaglnclrl mnettavala ygiykqdlpa leekprnvvf vdmghsayqv svcafnrgkl kvlalafdtt lggrkfdevl vnhfceefgk kykldikski rallrlsqec eklkklmsan asdlplsiec fmndvdvsgt mnrgkflemc ndllarvepp lrsvleqtkl kkediyavei vggatripav kekiskffgk elsttlnade avtrgcalqc ailspafkvr efsitdvvpy pislrwnspa eegssdcevf sknhaapfsk vltfyrkepf tleayysspq dlpypdpaia qfsvqkvtpq sdgssskvkv kvrvnvhgif svssaslvev hkseeneepm etdqnakeee kmqvdqeeph veeqqqqtpa enkaeseeme tsqagskdkk mdqppqakka kvktstvdlp ienqllwqid remlnlyien eqkmimgdkl ekerndakna veeyvyemrd klsgeyekfv seddrnsftl kledtenwly edgedqpkqv yvdklaelkn lgqpikirfq eseerpklfe elgkqiqqym kiissfknke dqydhldaad mtkvekstne amewmnnkln lqnkqsltmd pvvkskeiea kikeltstcs piiskpkpkv eppkeeqkna eqngpvdgqg dnpgpqaaeq gtdtavpsds dkklpemdid P65 Accession No. CAA80524:
                                       (SEQ ID NO: 33)
mdelfplifp aepagasgpy veiiegpkqr gmrfrykceg rsagsipgrr sldttkthpt ikingytgpg tvrislvtkd
``` pphrphphel vgkdcrdgfy eaelcpdrci hsfqnlgiqc vkkrdleqai sqriqtnnnp fqvpieeqrg dydlnavrlc fqvtvrdpsg rplrlppvls hpifdnrapn taelkicrvn rnsgsclggd eifllcdkvq kedievyftg pgweargsfs qadvhrqvai vfrtppyadp slqapvrvsm qlrrpsdrel sepmefqylp dtddrhriee krkrtyetfk simkkspfsg ptdprppprr iavpsrssas vkpapqpyp ftsslstiny defptmvfps grsarprlgp appqvlpqap apapapamvs alaqapapvp vlapgppqav appapkptqa gegtlseall qlqfddedlg allgnstdpa vftdlasvdn sefqqllnqg ipvaphttep mlmeypeait rlvtgaqrpp dpapaplgap glpngllsgd edfssiadmd fsallsqiss PKAc (beta) Accession No. KAPCB_HUMAN:
(SEQ ID NO: 34)
mgnaatakkg sevesvkefl akakedflkk wenptqnnag ledferkktl gtgsfgrvml vkhkateqyy amkildkqkv vklkqiehtl nekriiqavn fpflvrleya fkdnsnlymv meyvpggemf shlrrigrfs epharfyaaq ivltfeylhs ldliyrdlkp enllidhqgy iqvtdfqfak rvkgrtwtic gtpeylapei ilskgvnkav dwwalgvliy emaagvppff adqpiqiyek ivsgkvrfps hfssdlkdll rnllqvdltk rfgnlkngvs dikthkwfat tdwiaiyqrk veapflpkfr gsgdtsnfdd yeeedirvsi tekcakefge f PKAc (alpha) Accession No. KAPCA_HUMAN
(SEQ ID NO: 35)
mgnaaaakkg seqesvkefl akakedflkk wespaqntah ldqferiktl gtgsfgrvml vkhketgnhy amkildkqkv vklkqiehtl nekrilqavn fpflvklefs fkdnsnlymv meyvpggemf shlrrigrfs epharfyaaq ivltfeylhs ldliyrdlkp enllidqqgy iqvtdfgfak rvkgrtwtlc gtpeylapei ilskgynkav dwwalgvliy emaagyppff adqpiqiyek ivsgkvrfps hfssdlkdll rnllqvdltk rfgnlkngvn diknhkwfat tdwiaiyqrk veapfipkfk gpgdtsnfdd yeeeirvsi nekcgkefse f cAMP-dependent protein kinase catalytic subunit
beta isoform 11 Accession No. NP_001287845.1
(SEQ ID NO: 58)
MAAYREPPCNQYTGTTTALQKLEGFASRLFHRHSKGTAHDQKTALENDSL

HFSEHTALWDRSMKEFLAKAKEDFLKKWENPTQNNAGLEDFERKKTLGTG

SFGRVMLVKHKATEQYYAMKILDKQKVVKLKQIEHTLNEKRILQAVNFPF

LVRLEYAFKDNSNLYMVMEYVPGGEMFSHLRRIGRFSEPHARFYAAQIVL

TFEYLHSLDLIYRDLKPENLLIDHQGYIQVTDFGFAKRVKGRTWTLCGTP

EYLAPEIILSKGYNKAVDWWALGVLIYEMAAGYPPFFADQPIQIYEKIVS

GKNF cAMP-dependent protein kinase catalytic subunit
beta isoform 7 Accession No. NP_001229789.1
(SEQ ID NO: 59)
MSARKSSDASACSSSEISDSFVKEFLAKAKEDFLKKWENPTQNNAGLEDF

ERKKTLGTGSFGRVMLVKHKATEQYYAMKILDKQKVVKLKQIEHTLNEKR

ILQAVNFPFLVRLEYAFKDNSNLYMVMEYVPGGEMFSHLRRIGRFSEPHA

RFYAAQIVLTFEYLHSLDLIYRDLKPENLLIDHQGYIQVTDFGFAKRVKG

RTWTLCGTPEYLAPEIILSKGYNKAVDWWALGVLIYEMAAGYPPFFADQP

IQIYEKIVSGKVRFPSHFSSDLKDLLRNLLQVDLTKRFGNLKNGVSDIKT

HKWFATTDWIAIYQRKVEAPFIPKFRGSGDTSNFDDYEEEDIRVSITEKC

AKEFGEF

Example 2

Methods

Cell Culture

A549 and MD-MBA-231 were grown in Dulbecco's modified Eagle medium (DMEM, Sigma) supplemented with 10% fetal bovine serum (Sigma) and 1% GlutaMax (Thermo Fisher Scientific) at 37° C. under 5% CO2. U87-MG was also grown under similar conditions except that it was additionally supplemented with 1% non-essential amino acids (Thermo Fisher Scientific). OMM1-3 was grown in RPMI1640 (Thermo Fisher Scientific) supplemented with 10% fetal bovine serum and 1% GlutaMax. Human astrocytes isolated from human brain (cerebral cortex), purchased from Sciencell Research Laboratories, were plated in dishes coated with poly-L-Lysine and incubated at 37° C. in 5% C02. At 70-80% confluency, the cells were either untreated or treated with 100 microM hydrogen peroxide ($H_2O_2$) for 2-4 hours and then harvested. H9C2 and CAD were grown in Dulbecco's modified Eagle medium (DMEM. Sigma) under similar conditions mentioned above. SHSY5Y was grown in DMEMF12 media with 10% FBS and 1% GlutaMax.

Pull-Down Experiments

GST-AKIP1 constructs were transfected into HEK-293 cells. For transfections, cells (seeded at 1.26106 cells/10-cm dish) were grown to 70% confluence and transfected (2 microgram total plasmid DNA and 60 microliter Effectene per 10 cm dish) according to manufacturer's protocol (Qiagen, Valencia, Calif., USA). 24h post transfection, the cells were lysed and separated on 4-12% SDS-PAGE gels and subjected to western blot analysis.

Immuno-Blot Analysis

The blots were probed with anti-GST, anti-AIF anti-HSP-70 and anti-PKAc antibodies to detect endogenous AIF, HSP-70 and PKAc. Similar pull down methods were used for NF-kappaB except that the GST-AKIP1 constructs were co-transfected with flag-p65 subunit and flag-cREL subunit of NF-kappaB. The blots were probed with anti-GST and anti-flag antibodies. The blots were developed with either ProSignal Pico or Dura substrates from Genesse Scientific. For the various western blot analysis, the following antibodies were used at the given concentrations: anti-FLAG (1:1000), anti-AKIP1 (1:5000), anti-AiF (1:1000), anti-HSP-70 (1:1000), anti PKAc (1:1000) and anti-Actin (1:2000).

Peptide SPOT Analysis:

A peptide SPOT array was generated using amino acid sequences (15-18 mers) from AKIP1, AIF, PKAc, HSP-70 and p65 that were synthesized onto an AC-S01 type amino- PEGylated membrane using INTAVIS MultiPep peptide synthesizer (INTAVIS Bioanalytical Instruments AG, Koeln, Germany). The array was activated with ethanol, washed and blocked with blocking agent such as 5% Milk in PBS containing 0.1-0.05/% Tween for 2-3 hours. The membrane was and incubated overnight with in vitro translated or purified AKIP1 or AIF, PKAc, HSP-70 and p65 proteins. For example, AKIP1 was generated by using untagged pRSET construct of AKIP 1a that was in vitro translated using rabbit reticlulate lysate. After incubation with the protein, the peptide array was analyzed by Western blot analysis. The imaged spots were then scanned against the sequences to determine potential binding sites/regions.

AKIP1 KO CRISPR Derived Cell Lines

AKIP1 CRISPR lines were obtained by Cas9-mediated genome editing via nonhomologous end joining (NHEJ) (Ran et al., 2013) Four gRNAs were designed, cloned into a plasmid containing GFP and transfected into U87MG cells. SURVEYOR assays were performed and, based on cleavage efficiency, two of the gRNAs were selected and used for further experiments. Populations of cells transfected were sorted by FACS analysis followed by an expansion of the single cells to new clonal cell lines for both the gRNAs. AKIP1 KO cells were selected by isolating genomic DNA followed by SURVEYOR assay. The Indel mutations were verified by sequencing and confirmed by western blot analysis using AKIP1-specific antibodies.

Cell Migration

The effect on cell migration was monitored as this plays a pivotal role in cancer metastasis. For cell invasion assays, matrigel (final concentration of 200 microg/ml) was pipetted into each Corning permeable insert placed in a 24-well plate and polymerized for 30 min at 37° C. WT and AKIP1 KO cells ($2\times10^4$) were plated in 200 microliter of conditioned medium and incubated at 37° C. in 5% $CO_2$ for 20 h.

The media was then carefully removed from the insert. The cells at the bottom were collected after trypsinization and the migrated cells were lysed, quantified using CyQuant® GR dye solution with a fluorescence plate reader at 480 nm/520 nm.

AAVS1-AKIP1 Isoform Specific Rescue Cell Lines

GeneCopoeia AAVS1-specific CRISPR-Cas9 knock-in kit was used to generate stably expressed AKIP1 isoform specific cell lines according to manufacturer's protocol. This system transfers the gene of interest on a donor plasmid into the AAVS1 safe harbor site on human chromosome 19 via CRISPR-Cas9-mediated homologous recombination (HR). The donor plasmid has a GFP and puromycin marker for selection. Briefly, U87 KO1 cells were plated at around 50,000 cells/well in a 6 well plate so that they were 70-80% confluent at the time of transfection. Then they were cotransfected with AAVS1 plasmid containing CRISPR-Cas9 and the donor plasmid containing the knock-in clone. Puromycin (1 microg/microliter) selection was used to enrich the clones and then these clones were further selected for GFP positive cells using FACS.

Tumor Regression and Rescue in Xenograft Mouse Models

BALB/c mice (4-5 weeks of age, 18-20 g and mixed sexes) were housed and maintained in full compliance with policies of the Institutional Animal Core and Use Committee (IACUC). A small cohort of BALB/c mice of mixed sexes were randomly divided into two groups (n=6 per group). The mice were inoculated subcutaneously either with WT, with AKIP1 KO cells, or with the AKIP1 isoform specific rescue cell lines ($5\times10^5$) in the left dorsal flank. Tumors were examined twice weekly; length and width measurements were obtained with calipers and tumor volumes were calculated using the equation $(L\times W^2)/2$. The tumors were then resected, measured and photographed.

Brain Organelle and Optic Nerve Isolation

The organelles were isolated from adult Sprague Dawley Rats. All rats were housed and maintained in full compliance with policies of the Institutional Animal Core and Use Committee (IACUC).

In Silico Computational Programs

A number of in silico target validation software tools were used. Heliquest was used to determine amphipaticity of the peptides. The program was used obtain data about the mean hydrophobicity ($\langle H \rangle$), the hydrophobic moment (pH) and the net charge (z). Discrimination factor (D) was calculated to determine lipid binding. D depends on the hydrophobic moment (pH) and the net charge (z) and is defined according to: $D=0.944 ((pH))+0.33 (z)$. When D is above 0.68, then this region can be considered to be a (potential) lipid-binding helix72. Further, 3D-Hydrophobic Moment was used to determine the surface polarity of the peptides and is a useful tool in determining the amphipathicity of the peptides (Reisser et al., 2014).

Agadir was used to predict % Helicity Propensity and IUPred2 to predict % Disorder. Agadir uses helix propensity scale based on studies of the stability of proteins and the -helix to-coil transition of peptides (Lacroix et al., 1998).

Intrinsically disordered regions (IDRs) are able to adapt disorder-order confirmation depending in the cellular milieu and its interactome. The IDR predictor, IUPred2 uses an energy estimation method at its core. This approach utilizes a low-resolution statistical potential to characterize the tendencies of amino acid pairs to form contacts, observed in a collection of globular protein structures (Thomas et al., 1996). An amino acid residue having an IUPred2 score of >0.5 is considered disordered. Therefore, % Disorder of the peptide region was calculated as: (No of amino acids with an IUPred2 Score of >0.5)/(Total number of residues)*100.

Plasmid Construction and Expression of Peptide Fragments

The gene fragments of the selected peptide gene sequences were purchased from Genewiz Inc.

Briefly, pSNAP vector from New England Biolabs was linearized by PCR method using 5× Q5 from New England Biolabs. The peptide gene fragments were cloned into pSNAP using the Gibson assembly kit in frame with the SNAP-fluorescent tag. These constructs were then transfected into U87-MG cells using Invitrogen's Lipofectamine 3000. Twenty four hour post transfection, the cells were harvested and subjected to western blot analysis or taken for live cell imaging.

Live Cell Imaging of the SNAP-Tagged Fused Peptides

For live cell imaging, cells were treated with 50 nM of 568 Janelia Fluor® Dye in Invitrogen's Fluorobrite media for 30 mins. The cells were then washed two to three times with 1× Phosphate Buffered Saline (PBS). Fluorbrite media was then added to the cells incubated at 37° C. for 30 minutes. The cells were then washed 3-5 times with PBS. Fluorbrite media was then added to the cells and imaged on Zeiss axiovert inverted microscope using 549 excitation filter.

Dual-Luciferase Promoter Activity Assays

AKIP1 isoforms were cloned in-frame into pGL4.10 [luc2] Vector downstream of the Gal4 DNA binding domain. 10-20,000 HEK-293 cells were plated onto 96 well white plates and transfected with AKIP1 constructs along with pRL (*Renilla* Luciferase plasmid). After 24h post-transfection, the cell were treated with Dual-Glo® Luciferase Buffer according to manufacturer's protocol (Promega). *Renilla* Luminescence was used as an internal control. The output of the luciferase assays was in relative Luminescense units (RLU) which was normalized against the RLU from expressed *Renilla* Luciferase/well. Promoter activity was determined, and statistical analysis of the data performed using MS Office Excel and the GraphPad Prism software (GraphPad Prism software Inc., US).

Apoptotic assays using Caspase-Glo® 3/7 kit

Caspase-Glo® 3/7 assays (Promega) were performed according to the manufacturer's protocol. Briefly, 15,000-20,000 cells were seeded in a 96 well white flat bottom plate. The peptide constructs were transfected in triplicates using Lipofectarnine 3000. Twenty four hour post-transfection, the cells were equilibrated at room temperature and Caspase-Glo® 3/7 reagent was dispensed into each well and the luminescent signal was measured 30-60 mins incubation at room temperature. The blank reaction was used to measure background luminescence associated with the cell culture system and Caspase-Glo® 3/7 Reagent alone. The value for the blank reaction was subtracted from experimental values to obtain the relative luminescence values (RLU). The percentage change over the Scrambled control was calculated from the mean as follows: [(Mean peptide RLU-Mean Scr RLU)/Scr RLU*100]. The P value was calculated using the Student t Test.

Cell Viability Assay with CellTitre-Glo®

CellTitre-Glo® assays (Promega) were performed according to the manufacturer's protocol very similar to the method for Caspase-Glo® 3/7 above. The value for the blank reaction was subtracted from experimental value to obtain the relative luminescence value (RLU). For cancer cells, to determine decreased viability, the percentage change Scrambled control over the peptides was calculated from the mean as follows: [(Mean Scr RLU–Mean peptide RLU)/Scr RLU*100]. For cardiac and neuronal cells, to determine increased cell viability, the percentage change over the Scrambled control was calculated from the mean as follows: [(Mean peptide RLU-Mean Scr RLU)/Scr RLU*100]. The P value was calculated using the Student t Test.

Example 3

Since AKIP1 causes metastasis and is involved in cancer progression, a number of human metastatic cell lines including MD-MBA-231 (breast cancer), A541 (lung), OMM1-3 (Uveal Melanoma) and U87-MG (Glioblastoma Multiforme-GBM) were tested for the presence of AKIP1. A western blot showed that AKIP1 is present in lung (A541), breast (MD-MBA231), eye (OMM1-3) and brain (U87-MG) cancer cell lines. Thus, AKIP1 is expressed in metastatic cell lines.

Example 4

AKIP1 expression was tested in dissected multiple rat brain regions. AKIP1 expression is negligible in cerebellum, cortex, midbrain and the optic nerve. Furthermore, it is lowly expressed in normal glial cells such as astrocytes when compared to GBM cell lines such as U87-MG and U251. Furthermore, there is an increase in AKIP1 expression upon treatment with hydrogen peroxide ($H_2O_2$) to mimic oxidative stress. Thus, AKIP1 is minimally expressed in normal brain but highly expressed in Glioblastoma Multiforme (GBM) cell lines.

Example 5

Figure 14:
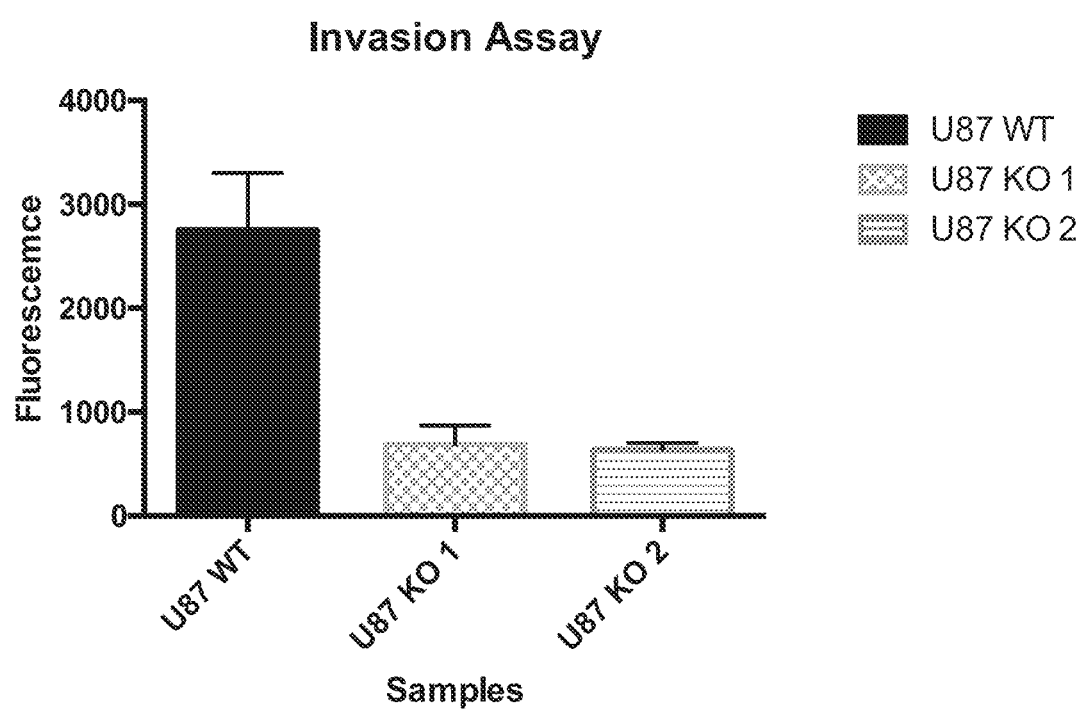
FIG. 14 shows that knockout of AKIP1 reduces cell migration in an invasion assay.
Figure 15:
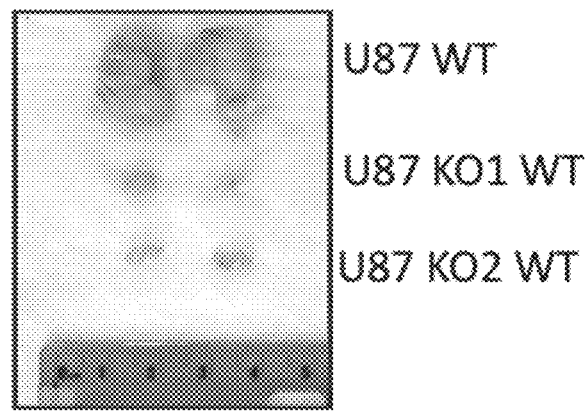
FIG. 15 shows that knockout of AKIP1 reduces tumor volume.
Figure 16:
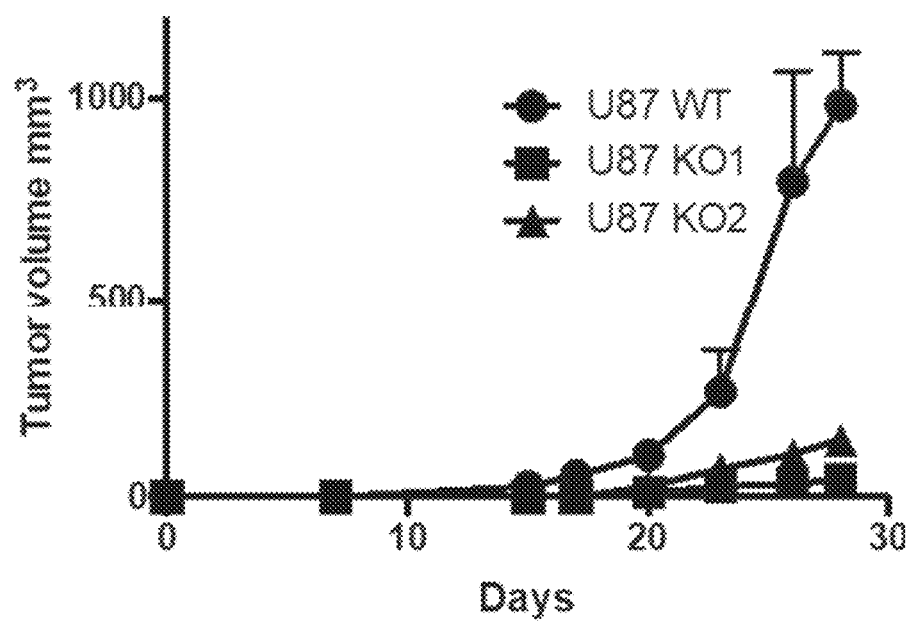
FIG. 16 shows that knockout of AKIP1 reduces tumor volume.

CRISPR Knockout of AKIP1 abrogates cell invasion and causes tumor regression U87-MG serves as a model system for GBM. AKIP1 knock-out (KO) U87MG cells were created using CRISPR/CASP 9 genome editing and two of the KO (U87 KO1 and U87 K02) cell lines were selected for further testing. Western blot analysis showed that the AKIP1 KO cell lines did not express AKIP1. Deletion of AKIP1 results in decreased cell invasion in both the KO cell lines (FIG. 14). AKIP1 KO also causes reduction in tumor volume (FIGS. 15-16). Consequently, AKIP1 is likely essential for tumor progression.

Example 6

There are three major splice variants of AKIP1: AKIP1a, AKIP1b, and AKIP1c. AKIP1b lacks the third exon. The predominant AKIP1c lacks the third and fifth exon. A recent study identified another uncharacterized splice variant that lacks only the fifth exon which we designate here as AKIP1d. FIG. 2 compares the exon structure of the splice variants.

The isoforms show differential binding of the major AKIP1 isoforms to the key interacting proteins such as PKAc, AIF, HSP-70 and p65 subunit of NF-kappaB. AKIP1a binds strongest to AIF and PKAc while all isoforms interact with HSP-70. AKIP1a and AKIP1c bind to p65 of NF-kappaB while AKIP1b binds to the cREL subunit of NF-kappaB. A dual luciferase assay with AKIP1 isoforms shows that AKIP1c is constitutively active, unlike AKIP1a or AKIP1b. Transcriptional assays of AKIP1 splice variants with GAL4 DNA binding domains show that AKIP1a and AKIP1b were minimally activating but AKIP1c showed four-fold increase luciferase activity.

Therefore, AKIP1 isoforms show differential binding and functionalities.

Example 7

Figure 17:
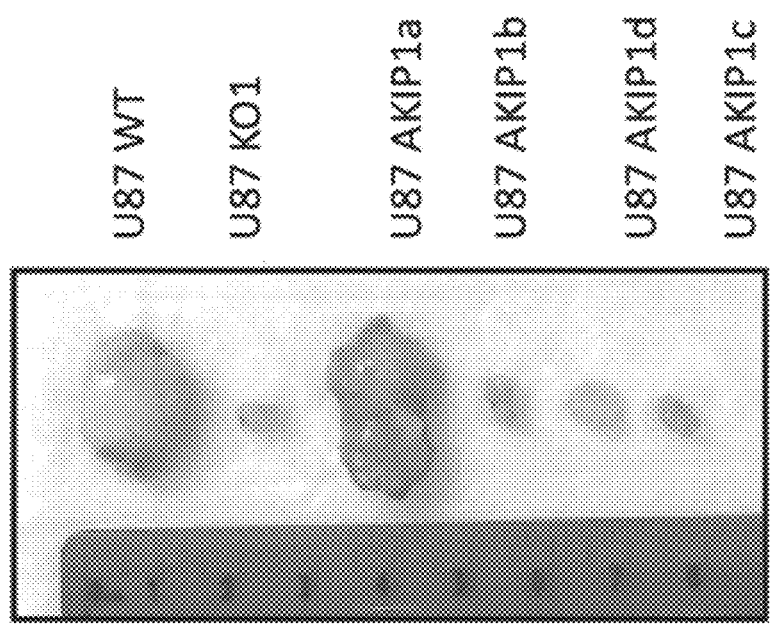
FIG. 17 shows that reintroduction of the splice variant AKIP1a restores tumorigenesis whereas the other isoforms do not.
Figure 18:
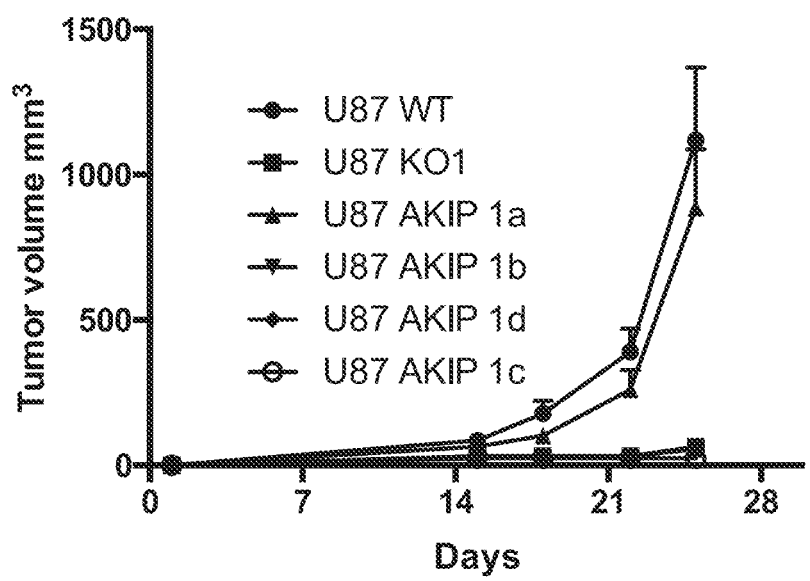
FIG. 18 shows that reintroduction of the splice variant AKIP1a restores tumorigenesis whereas the other isoforms do not.

Rescue experiments were performed by reintroducing the AKIP1 isoforms into U87 KO1 cell-line at the predetermined "safe harbor" AAVS1 site on Chromosome 19. AAVS1 knock-in clones of all the four isoforms (AKIP1a, AKIP1b, AKIP1c and AKIP1d) were constructed and using homologous recombination were integrated into the AAVS1 site. Western blot analysis of the four knock-in cell lines showed high expression of the corresponding isoform in the cell line. When tested in Xenograft mice models, only AKIP1a (the full-length isoform present in human, rat and mouse) has tumor-initiating capacity and functioned as an oncogenic agent, while the rest of the isoforms failed to do so (FIGS. 17 and 18). Therefore, AKIP1a causes tumorigenesis, the other isoforms do not Example 8

AKIP1-Disrupting Peptide (ADP) Design

Peptide SPOT analysis was initially used to identify plausible peptides from AKIP1, PKAc, HSP-70 and p65 sequences. However, given the limitations of peptide arrays and the need to handle stability, cell penetration and other issues such as isoform specificity, variability and required functionality, the specific features as indicated in Table 7 were employed in designing the peptides.

The peptide sequences, the proteins they are derived from and the length are summarized in Table 1 and Table 7.

TABLE 7

| Peptide Name | Protein | SEQ ID No. | Amino Acid Sequence | Length |
|---|---|---|---|---|
| PEPTIDE1 | AKIP1 | 1 | REERPPTLSASFRTMAEFMDYTSSQCG (SEQ ID NO: 1) | 27 |
| PEPTIDE2 | AKIP1 | 2 | RKDRKKTSLGPGGSYQISEHAPEASQP (SEQ ID NO: 2) | 27 |
| PEPTIDE3 | AKIP1 | 3 | RRAVDWHALERPKGCMGVLAREAPHLEKQPAAGPQRVLPGE (SEQ ID NO: 3) | 41 |
| PEPTIDE4 | AKIP1 | 4 | VTVGSNDLTKKTHVVAVDSGQSVDLVFPV (SEQ ID NO: 4) | 29 |
| PEPTIDE5 | AKIP1 | 5 | DIGNGQRKDRKKTSLGPGGSYQISEHA (SEQ ID NO: 5) | 27 |
| PEPTIDE6 | p65 | 6 | NSTDPAVFTDLASVDNSEFQQLLNQGIPVAPHTTEPMLMEYPEAITRLV (SEQ ID NO: 6) | 49 |
| PEPTIDE7 | AKIP1 | 7 | GGSYQISEHAPEASQPAENISKDLYIEVYPGTYS (SEQ ID NO: 7) | 34 |
| PEPTIDE8 | p65 | 8 | VKKRDLEQAISQRIQTNNNPFQVPIEEQRGDYDLNAVR (SEQ ID NO: 8) | 38 |
| PEPTIDE9 | AKIP1 | 9 | KYYSSVPEEGGATHVYRYHRGESKLHM (SEQ ID NO: 9) | 27 |
| PEPTIDE10 | PKAc beta1 | 10 | SHFSEHTALWDRSMKEFLAKAKEDFLKK (SEQ ID NO: 10) | 28 |
| PEPTIDE11 | AKIP1 | 11 | LNGVDRRSLQRSARLALEVLERAK (SEQ ID NO: 11) | 24 |
| PEPTIDE12 | AKIP1 | 12 | DNCLAAAALNGVDRRSLQRSARLALEVLERAKR (SEQ ID NO: 12) | 33 |
| PEPTIDE13 | HSP-70 | 13 | IMQDKLEKERNDAKNAVEEYVYEMRDKLSGEYEKFVSEDDRNSFTLKLEDTENWLY (SEQ ID NO: 13) | 56 |
| PEPTIDE14 | p65 | 14 | PLIFPAEPAQASGPYVEIIEQPKQ (SEQ ID NO: 14) | 24 |
| PEPTIDE15 | HSP-70 | 15 | KSQVISNAKNTVQGFKRFHGRAFSDPFVEAEKSNLAYDIVQWPTGLTGIKVTYMEEERNFTTEQVTAMLLSKLKETAESVLKKPVV (SEQ ID NO: 15) | 86 |
| PEPTIDE16 | PKAc alpha | 16 | TWTLCGTPEYLAPEIILSKGYNKAVDWWALGVLIYEMAAGYPP (SEQ ID NO: 16) | 43 |
| PEPTIDE17 | PKAc alpha | 17 | DWWALGVLIYEMAAGYPP (SEQ ID NO: 17) | 18 |
| PEPTIDE18 | p65 | 18 | VKKRDLEQAISQRIQTNNN (SEQ ID NO: 18) | 19 |
| PEPTIDE19 | PKAc alpha | 19 | VKEFLAKAKEDFLKKWESPAQ (SEQ ID NO: 19) | 21 |
| PEPTIDE20 | PKAc beta7 | 20 | LKKWENPTQNNAGLEDFERKK (SEQ ID NO: 20) | 21 |
| PEPTIDE21 | HSP-70 | 21 | NFTTEQVTAMLLSKLKETAESVLKKPVV (SEQ ID NO: 21) | 21 |
| PEPTIDE22 | PKAc alpha | 22 | LKKWESPAQNTAHLDQFERIK (SEQ ID NO: 22) | 21 |
| PEPTIDE23 | PKAc alpha | 23 | GNAAAAKKGSEQESVKEFLAKEDFLKK (SEQ ID NO: 23) | 29 |
| PEPTIDE24 | p65 | 24 | FIDLASVDNSEFQQLLNQ (SEQ ID NO: 24) | 18 |
| PEPTIDE25 | p65 | 25 | STDPAVFTDLASVDNSEFQQLLNQG (SEQ ID NO: 25) | 25 |
| PEPTIDE SCR | | 26 | GPGKESPPGGEVKPPERREPDQKIPQAPNTSSSNFLLPLAWFFR (SEQ ID NO: 26) | 44 |

The scrambled peptide, as a control, was designed such that it was partly helical, partly intrinsically disordered as well as it had the potential for lipid binding and had a hydrophobic face.

Computational analysis is tabulated in Table 8.

TABLE 8

| Peptide Name | % Helicity | Hydrophobicity <H> | Hydrophobic Moment<mH> | Net Charge | Hydrophobic Face | Discrimination factor "D" | % Disorder |
|---|---|---|---|---|---|---|---|
| PEPTIDE1 | 1.77 | 0.26 | 0.26 | −1 | None | −0.08 | 81.48 |
| PEPTIDE2 | 0.28 | 0.00 | 0.10 | 2 | None | 0.76 | 100.00 |
| PEPTIDE3 | 0.49 | 0.25 | 0.17 | 2 | None | 0.82 | 73.17 |
| PEPTIDE4 | 0.5 | 0.42 | 0.15 | −1 | VLV | −0.19 | 37.93 |
| PEPTIDE5 | 0.41 | −0.02 | 0.16 | 2 | None | 0.81 | 100.00 |
| PEPTIDE6 | 1.52 | 0.45 | 0.17 | −6 | AAPL | −1.82 | 44.90 |
| PEPTIDE7 | 1.28 | 0.30 | 0.14 | −4 | A G I L A A V | −1.19 | 67.65 |
| PEPTIDE8 | 3.08 | 0.98 | 0.11 | 0 | None | 0.10 | 81.58 |
| PEPTIDE9 | 0.27 | 0.18 | 0.10 | 1 | PLY | 0.42 | 59.26 |
| PEPTIDE10 | 17.51 | 0.21 | 0.34 | 1 | FAM | 0.65 | 42.86 |
| PEPTIDE11 | 5.58 | 0.12 | 0.31 | 3 | AL | 1.28 | 45.83 |
| PEPTIDE12 | 14.27 | 0.15 | 0.21 | 3 | AAL | 1.19 | 36.36 |
| PEPTIDE13 | 4.56 | 0.03 | 0.15 | −7 | LMVF | −2.17 | 25.00 |
| PEPTIDE14 | 0.15 | 0.50 | 0.23 | −2 | I A F P Y P P I | −0.44 | 79.17 |
| PEPTIDE15 | 4.33 | 0.36 | 0.03 | 0 | IAWFLY | 0.03 | 15.12 |
| PEPTIDE16 | 1.58 | 0.69 | 0.91 | −2 | W G P G G A L Y Y W | 0.20 | 19.05 |
| PEPTIDE17 | 2.56 | 0.84 | 0.23 | −2 | M L Y I W A G P Y W A V P | −0.45 | 5.56 |
| PEPTIDE18 | 4.57 | −0.04 | 0.15 | 2 | None | 0.80 | 100.00 |
| PEPTIDE19 | 16.03 | 0.20 | 0.47 | 1 | AVPFW | 0.77 | 57.14 |
| PEPTIDE20 | 0.94 | −0.05 | 0.21 | 1 | LP | 0.53 | 100.00 |
| PEPTIDE21 | 9.26 | 0.37 | 0.18 | 1 | None | 0.50 | 39.29 |
| PEPTIDE22 | 0.56 | 0.18 | 0.07 | 1 | LP | 0.40 | 90.48 |
| PEPTIDE23 | 11.63 | −0.04 | 0.21 | 2 | AAV | 0.86 | 55.17 |
| PEPTIDE24 | 1.24 | 0.35 | 0.38 | −3 | None | −0.63 | 0.00 |
| PEPTIDE25 | 1.57 | 0.32 | 0.24 | −4 | F G F A P L | −1.10 | 36.00 |
| PEPTIDESCR | 0.05 | 0.21 | 0.16 | 4 | MGPP | 1.47 | 86.36 |

Representative conservative amino acid substitutions are provided in the Table below.

TABLE 9

| NAME | Amino Acid Position | Potential Substitutions |
|---|---|---|
| PEPTIDE1 | 3E | A, D, G, K, N, P, Q, R, S, T |
| | 5P | A, C, D, E, F, G, H, I, K, L, M, N, P, Q, R, S, T, V, W |
| | 10A | E, G, K, P, S, T, V |
| | 13R | A, C, D, E, F, G, H, I, L, M, N, P, Q, R, S, T, V, Y |
| | 14T | A, D, E, G, I, K, L, N, P, S, V |
| | 18F | I, L, V, W, Y |
| | 20D | A, E, G, H, K, N, P, Q, R, S, T |
| PEPTIDE2 | 5K | A, E, G, H, K, L, N, P, Q, S, T |
| | 12G | A, C, D, E, F, G, H, I, L, M, N, P, Q, R, S, T, V, W, Y |
| | 13G | A, C, E, F, G, H, I, K, L, N, P, Q, R, S, T, V, Y |
| | 14S | A, C, D, E, F, G, H, K, L, M, N, P, Q, R, S, T, W, Y |
| | 17I | A, L |
| PEPTIDE3 | 7H | E, H, K, N, P, Q |
| | 9L | A, F, I, M, T, V |
| | 11R | A, F, I, K, M, Q, R, V |
| | 15C | A, C, D, G, N, T |
| | 20A | A, G, P, T, V, Y |
| | 21R | A, G, K, Q |
| | 23A | D, G, H, I, K, L, N, P, Q, R, S, T, V, Y |
| | 25H | A, C, F, G, H, I, L, N, R, S, T, V |
| | 26L | A, D, E, F, G, H, I, L, N, P, Q, R, S, T, V, Y |
| | 28K | A, E, G, K, N, Q, S |
| | 29Q | A, E, G, H, L, N, Q, R, S, T |
| | 30P | A, G, L, S, T, V |
| | 35Q | F, I, K, M, Q, R, V |
| | 36R | A, C, G, K, S, T |

TABLE 9-continued

| NAME | Amino Acid Position | Potential Substitutions |
|---|---|---|
| PEPTIDE4 | 5S | G, S, T |
| | 6N | A, D, E, G, H, K, S, T |
| | 7D | A, E, G, K, N, P, Q, S, T |
| | 13H | K, Q, R |
| | 19S | A, G, P, T |
| PEPTIDE5 | 2I | A, C, D, E, F, G, H, I, L, M, N, P, Q, R, S, T, V, W, Y |
| | 11K | A, E, G, H, K, L, N, P, Q, S, T |
| | 18G | A, C, D, E, F, G, H, I, L, M, N, P, Q, R, S, T, V, W, Y |
| | 19G | A, C, E, F, G, H, I, K, L, N, P, Q, R, S, T, V, Y |
| | 20S | A, C, D, E, F, G, H, K, L, M, N, P, Q, R, S, T, V, W, Y |
| PEPTIDE6 | 2S | D, S |
| | 6A | G, S, T |
| | 28P | A, S |
| | 29V | A, D, E, F, G, H, I, K, M, N, P, Q, R, S, T, V, Y |
| | 30A | G, P, S, T, V |
| | 31P | A, D, E, G, H, K, N, S |
| | 32H | A, D, E, F, G, H, K, L, P, Q, R, S, T, V, Y |
| | 34T | G, T |
| PEPTIDE7 | 3S | A, C, D, E, F, G, H, I, K, M, N, P, Q, R, S, T, V, W, Y |
| | 4Y | A, C, E, F, G, H, I, K, L, N, Q, R, S, T, V |
| | 5Q | E, H, K, P, R |
| | 9H | A, C, D, E, F, H, I, K, L, M, N, P, Q, R, S, T, V, Y |
| | 11P | A, I, K, M, Q, V |
| | 12E | A, D, G, K, N, P, Q, R, S, T |
| | 15Q | A, E, H, L, N, Q, R, S, T, W |
| | 16P | A, G, K, P, R, T |
| PEPTIDE8 | 5D | A, D, K, Q |
| | 8Q | A, D, G, H, I, K, L, M, N, P, Q, R, S, V |
| | 12Q | A, D, E, F, G, H, I, L, M, N, P, Q, R, S, T, V, Y |
| | 14I | L, M, V |
| | 15Q | A, D, E, K, N, Q, S, T |
| | 17N | A, D, E, G, K, S |
| | 24P | A, G, S, T |
| | 25I | A, F, M, P, Q, T, V, Y |
| | 27E | D, K, N, Q |
| | 28Q | A, D, E, F, G, H, I, L, M, N, P, Q, R, S, T, V, Y |
| | 29R | A, E, G, H, L, N, P, Q, R, S, T, V |
| | 36A | G, S, T, V |
| PEPTIDE9 | 3Y | A, C, F, G, I, L, S, T, V, W |
| | 4S | A, F, G, I, K, L, N, P, T, V |
| | 6V | A, I, L, M, T |
| | 7P | A, D, E, F, G, I, K, M, N, P, Q, R, S, T, V, Y |
| | 12A | S, T |
| | 13T | A, G, S, V |
| | 16Y | A, C, D, E, F, G, H, I, K, L, M, N, P, Q, R, S, T, V, W |
| | 24K | A, D, G, I, K, L, M, N, P, Q, R, S, T, V |
| | 26H | D, E, G, K, N, Q, R, S |
| PEPTIDE10 | 1S | A, D, E, G, K, L, N, Q, R, S, T, V |
| | 3F | A, C, E, F, G, H, I, K, L, M, N, P, Q, R, S, T, W, Y |
| | 6H | A, C, D, E, F, G, H, I, K, L, M, N, P, Q, R, S, T, V, W |
| | 8A | A, C, E, F, I, K, L, M, P, Q, S, T |
| | 9L | F, I, M, V |
| | 12R | A, D, E, G, H, I, L, N, P, Q, R, S, T, V, Y |
| | 13S | C, D, E, F, G, H, I, K, L, M, N, P, Q, R, S, T, V, Y |
| | 16E | A, D, K, Q |
| | 17F | A, D, E, G, H, I, K, L, M, N, P, Q, R, S, T, V, W, Y |
| | 27K | A, D, E, G, H, K, L, N, P, Q, S, T, V |
| PEPTIDE11 | 2N | A, D, E, G, H, K, P, Q, R, S, T, W, Y |
| | 3G | A, C, D, E, F, K, L, N, P, Q, R, S, T, V |
| | 5D | E, G, H, N |
| | 12S | A, D, G, I, K, L, N, P, Q, T, V |
| | 13A | G, I, L, S, V |
| | 14R | A, E, G, K, N, Q, S, T |
| | 15L | F, I, M, Q, V |
| | 17L | A, E, F, G, H, I, L, M, N, P, Q, R, S, T, V, Y |
| PEPTIDE12 | 1D | A, D, K, Q |
| | 2N | A, D, E, F, G, H, I, K, L, N, P, Q, R, T, V, Y |
| | 3C | C, F, I, L, V, W |
| | 4L | A, E, F, I, K, M, P, Q, R, S, T, V |
| | 5A | G, I, K, L, P, S, T, V |
| | 6A | C, D, E, G, K, L, N, P, Q, R, S, T, V |
| | 7A | C, D, E, F, G, I, K, L, N, P, Q, R, S, T, V, Y |
| | 10N | A, D, E, G, H, K, P, Q, R, S, T, W, Y |
| | 11G | A, C, D, E, F, K, L, N, P, S, T, V |
| | 20S | A, D, G, K, L, N, P, T, V |
| | 21A | G, I, L, S, V |

TABLE 9-continued

| NAME | Amino Acid Position | Potential Substitutions |
|---|---|---|
| | 22R | A, E, G, K, N, Q |
| | 25L | A, E, F, G, H, I, L, M, N, P, Q, R, S, T, V, Y |
| PEPTIDE13 | 2M 0.92 | A, D, E, F, G, H, I, K, L, M, N, P, Q, R, S, T, V |
| | 11N | A, D, G, I, K, L, N, P, Q, R, S, T, V |
| | 29S | A, C, D, E, F, G, H, I, K, L, M, N, P, Q, R, S, T, V |
| | 31E | A, D, G, I, K, L, N, P, Q, R, S, T, V |
| | 37S | A, C, D, E, G, I, K, L, N, Q, R, S, V |
| | 39D | A, D, G, K, L, N, P, Q, R, S, T, V |
| | 41R | A, E, H, K, L, Q, S, T |
| | 42N | D, K, N, Q, S |
| | 43S | A, D, E, G, N, Q, R, S, T, V |
| | 45T | A, I, K, L, N, R, S, V |
| | 46L | A, D, G, K, L, N, P, Q, R, S, T, V |
| | 49E | A, D, E, G, K, S, T |
| PEPTIDE14 | 3I | A, F, H, I, L, V |
| | 6A | D, E, K, Q, S |
| | 7E | A, D, K, S |
| | 9A | A, D, K, Q, R, S, T |
| | 10Q | A, D, K, Q, R, S, T |
| | 11A | A, D, E, Q, R, S, T |
| | 12S | A, D, K, N, P, Q, R, S, T |
| | 13G | A, G, K, N, Q, R, S |
| PEPTIDE15 | 8A | A, C, F, G, H, I, K, L, M, N, Q, R, S, T, V |
| | 13Q | A, E, F, G, H, I, K, L, N, Q, R, S, T, V |
| | 22A | A, D, E, G, N, Q, R, S, T |
| | 27F | A, H, I, L, Q, S, V, Y |
| | 30A | A, D, E, G, L, N, Q, R, S, T |
| | 33S | A, D, G, K, L, N, P, Q, R, S, T, V |
| | 34N | A, E, F, G, H, I, K, L, N, Q, R, S, T, V |
| | 38D | A, D, G, K, L, N, Q, R, S, T |
| | 40V | A, D, G, I, K, L, N, Q, R, S, T, V |
| | 41Q | A, D, K, P, Q |
| | 42W | F, M, Q, R, T, V, Y |
| | 43P | A, G, K, N, S |
| | 52T | A, E, L, Q, R, T |
| | 59N | A, E, F, G, H, I, K, L, N, Q, R, S, T, V |
| | 79S 0.98 | A, D, E, I, K.L, N, Q, R, T, Y |
| PEPTIDE16 | 2W | D, F, H, K, N, S, Y |
| | 11L | I, M, V, W |
| | 17L | A, D, E, G, H, I, K, M, N, P, Q, R, S, T, V |
| | 18S | A, C, D, E, F, G, H, I, K, L, M, Q, R, S, T, V, Y |
| | 22N | D, G, S, T |
| | 24A | G, P, S, T |
| | 34I | F, L, M, T, V |
| | 38A | A, I, M, T, V |
| | 39A | C, I, L, N, S, T, V |
| | 41Y | A, E, F, H, I, K, L, N, Q, R, S, T, V |
| PEPTIDE17 | 4A | S, T |
| | 9I | L, V |
| | 13A | A, I, V |
| | 14A | C, N, S, T, V |
| | 16Y | A, F, H, I, L |
| PEPTIDE18 | 5D | A, D, K, Q |
| | 6L | I, V |
| | 8Q | A, D, G, H, I, K, L, M, N, P, Q, R, S, T, V |
| | 11S | S, T |
| | 12Q | A, D, E, G, H, I, L, M, N, P, Q, R, S, T, V, Y |
| | 14I | L, M, V |
| | 15Q | A, D, E, K, Q, S, T |
| | 17N | D, G, S |

Example 9

Nucleic acids encoding each of the peptide sequences PEPTIDE1-PEPTIDE23 were used to generate peptides (T-PEPTIDE) with the following additional sequence elements (see FIG. 19): A Linear Tumor or cardiac penetrating peptide sequence (TPP/CTP) for delivery to cancer or heart cells (Sharma et al., 2017). The TPP sequence—MAKRGARSTA—(SEQ ID NO:58) has an embedded CendR motif (R/K/XXR/K) to induce both cellular uptake and tissue penetration. The peptides also included a SNAP tag for imaging and a FLAG tag for westerns/pull downs. The SNAP and FLAG tags were attached in series at the C terminus. A TEV cleavage site was also introduced to obtain untagged peptide upon cleavage. Each of the vector constructs were expressed in U87-MG cells and analyzed by western blotting and imaging to confirm expression.

Example 10

Select Peptides Increase Apoptosis in U87-MG Glioblastoma Cell Lines

The efficacy of the 25 disclosed peptides to cause apoptosis in the U87-MG cells was measured using Caspase- Glo® 317 Assay. For each of the peptides, the percentage change over the scrambled control was tabulated and a cut-off value at 20 with a P Value of <0.05%. As shown in Table 10, 17 out of the 25 peptides were able to cause significant apoptosis in U87-MG cells.

TABLE 10

| T-PEPTIDE No | % Increase of Apoptosis Over SCR | P Value |
|---|---|---|
| T-PEPTIDE1 | 41 | 0.016 |
| T-PEPTIDE2 | 42 | 0.034 |
| T-PEPTIDE3 | 81 | 0.003 |
| T-PEPTIDE4 | 50 | 0.002 |
| T-PEPTIDE5 | 78 | 0.001 |
| T-PEPTIDE6 | −19 | 0.086 |
| T-PEPTIDE7 | 28 | 0.034 |
| T-PEPTIDE8 | 30 | 0.034 |
| T-PEPTIDE9 | 151 | 0.005 |
| T-PEPTIDE10 | 99 | 0.004 |
| T-PEPTIDE11 | 30 | 0.002 |
| T-PEPTIDE12 | 0 | 0.495 |
| T-PEPTIDE13 | 75 | 0.003 |
| T-PEPTIDE14 | 71 | 0.003 |
| T-PEPTIDE15 | 20 | 0.028 |
| T-PEPTIDE16 | 44 | 0.003 |
| T-PEPTIDE17 | 103 | 0.008 |
| T-PEPTIDE18 | −2 | 0.367 |
| T-PEPTIDE19 | 9 | 0.186 |
| T-PEPTIDE20 | 61 | 0.011 |
| T-PEPTIDE21 | 22 | 0.041 |
| T-PEPTIDE23 | 17 | 0.185 |
| T-PEPTIDE24 | 3 | 0.318 |
| T-PEPTIDE25 | −2 | 0.401 |
| T-PEPTIDESCR | 0 | NA |

The following 17 out 25 peptides caused apoptosis: T-PEPTIDE1, T-PEPTIDE2, T-PEPTIDE3, T-PEPTIDE4, T-PEPTIDE5, T-PEPTIDE7, T-PEPTIDE8, T-PEPTIDE9, T-PEPTIDE10, T-PEPTIDE11, T-PEPTIDE13, T-PEPTIDE14, T-PEPTIDE15, T-PEPTIDE16, T-PEPTIDE17, T-PEPTIDE20 and T-PEPTIDE21.

Example 11

Full Length AKIP1 Isoforms Did not Show Consistent Apoptotic Activity

In contrast, the stable or transfected AKIP1 isoforms gave inconsistent results both in U87-MG as well as in other cancer cell lines. In a Caspase assay, AKIP1a, AKIP1b, AKIP1c showed high apoptosis and high cell viability while AKIP1d showed low apoptosis and low viability.

TABLE 11

| Stable Cell line | % Increase of Apoptosis Over U87_WT | P Value |
|---|---|---|
| AKIP1a | 51 | 0.0103 |
| AKIP1b | 98 | 0.0003 |
| AKIP1c | 28 | 0.0003 |
| AKIP1d | −30 | 0.0009 |

| Stable Cell line | % Increase of Viability Over U87_WT | P Value |
|---|---|---|
| AKIP1a | 4 | 0.023 |
| AKIP1b | 6 | 0.026 |
| AKIP1c | 1 | 0.006 |
| AKIP1d | −28 | 0.415 |

Example 12

CellTiter-Glo® Luminescent Cell Viability was used to test the peptides in U87-MG cells and other cancer cell lines including lung (A549), metastatic breast cancer MD-MBA231, uveolar melanoma (OMM1-3) and another metastatic brain cancer cells (U251).

TABLE 12

| T-PEPTIDE No | U87 % Increase of Apoptosis Over SCR | P Value | U251 % Increase of Apoptosis Over SCR | P Value | A547 % Increase of Apoptosis Over SCR | P Value | MD-MBA-231 % Increase of Apoptosis Over SCR | P Value | OMM1-3 % Increase of Apoptosis Over SCR | P Value |
|---|---|---|---|---|---|---|---|---|---|---|
| T-PEPTIDE1 | 32 | 0.028 | 34 | 0.006 | 19 | 0.021 | 53 | 0.002 | 26 | 0.016 |
| T-PEPTIDE2 | 42 | 0.016 | 27 | 0.027 | 21 | 0.038 | 51 | 0.000 | 20 | 0.028 |
| T-PEPTIDE3 | 46 | 0.018 | 16 | 0.040 | 56 | 0.007 | 51 | 0.000 | −90 | 0.026 |
| T-PEPTIDE4 | 23 | 0.010 | 23 | 0.002 | 62 | 0.008 | 52 | 0.017 | 17 | 0.026 |
| T-PEPTIDE5 | 20 | 0.043 | −23 | 0.023 | 29 | 0.001 | 31 | 0.000 | −45 | 0.145 |
| T-PEPTIDE6 | 27 | 0.026 | −28 | 0.012 | 8 | 0.069 | 1 | 0.431 | −60 | 0.096 |
| T-PEPTIDE7 | 22 | 0.040 | −21 | 0.021 | 33 | 0.004 | 41 | 0.000 | −56 | 0.093 |
| T-PEPTIDE8 | 36 | 0.014 | 33 | 0.005 | 15 | 0.042 | 37 | 0.002 | −84 | 0.042 |
| T-PEPTIDE9 | 21 | 0.046 | −15 | 0.080 | 9 | 0.049 | 47 | 0.000 | 8 | 0.078 |
| T-PEPTIDE10 | 28 | 0.015 | 19 | 0.014 | −7 | 0.199 | 38 | 0.018 | −137 | 0.010 |
| T-PEPTIDE11 | 16 | 0.053 | −22 | 0.049 | 17 | 0.006 | 37 | 0.003 | −7 | 0.264 |
| T-PEPTIDE12 | 23 | 0.045 | 14 | 0.061 | 5 | 0.226 | 3 | 0.259 | 71 | 0.044 |
| T-PEPTIDE13 | 24 | 0.048 | −23 | 0.017 | 28 | 0.006 | 36 | 0.007 | −60 | 0.066 |
| T-PEPTIDE14 | 25 | 0.038 | −9 | 0.001 | 23 | 0.014 | 43 | 0.003 | −11 | 0.098 |

TABLE 12-continued

| T-PEPTIDE No | U87 % Increase of Apoptosis Over SCR | P Value | U251 % Increase of Apoptosis Over SCR | P Value | A547 % Increase of Apoptosis Over SCR | P Value | MD-MBA-231 % Increase of Apoptosis Over SCR | P Value | OMM1-3 % Increase of Apoptosis Over SCR | P Value |
|---|---|---|---|---|---|---|---|---|---|---|
| T-PEPTIDE15 | 24 | 0.036 | −28 | 0.004 | 9 | 0.023 | 41 | 0.002 | −101 | 0.023 |
| T-PEPTIDE16 | 21 | 0.017 | −17 | 0.002 | 1 | 0.468 | 32 | 0.025 | −93 | 0.094 |
| T-PEPTIDE17 | 29 | 0.006 | −10 | 0.011 | −1 | 0.447 | 35 | 0.068 | 24 | 0.078 |
| T-PEPTIDE18 | 27 | 0.035 | −15 | 0.000 | 25 | 0.007 | 59 | 0.002 | −104 | 0.013 |
| T-PEPTIDE19 | 18 | 0.013 | −35 | 0.000 | −11 | 0.139 | 16 | 0.099 | −89 | 0.013 |
| T-PEPTIDE20 | 34 | 0.011 | 12 | 0.029 | −3 | 0.326 | −37 | 0.026 | −89 | 0.126 |
| T-PEPTIDE21 | 25 | 0.040 | 20 | 0.015 | 4 | 0.240 | 5 | 0.150 | −184 | 0.032 |
| T-PEPTIDE22 | 29 | 0.012 | −20 | 0.012 | −8 | 0.215 | 11 | 0.120 | −119 | 0.036 |
| T-PEPTIDE23 | 14 | 0.030 | −15 | 0.037 | −9 | 0.187 | −14 | 0.080 | 51 | 0.055 |
| T-PEPTIDESCR | 0 | | 0 | | 0 | | 0 | | 0 | |

The following 15 out of 23 peptides had decreased cell viability in at least three cell lines (a positive value with a P Value of <0.05%)-T-PEPTIDE1, T-PEPTIDE2, T-PEPTIDE3, T-PEPTIDE4, T-PEPTIDE5, T-PEPTIDE7, T-PEPTIDE8, T-PEPTIDE9, T-PEPTIDE10, T-PEPTIDE11, T-PEPTIDE13, T-PEPTIDE14, T-PEPTIDE15, T-PEPTIDE17 and T-PEPTIDE18. PEPTIDE24 and PEPTIDE25 were not tested due to very low apoptosis.

Example 13

The peptides were also tested for their effect in cell viability in cardiac and neuronal cell lines: Since AKIP1 has a protective role in the heart and possible neuronal cells, the peptides were tested in rat cardiac (H9C2), human neuroblastoma (SHSY5Y) and mouse neuroblastoma (CAD cells) to check the ability of the peptides to increase cell viability using CellTiter-Glo® Luminescent Cell Viability Assay. The percentage increase over Scr was determined. All peptides showing greater than 5% increase over Scr were considered anti-apoptotic.

TABLE 13

| | Type | | | | | |
|---|---|---|---|---|---|---|
| | Neuronal | | Neuronal | | Candiac | |
| | Cell line | | | | | |
| T-PEPTIDE No | CAD % Increase of Cell Viability Over SCR | P Value | SHSY5Y % Increase of Cell Viability Over SCR | P Value | H9C2 % Increase of Cell Viability Over SCR | P Value |
| T-PEPTIDE1 | −23 | 0.010 | −5 | 0.162 | −25 | 0.000 |
| T-PEPTIDE2 | −29 | 0.004 | −4 | 0.255 | −26 | 0.001 |
| T-PEPTIDE3 | −13 | 0.022 | −2 | 0.252 | −18 | 0.002 |
| T-PEPTIDE4 | 11 | 0.051 | 0 | 0.381 | −5 | 0.125 |
| T-PEPTIDE5 | −1 | 0.456 | −2 | 0.120 | −6 | 0.048 |
| T-PEPTIDE6 | 20 | 0.060 | 0 | 0.482 | 14 | 0.012 |
| T-PEPTIDE7 | −20 | 0.019 | −3 | 0.197 | −12 | 0.004 |
| T-PEPTIDE8 | 19 | 0.027 | −1 | 0.060 | −23 | 0.003 |
| T-PEPTIDE9 | −9 | 0.086 | −1 | 0.267 | 4 | 0.224 |
| T-PEPTIDE10 | 6 | 0.139 | −2 | 0.096 | −7 | 0.101 |
| T-PEPTIDE11 | 8 | 0.161 | 0 | 0.497 | 2 | 0.396 |
| T-PEPTIDE12 | 14 | 0.061 | −3 | 0.113 | −10 | 0.011 |
| T-PEPTIDE13 | −23 | 0.017 | −5 | 0.113 | −2 | 0.267 |
| T-PEPTIDE14 | −24 | 0.016 | −4 | 0.091 | 7 | 0.096 |
| T-PEPTIDE15 | −28 | 0.004 | 6 | 0.077 | 5 | 0.088 |
| T-PEPTIDE16 | −23 | 0.004 | 1 | 0.390 | 3 | 0.051 |
| T-PEPTIDE17 | −25 | 0.000 | 2 | 0.162 | −13 | 0.013 |
| T-PEPTIDE18 | −23 | 0.010 | −5 | 0.004 | −3 | 0.226 |
| T-PEPTIDE19 | −41 | 0.002 | 1 | 0.402 | −1 | 0.427 |
| T-PEPTIDE20 | 2 | 0.173 | 2 | 0.276 | −11 | 0.063 |
| T-PEPTIDE21 | 20 | 0.015 | −3 | 0.016 | −5 | 0.033 |
| T-PEPTIDE22 | −20 | 0.012 | 4 | 0.107 | 0 | 0.499 |

TABLE 13-continued

| | Type | | | | | |
|---|---|---|---|---|---|---|
| | Neuronal | | Neuronal Cell line | | Cardiac | |
| T-PEPTIDE No | CAD % Increase of Cell Viability Over SCR | P Value | SHSY5Y % Increase of Cell Viability Over SCR | P Value | H9C2 % Increase of Cell Viability Over SCR | P Value |
| T-PEPTIDE23 | −15 | 0.037 | 4 | 0.116 | −5 | 0.220 |
| T-PEPTIDESCR | 0 | | 0 | | 0 | |

The following 7 out of 23 peptides had increased cell viability in at least two cell lines (a positive value with a P Value of <0.05%)-T-PEPTIDE4, T-PEPTIDE6, T-PEPTIDE8, T-PEPTIDE10. T-PEPTIDE11, T-PEPTIDE12 and T-PEPTIDE16.

Example 14

The transfected AKIP1 isoforms were also tested for their effect in cell viability in cardiac and neuronal cell lines using the CellTiter-Glo® Luminescent Cell Viability Assay. The percentage increase over Scr was determined as (Mean SCRRLU-Mean Peptide RLU)/Scr RLU*100. In contrast to some of the ADPs, none of the stable AKIP1 isoforms showed anti-apoptotic activity.

TABLE 14

| | Type | | | | | |
|---|---|---|---|---|---|---|
| | Neuronal | | Neuronal Cell Line | | Cardiac | |
| | CAD % Increase of Viability Over Vector Control | P Value | SHSY5Y % Increase of Viability Over Vector Control | P Value | H9C2 % Increase of Viability Over Vector Control | P Value |
| AKIP1a | −6 | 0.252 | −1 | 0.314 | −5 | 0.216 |
| AKIP1b | −6 | 0.169 | 0 | 0.348 | −1 | 0.438 |
| AKIP1c | −5 | 0.232 | −1 | 0.249 | −3 | 0.115 |

Example 15

Pro-Apoptotic Peptides, Anti-Apoptotic Peptides, and Peptides that are Both Pro-Apoptotic and Anti-Apoptotic The active ADPs were categorized regarding the following criteria:
1) Decreased cell viability in at least 3 cancer cell lines or decreased cell viability in at least 2 cancer cells and very high apoptosis (>100).
2) Improved cell viability in cardiac or neuronal cell lines and decreased viability in at least 2 cancer cell lines.

TABLE 15

| Proapoptotic | Decreased Cell Viability | Anti-apoptotic |
|---|---|---|
| PEPTIDE1 | PEPTIDE1 | |
| PEPTIDE2 | PEPTIDE2 | |
| PEPTIDE3 | PEPTIDE3 | |
| PEPTIDE4 | PEPTIDE4 | PEPTIDE4 |
| PEPTIDE5 | PEPTIDE5 | |
| | | PEPTIDE6 |
| PEPTIDE7 | PEPTIDE7 | |
| PEPTIDE8 | PEPTIDE8 | PEPTIDE8 |
| PEPTIDE9 | PEPTIDE9 | |
| PEPTIDE10 | PEPTIDE10 | PEPTIDE10 |
| PEPTIDE11 | PEPTIDE11 | PEPTIDE11 |
| | | PEPTIDE12 |
| PEPTIDE13 | PEPTIDE13 | |
| PEPTIDE14 | PEPTIDE14 | |
| PEPTIDE15 | PEPTIDE15 | |
| PEPTIDE16 | | PEPTIDE16 |
| PEPTIDE17 | PEPTIDE17 | |
| | PEPTIDE18 | |

Consequently, Pro-apoptotic (anti-angiogenic) peptides INCLUDE: PEPTIDE1, PEPTIDE2, PEPTIDE3, PEPTIDE4, PEPTIDE5, PEPTIDE7, PEPTIDE8, PEPTIDE9, PEPTIDE10, PEPTIDE11, PEPTIDE13, PEPTIDE14, PEPTIDE15, PEPTIDE16, PEPTIDE17 and PEPTIDE18; and anti-apoptotic (pro-angiogenic) peptides include: PEPTIDE4, PEPTIDE6, PEPTIDE8, PEPTIDE10, PEPTIDE11, PEPTIDE12, PEPTIDE16. PEPTIDE4, PEPTIDE8, PEPTIDE10, PEPTIDE11 and PEPTIDE16 showed both pro and anti-apoptotic effect. This is feasible since these peptides could include effectors for both functions depending on the specific pathways activated in the different cell types.

REFERENCES

Achen, M. G., et al., The angiogenic and lymphangiogenic factor vascular endothelial growth factor-D exhibits a paracrine mode of action in cancer. Growth Factors. 2002. 20(2): p. 99-107.
Booij, H. G., et al., Overexpression of A kinase interacting protein 1 attenuates myocardial ischaemia/reperfusion injury but does not influence heart failure development. Cardiovasc Res, 2016. 111(3): p. 217-26.

Carmeliet, P., Angiogenesis in life, disease and medicine. Nature, 2005. 438(7070): p. 932-6.

De Rosa, L., R. Di Stasi, and L. D. D'Andrea, Pro-angiogenic peptides in biomedicine. Arch Biochem Biophys, 2018. 660: p. 72-86.

Gao, F., et al., Neddylation of a breast cancer-associated protein recruits a class III histone deacetylase that represses NFkappaB-dependent transcription. Nat Cell Biol, 2006. 8(10): p. 1171-7.

Gao, N., et al., A-kinase-interacting protein 1 (AKIP1) acts as a molecular determinant of PKA in NF-kappaB signaling. J Biol Chem, 2010. 285(36): p. 28097-104.

Gao, N., et al., AKIP1 enhances NF-kappaB-dependent gene expression by promoting the nuclear retention and phosphorylation of p65. J Biol Chem, 2008. 283(12): p. 7834-43.

Guo, X., et al., AKIP11 promoted epithelial-mesenchymal transition of non-small-cell lung cancer via transactivating ZEB1. Am J Cancer Res, 2017. 7(11): p. 2234-2244.

Hanahan, D. and R. A. Weinberg, The hallmarks of cancer. Cell, 2000. 100(1): p. 57-70.

Hashimoto, M., E. Murata, and T. Aoki, Secretory protein with RING finger domain (SPRING) specific to *Trypanosoma cruzi* is directed, as a ubiquitin ligase related protein, to the nucleus of host cells. Cell Microbiol, 2010. 12(1): p. 19-30.

Jayson, G. C., et al., Antiangiogenic therapy in oncology: current status and future directions. Lancet, 2016. 388 (10043): p. 518-29.

Kerbel, R. S., Tumor angiogenesis. N Engl J Med, 2008. 358(19): p. 2039-49.

King, C. C., et al., The rate of NF-kappaB nuclear translocation is regulated by PKA and A kinase interacting protein 1. PLoS One, 2011. 6(4): p. e18713.

Kitching, R., et al., Characterization of a novel human breast cancer associated gene (BCA3) encoding an alternatively spliced proline-rich protein. Biochim Biophys Acta. 2003. 1625(1): p. 116-21.

Lacroix, E., A. R. Viguera, and L. Serrano, Elucidating the folding problem of alpha-helices: local motifs, long-range electrostatics, ionic-strength dependence and prediction of NMR parameters. J Mol Biol, 1998. 284(1): p. 173-91.

Lin, C., et al., Overexpression of AKIP1 promotes angiogenesis and lymphangiogenesis in human esophageal squamous cell carcinoma. Oncogene, 2015. 34(3): p. 384-93.

Lin, S. M., et al., Screening and identification of interacting proteins with hepatitis B virus core protein in leukocytes and cloning of new gene C1. World J Gastroenterol, 2006. 12(7): p. 1043-8.

Liu, S., et al., PKA turnover by the REGgamma-proteasome modulates FoxO1 cellular activity and VEGF-induced angiogenesis. J Mol Cell Cardiol, 2014. 72: p. 28-38.

Ma, D., et al., BCA3 contributes to the malignant progression of hepatocellular carcinoma through AKT activation and NF-kappaB translocation. Exp Cell Res, 2018. 362 (1): p. 142-151.

Mo, D., et al., Overexpression of AKIP1 predicts poor prognosis of patients with breast carcinoma and promotes cancer metastasis through AktiGSK-3beta/Snail pathway. Am J Transl Res, 2016. 8(11): p. 4951-4959.

Nakagawa, Y., et al., NF-kB signaling mediates acquired resistance after PARP inhibition. Oncotarget, 2015. 6(6): p. 3825-39.

Osherov, N. and R. Ben-Ami, Modulation of Host Angiogenesis as a Microbial Survival Strategy and Therapeutic Target. PLoS Pathog, 2016. 12(4): p. e1005479.

Perez Pinero, C., et al., Involvement of alpha2- and beta2-adrenoceptors on breast cancer cell proliferation and tumour growth regulation. Br J Pharmacol, 2012. 166(2): p. 721-36.

Prasad, R. C., et al., Identification of genes, including the gene encoding p27Kip1, regulated by serine 276 phosphorylation of the p65 subunit of NF-kappaB. Cancer Lett, 2009. 275(1): p. 139-49.

Ran, F. A., et al., Genome engineering using the CRISPR-Cas9 system. Nat Protoc, 2013. 8(11): p. 2281-308.

Reisser, S., et al., 3D hydrophobic moment vectors as a tool to characterize the surface polarity of amphiphilic peptides. Biophys J, 2014. 106(11): p. 2385-94.

Rumlova, M., et al., Breast cancer-associated protein—a novel binding partner of Mason-Pfizer monkey virus protease. J Gen Virol, 2014. 95(Pt 6): p. 1383-9.

Rumlova, M., et al., Does BCA3 Play a Role in the HIV-1 Replication Cycle? Viruses, 2018. 10(4).

Rumlova, M., et al., HIV-1 protease-induced apoptosis. Retrovirology, 2014. 11: p. 37.

Sastri, M., et al., A kinase interacting protein (AKIP1) is a key regulator of cardiac stress. Proc Natl Acad Sci USA, 2013. 110(5): p. E387-96.

Sastri, M., et al., A-kinase-interacting protein localizes protein kinase A in the nucleus. Proc Natl Acad Sci USA, 2005. 102(2): p. 349-54.

Sharma, S., et al., Tumor-Penetrating Nanosystem Strongly Suppresses Breast Tumor Growth. Nano Lett, 2017. 17(3): p. 1356-1364.

Thomas, P. D. and K. A. Dill, An iterative method for extracting energy-like quantities from protein structures. Proc Natl Acad Sci USA. 1996. 93(21): p. 11628-33.

Zhang, Y., et al., Cloning and functional identification of a novel BCA3 splice. Genet Mol Res, 2014, 13(4): p. 10648-56.

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A composition comprising a viral vector comprising a nucleotide sequence encoding a peptide at least 85% identical to any one of peptides according to SEQ ID NOs: 1-5, 7, 9, or 11, wherein said encoded peptide reduces angiogenesis or induces apoptosis.

2. The composition of claim 1, wherein the viral vector is a lentivirus vector or an adenovirus vector.

3. The composition of claim 1, wherein the viral vector is a virus.

4. The composition of claim 1 further comprising a chemotherapeutic agent.

5. The composition of claim 4 wherein the chemotherapeutic agent is cyclophosphamide, doxorubicin, methotrexate, 5-fluorouracil, paclitaxel, docetaxel, navelbine, capecitabine, mitomycin C, prednisone, a taxane, vinblastine, or tamoxifen.

6. The composition of claim 4 wherein the chemotherapeutic agent is an aromatase inhibitor, a proteinase inhibitor, an integrin inhibitor, a VEGF inhibitor, or a collagen-binding antibody.

7. The composition of claim 1 further comprising an anti-angiogenic agent.

8. The composition of claim 7 wherein the anti-angiogenic agent is a growth factor, a cytokine, a protease, a protease inhibitor, an integrin, an antibody, or a glycosidase.

9. The composition of claim 8 wherein the growth factor is ANG-2, NK1, NK2, NK4, Hepatocyte Growth Factor (HGF), or transforming growth factor beta (TGF-β).

10. The composition of claim 8 wherein the cytokine is interferon alpha (IFN-α), interferon beta (IFN-β), interferon gamma (IFN γ), platelet factor 4 (PF-4) or PR-39.

11. The composition of claim 8 wherein the protease cleaves AT-III, collagen XVIII fragment (Endostatin), HmwKallikrein-d5 plasmin fragment (Angiostatin), pro-thrombin-F1-2, or Thrombospondin-1(TSP-1).

12. The composition of claim 8 wherein the protease inhibitor is tissue inhibitor of metalloprotease 1 (TIMP-1), tissue inhibitor of metalloprotease (TIMP-2), tissue inhibitor of metalloprotease (TIMP-3); plasminogen activator-inhibitor 1 (PAI-1), pigment epithelium derived factor (PEDF), or maspin (mammary serine protease inhibitor).

13. The composition of claim 8 wherein the antibody is HUIV26, HU177, or XL313.

14. The composition of claim 8 wherein the glycosidase is heparinase-I or heparinase-II.

\* \* \* \* \*

SEQUENCE LISTING

```
<160> NUMBER OF SEQ ID NOS: 170

<210> SEQ ID NO 1
<211> LENGTH: 27
<212> TYPE: PRT
<213> ORGANISM: Homo sapiens
```

```
<400> SEQUENCE: 1

Arg Glu Glu Arg Pro Pro Thr Leu Ser Ala Ser Phe Arg Thr Met Ala
1               5                   10                  15

Glu Phe Met Asp Tyr Thr Ser Ser Gln Cys Gly
            20                  25

<210> SEQ ID NO 2
<211> LENGTH: 27
<212> TYPE: PRT
<213> ORGANISM: Homo sapiens

<400> SEQUENCE: 2

Arg Lys Asp Arg Lys Lys Thr Ser Leu Gly Pro Gly Gly Ser Tyr Gln
1               5                   10                  15

Ile Ser Glu His Ala Pro Glu Ala Ser Gln Pro
            20                  25

<210> SEQ ID NO 3
<211> LENGTH: 41
<212> TYPE: PRT
<213> ORGANISM: Homo sapiens

<400> SEQUENCE: 3

Arg Arg Ala Val Asp Trp His Ala Leu Glu Arg Pro Lys Gly Cys Met
1               5                   10                  15

Gly Val Leu Ala Arg Glu Ala Pro His Leu Glu Lys Gln Pro Ala Ala
            20                  25                  30

Gly Pro Gln Arg Val Leu Pro Gly Glu
            35                  40

<210> SEQ ID NO 4
<211> LENGTH: 29
<212> TYPE: PRT
<213> ORGANISM: Homo sapiens

<400> SEQUENCE: 4

Val Thr Val Gly Ser Asn Asp Leu Thr Lys Lys Thr His Val Val Ala
1               5                   10                  15

Val Asp Ser Gly Gln Ser Val Asp Leu Val Phe Pro Val
            20                  25

<210> SEQ ID NO 5
<211> LENGTH: 27
<212> TYPE: PRT
<213> ORGANISM: Homo sapiens

<400> SEQUENCE: 5

Asp Ile Gly Asn Gly Gln Arg Lys Asp Arg Lys Lys Thr Ser Leu Gly
1               5                   10                  15

Pro Gly Gly Ser Tyr Gln Ile Ser Glu His Ala
            20                  25

<210> SEQ ID NO 6
<211> LENGTH: 49
<212> TYPE: PRT
<213> ORGANISM: Homo sapiens

<400> SEQUENCE: 6

Asn Ser Thr Asp Pro Ala Val Phe Thr Asp Leu Ala Ser Val Asp Asn
1               5                   10                  15
```

Ser Glu Phe Gln Gln Leu Leu Asn Gln Gly Ile Pro Val Ala Pro His
            20                  25                  30

Thr Thr Glu Pro Met Leu Met Glu Tyr Pro Glu Ala Ile Thr Arg Leu
        35                  40                  45

Val

<210> SEQ ID NO 7
<211> LENGTH: 34
<212> TYPE: PRT
<213> ORGANISM: Homo sapiens

<400> SEQUENCE: 7

Gly Gly Ser Tyr Gln Ile Ser Glu His Ala Pro Glu Ala Ser Gln Pro
1               5                   10                  15

Ala Glu Asn Ile Ser Lys Asp Leu Tyr Ile Glu Val Tyr Pro Gly Thr
            20                  25                  30

Tyr Ser

<210> SEQ ID NO 8
<211> LENGTH: 38
<212> TYPE: PRT
<213> ORGANISM: Homo sapiens

<400> SEQUENCE: 8

Val Lys Lys Arg Asp Leu Glu Gln Ala Ile Ser Gln Arg Ile Gln Thr
1               5                   10                  15

Asn Asn Asn Pro Phe Gln Val Pro Ile Glu Glu Gln Arg Gly Asp Tyr
            20                  25                  30

Asp Leu Asn Ala Val Arg
        35

<210> SEQ ID NO 9
<211> LENGTH: 27
<212> TYPE: PRT
<213> ORGANISM: Homo sapiens

<400> SEQUENCE: 9

Lys Tyr Tyr Ser Ser Val Pro Glu Glu Gly Gly Ala Thr His Val Tyr
1               5                   10                  15

Arg Tyr His Arg Gly Glu Ser Lys Leu His Met
            20                  25

<210> SEQ ID NO 10
<211> LENGTH: 28
<212> TYPE: PRT
<213> ORGANISM: Homo sapiens

<400> SEQUENCE: 10

Ser His Phe Ser Glu His Thr Ala Leu Trp Asp Arg Ser Met Lys Glu
1               5                   10                  15

Phe Leu Ala Lys Ala Lys Glu Asp Phe Leu Lys Lys
            20                  25

<210> SEQ ID NO 11
<211> LENGTH: 24
<212> TYPE: PRT
<213> ORGANISM: Homo sapiens

<400> SEQUENCE: 11

Leu Asn Gly Val Asp Arg Arg Ser Leu Gln Arg Ser Ala Arg Leu Ala
1               5                   10                  15

Leu Glu Val Leu Glu Arg Ala Lys
            20

<210> SEQ ID NO 12
<211> LENGTH: 33
<212> TYPE: PRT
<213> ORGANISM: Homo sapiens

<400> SEQUENCE: 12

Asp Asn Cys Leu Ala Ala Ala Leu Asn Gly Val Asp Arg Arg Ser
1               5                   10                  15

Leu Gln Arg Ser Ala Arg Leu Ala Leu Glu Val Leu Glu Arg Ala Lys
            20                  25                  30

Arg

<210> SEQ ID NO 13
<211> LENGTH: 56
<212> TYPE: PRT
<213> ORGANISM: Homo sapiens

<400> SEQUENCE: 13

Ile Met Gln Asp Lys Leu Glu Lys Glu Arg Asn Asp Ala Lys Asn Ala
1               5                   10                  15

Val Glu Glu Tyr Val Tyr Glu Met Arg Asp Lys Leu Ser Gly Glu Tyr
            20                  25                  30

Glu Lys Phe Val Ser Glu Asp Asp Arg Asn Ser Phe Thr Leu Lys Leu
        35                  40                  45

Glu Asp Thr Glu Asn Trp Leu Tyr
    50                  55

<210> SEQ ID NO 14
<211> LENGTH: 24
<212> TYPE: PRT
<213> ORGANISM: Homo sapiens

<400> SEQUENCE: 14

Pro Leu Ile Phe Pro Ala Glu Pro Ala Gln Ala Ser Gly Pro Tyr Val
1               5                   10                  15

Glu Ile Ile Glu Gln Pro Lys Gln
            20

<210> SEQ ID NO 15
<211> LENGTH: 86
<212> TYPE: PRT
<213> ORGANISM: Homo sapiens

<400> SEQUENCE: 15

Lys Ser Gln Val Ile Ser Asn Ala Lys Asn Thr Val Gln Gly Phe Lys
1               5                   10                  15

Arg Phe His Gly Arg Ala Phe Ser Asp Pro Phe Val Glu Ala Glu Lys
            20                  25                  30

Ser Asn Leu Ala Tyr Asp Ile Val Gln Trp Pro Thr Gly Leu Thr Gly
        35                  40                  45

Ile Lys Val Thr Tyr Met Glu Glu Glu Arg Asn Phe Thr Thr Glu Gln
    50                  55                  60

Val Thr Ala Met Leu Leu Ser Lys Leu Lys Glu Thr Ala Glu Ser Val
65                  70                  75                  80

Leu Lys Lys Pro Val Val
            85

<210> SEQ ID NO 16
<211> LENGTH: 43
<212> TYPE: PRT
<213> ORGANISM: Homo sapiens

<400> SEQUENCE: 16

Thr Trp Thr Leu Cys Gly Thr Pro Glu Tyr Leu Ala Pro Glu Ile Ile
1               5                   10                  15
Leu Ser Lys Gly Tyr Asn Lys Ala Val Asp Trp Trp Ala Leu Gly Val
                20                  25                  30
Leu Ile Tyr Glu Met Ala Ala Gly Tyr Pro Pro
            35                  40

<210> SEQ ID NO 17
<211> LENGTH: 18
<212> TYPE: PRT
<213> ORGANISM: Homo sapiens

<400> SEQUENCE: 17

Asp Trp Trp Ala Leu Gly Val Leu Ile Tyr Glu Met Ala Ala Gly Tyr
1               5                   10                  15
Pro Pro

<210> SEQ ID NO 18
<211> LENGTH: 19
<212> TYPE: PRT
<213> ORGANISM: Homo sapiens

<400> SEQUENCE: 18

Val Lys Lys Arg Asp Leu Glu Gln Ala Ile Ser Gln Arg Ile Gln Thr
1               5                   10                  15
Asn Asn Asn

<210> SEQ ID NO 19
<211> LENGTH: 21
<212> TYPE: PRT
<213> ORGANISM: Homo sapiens

<400> SEQUENCE: 19

Val Lys Glu Phe Leu Ala Lys Ala Lys Glu Asp Phe Leu Lys Lys Trp
1               5                   10                  15
Glu Ser Pro Ala Gln
                20

<210> SEQ ID NO 20
<211> LENGTH: 21
<212> TYPE: PRT
<213> ORGANISM: Homo sapiens

<400> SEQUENCE: 20

Leu Lys Lys Trp Glu Asn Pro Thr Gln Asn Asn Ala Gly Leu Glu Asp
1               5                   10                  15
Phe Glu Arg Lys Lys
                20

<210> SEQ ID NO 21
<211> LENGTH: 28
<212> TYPE: PRT
<213> ORGANISM: Homo sapiens

<400> SEQUENCE: 21

Asn Phe Thr Thr Glu Gln Val Thr Ala Met Leu Leu Ser Lys Leu Lys
1               5                   10                  15

Glu Thr Ala Glu Ser Val Leu Lys Lys Pro Val Val
            20                  25

<210> SEQ ID NO 22
<211> LENGTH: 21
<212> TYPE: PRT
<213> ORGANISM: Homo sapiens

<400> SEQUENCE: 22

Leu Lys Lys Trp Glu Ser Pro Ala Gln Asn Thr Ala His Leu Asp Gln
1               5                   10                  15

Phe Glu Arg Ile Lys
            20

<210> SEQ ID NO 23
<211> LENGTH: 29
<212> TYPE: PRT
<213> ORGANISM: Homo sapiens

<400> SEQUENCE: 23

Gly Asn Ala Ala Ala Lys Lys Gly Ser Glu Gln Glu Ser Val Lys
1               5                   10                  15

Glu Phe Leu Ala Lys Ala Lys Glu Asp Phe Leu Lys Lys
            20                  25

<210> SEQ ID NO 24
<211> LENGTH: 18
<212> TYPE: PRT
<213> ORGANISM: Homo sapiens

<400> SEQUENCE: 24

Phe Thr Asp Leu Ala Ser Val Asp Asn Ser Glu Phe Gln Gln Leu Leu
1               5                   10                  15

Asn Gln

<210> SEQ ID NO 25
<211> LENGTH: 25
<212> TYPE: PRT
<213> ORGANISM: Homo sapiens

<400> SEQUENCE: 25

Ser Thr Asp Pro Ala Val Phe Thr Asp Leu Ala Ser Val Asp Asn Ser
1               5                   10                  15

Glu Phe Gln Gln Leu Leu Asn Gln Gly
            20                  25

<210> SEQ ID NO 26
<211> LENGTH: 44
<212> TYPE: PRT
<213> ORGANISM: Homo sapiens

<400> SEQUENCE: 26

Gly Pro Gly Lys Glu Ser Pro Gly Gly Glu Val Lys Pro Pro Glu
1               5                   10                  15

Arg Arg Glu Pro Asp Gln Lys Ile Pro Gln Ala Pro Asn Thr Ser Ser
            20                  25                  30

Ser Asn Phe Leu Leu Pro Leu Ala Trp Phe Phe Arg
        35                  40

<210> SEQ ID NO 27
<211> LENGTH: 55
<212> TYPE: PRT
<213> ORGANISM: Homo sapiens

<400> SEQUENCE: 27

Ile Met Gln Asp Lys Leu Glu Lys Glu Arg Asn Asp Ala Lys Asn Ala
1               5                   10                  15

Val Glu Glu Tyr Val Tyr Glu Met Arg Asp Lys Leu Ser Gly Glu Tyr
                20                  25                  30

Glu Lys Phe Val Ser Glu Asp Arg Asn Ser Phe Thr Leu Lys Leu
            35                  40                  45

Glu Asp Thr Glu Asn Trp Leu
    50                  55

<210> SEQ ID NO 28
<211> LENGTH: 86
<212> TYPE: PRT
<213> ORGANISM: Homo sapiens

<400> SEQUENCE: 28

Lys Ser Gln Val Ile Ser Asn Ala Lys Asn Thr Val Gln Gly Phe Lys
1               5                   10                  15

Arg Phe His Gly Arg Ala Phe Ser Asp Pro Phe Val Glu Ala Glu Lys
                20                  25                  30

Ser Asn Leu Ala Tyr Asp Ile Val Gln Trp Pro Thr Gly Leu Thr Gly
            35                  40                  45

Ile Lys Val Thr Tyr Met Glu Glu Arg Asn Phe Thr Ile Glu Gln
    50                  55                  60

Val Thr Ala Met Leu Leu Ser Lys Leu Lys Glu Thr Ala Glu Ser Val
65                  70                  75                  80

Leu Lys Lys Pro Val Val
                85

<210> SEQ ID NO 29

<400> SEQUENCE: 29

000

<210> SEQ ID NO 30
<211> LENGTH: 34
<212> TYPE: PRT
<213> ORGANISM: Homo sapiens

<400> SEQUENCE: 30

Asp Asn Cys Leu Ala Ala Ala Leu Asn Gly Val Asp Arg Arg Ser
1               5                   10                  15

Leu Gln Arg Ser Ala Lys Leu Ala Leu Glu Val Leu Glu Arg Ala Lys
                20                  25                  30

Arg Arg

<210> SEQ ID NO 31
<211> LENGTH: 210
<212> TYPE: PRT
<213> ORGANISM: Homo sapiens

<400> SEQUENCE: 31

Met Asp Asn Cys Leu Ala Ala Ala Leu Asn Gly Val Asp Arg Arg
1               5                   10                  15

```
Ser Leu Gln Arg Ser Ala Arg Leu Ala Leu Glu Val Leu Glu Arg Ala
            20                  25                  30

Lys Arg Arg Ala Val Asp Trp His Ala Leu Glu Arg Pro Lys Gly Cys
        35                  40                  45

Met Gly Val Leu Ala Arg Glu Ala Pro His Leu Glu Lys Gln Pro Ala
 50                  55                  60

Ala Gly Pro Gln Arg Val Leu Pro Gly Glu Arg Glu Arg Pro Pro
65                  70                  75                  80

Thr Leu Ser Ala Ser Phe Arg Thr Met Ala Glu Phe Met Asp Tyr Thr
                85                  90                  95

Ser Ser Gln Cys Gly Lys Tyr Tyr Ser Val Pro Glu Glu Gly Gly
            100                 105                 110

Ala Thr His Val Tyr Arg Tyr His Arg Gly Glu Ser Lys Leu His Met
        115                 120                 125

Cys Leu Asp Ile Gly Asn Gly Gln Arg Lys Asp Arg Lys Lys Thr Ser
130                 135                 140

Leu Gly Pro Gly Gly Ser Tyr Gln Ile Ser Glu His Ala Pro Glu Ala
145                 150                 155                 160

Ser Gln Pro Ala Glu Asn Ile Ser Lys Asp Leu Tyr Ile Glu Val Tyr
                165                 170                 175

Pro Gly Thr Tyr Ser Val Thr Val Gly Ser Asn Asp Leu Thr Lys Lys
            180                 185                 190

Thr His Val Val Ala Val Asp Ser Gly Gln Ser Val Asp Leu Val Phe
        195                 200                 205

Pro Val
    210

<210> SEQ ID NO 32
<211> LENGTH: 840
<212> TYPE: PRT
<213> ORGANISM: Homo sapiens

<400> SEQUENCE: 32

Met Ser Val Val Gly Ile Asp Leu Gly Phe Gln Ser Cys Tyr Val Ala
1               5                   10                  15

Val Ala Arg Ala Gly Gly Ile Glu Thr Ile Ala Asn Glu Tyr Ser Asp
            20                  25                  30

Arg Cys Thr Pro Ala Cys Ile Ser Phe Gly Pro Lys Asn Arg Ser Ile
        35                  40                  45

Gly Ala Ala Ala Lys Ser Gln Val Ile Ser Asn Ala Lys Asn Thr Val
 50                  55                  60

Gln Gly Phe Lys Arg Phe His Gly Arg Ala Phe Ser Asp Pro Phe Val
65                  70                  75                  80

Glu Ala Glu Lys Ser Asn Leu Ala Tyr Asp Ile Val Gln Leu Pro Thr
                85                  90                  95

Gly Leu Thr Gly Ile Lys Val Thr Tyr Met Glu Glu Glu Arg Asn Phe
            100                 105                 110

Thr Thr Glu Gln Val Thr Ala Met Leu Leu Ser Lys Leu Lys Glu Thr
        115                 120                 125

Ala Glu Ser Val Leu Lys Lys Pro Val Val Asp Cys Val Val Ser Val
130                 135                 140

Pro Cys Phe Tyr Thr Asp Ala Glu Arg Arg Ser Val Met Asp Ala Thr
145                 150                 155                 160

Gln Ile Ala Gly Leu Asn Cys Leu Arg Leu Met Asn Glu Thr Thr Ala
```

```
                        165                 170                 175
Val Ala Leu Ala Tyr Gly Ile Tyr Lys Gln Asp Leu Pro Ala Leu Glu
                180                 185                 190
Glu Lys Pro Arg Asn Val Val Phe Val Asp Met Gly His Ser Ala Tyr
            195                 200                 205
Gln Val Ser Val Cys Ala Phe Asn Arg Gly Lys Leu Lys Val Leu Ala
        210                 215                 220
Thr Ala Phe Asp Thr Thr Leu Gly Gly Arg Lys Phe Asp Glu Val Leu
225                 230                 235                 240
Val Asn His Phe Cys Glu Glu Phe Gly Lys Lys Tyr Lys Leu Asp Ile
                245                 250                 255
Lys Ser Lys Ile Arg Ala Leu Arg Leu Ser Gln Glu Cys Glu Lys
            260                 265                 270
Leu Lys Lys Leu Met Ser Ala Asn Ala Ser Asp Leu Pro Leu Ser Ile
        275                 280                 285
Glu Cys Phe Met Asn Asp Val Asp Val Ser Gly Thr Met Asn Arg Gly
    290                 295                 300
Lys Phe Leu Glu Met Cys Asn Asp Leu Leu Ala Arg Val Glu Pro Pro
305                 310                 315                 320
Leu Arg Ser Val Leu Glu Gln Thr Lys Leu Lys Lys Glu Asp Ile Tyr
                325                 330                 335
Ala Val Glu Ile Val Gly Gly Ala Thr Arg Ile Pro Ala Val Lys Glu
            340                 345                 350
Lys Ile Ser Lys Phe Phe Gly Lys Glu Leu Ser Thr Thr Leu Asn Ala
        355                 360                 365
Asp Glu Ala Val Thr Arg Gly Cys Ala Leu Gln Cys Ala Ile Leu Ser
    370                 375                 380
Pro Ala Phe Lys Val Arg Glu Phe Ser Ile Thr Asp Val Val Pro Tyr
385                 390                 395                 400
Pro Ile Ser Leu Arg Trp Asn Ser Pro Ala Glu Glu Gly Ser Ser Asp
                405                 410                 415
Cys Glu Val Phe Ser Lys Asn His Ala Ala Pro Phe Ser Lys Val Leu
            420                 425                 430
Thr Phe Tyr Arg Lys Glu Pro Phe Thr Leu Glu Ala Tyr Tyr Ser Ser
        435                 440                 445
Pro Gln Asp Leu Pro Tyr Pro Asp Pro Ala Ile Ala Gln Phe Ser Val
    450                 455                 460
Gln Lys Val Thr Pro Gln Ser Asp Gly Ser Ser Ser Lys Val Lys Val
465                 470                 475                 480
Lys Val Arg Val Asn Val His Gly Ile Phe Ser Val Ser Ser Ala Ser
                485                 490                 495
Leu Val Glu Val His Lys Ser Glu Glu Asn Glu Pro Met Glu Thr
            500                 505                 510
Asp Gln Asn Ala Lys Glu Glu Lys Met Gln Val Asp Gln Glu Glu
        515                 520                 525
Pro His Val Glu Glu Gln Gln Gln Thr Pro Ala Glu Asn Lys Ala
    530                 535                 540
Glu Ser Glu Glu Met Glu Thr Ser Gln Ala Gly Ser Lys Asp Lys Lys
545                 550                 555                 560
Met Asp Gln Pro Pro Gln Ala Lys Lys Ala Lys Val Lys Thr Ser Thr
                565                 570                 575
Val Asp Leu Pro Ile Glu Asn Gln Leu Leu Trp Gln Ile Asp Arg Glu
            580                 585                 590
```

Met Leu Asn Leu Tyr Ile Glu Asn Glu Gly Lys Met Ile Met Gln Asp
            595                 600                 605

Lys Leu Glu Lys Glu Arg Asn Asp Ala Lys Asn Ala Val Glu Glu Tyr
        610                 615                 620

Val Tyr Glu Met Arg Asp Lys Leu Ser Gly Tyr Glu Lys Phe Val
625                 630                 635                 640

Ser Glu Asp Asp Arg Asn Ser Phe Thr Leu Lys Leu Glu Asp Thr Glu
                645                 650                 655

Asn Trp Leu Tyr Glu Asp Gly Glu Asp Gln Pro Lys Gln Val Tyr Val
            660                 665                 670

Asp Lys Leu Ala Glu Leu Lys Asn Leu Gly Gln Pro Ile Lys Ile Arg
        675                 680                 685

Phe Gln Glu Ser Glu Glu Arg Pro Lys Leu Phe Glu Glu Leu Gly Lys
    690                 695                 700

Gln Ile Gln Gln Tyr Met Lys Ile Ile Ser Ser Phe Lys Asn Lys Glu
705                 710                 715                 720

Asp Gln Tyr Asp His Leu Asp Ala Ala Asp Met Thr Lys Val Glu Lys
                725                 730                 735

Ser Thr Asn Glu Ala Met Glu Trp Met Asn Asn Lys Leu Asn Leu Gln
            740                 745                 750

Asn Lys Gln Ser Leu Thr Met Asp Pro Val Val Lys Ser Lys Glu Ile
        755                 760                 765

Glu Ala Lys Ile Lys Glu Leu Thr Ser Thr Cys Ser Pro Ile Ile Ser
    770                 775                 780

Lys Pro Lys Pro Lys Val Glu Pro Lys Glu Gln Lys Asn Ala
785                 790                 795                 800

Glu Gln Asn Gly Pro Val Asp Gly Gln Gly Asp Asn Pro Gly Pro Gln
            805                 810                 815

Ala Ala Glu Gln Gly Thr Asp Thr Ala Val Pro Ser Asp Ser Asp Lys
        820                 825                 830

Lys Leu Pro Glu Met Asp Ile Asp
    835                 840

<210> SEQ ID NO 33
<211> LENGTH: 550
<212> TYPE: PRT
<213> ORGANISM: Homo sapiens

<400> SEQUENCE: 33

Met Asp Glu Leu Phe Pro Leu Ile Phe Pro Ala Glu Pro Ala Gln Ala
1               5                   10                  15

Ser Gly Pro Tyr Val Glu Ile Ile Glu Gln Pro Lys Gln Arg Gly Met
            20                  25                  30

Arg Phe Arg Tyr Lys Cys Glu Gly Arg Ser Ala Gly Ser Ile Pro Gly
        35                  40                  45

Arg Arg Ser Thr Asp Thr Thr Lys Thr His Pro Thr Ile Lys Ile Asn
    50                  55                  60

Gly Tyr Thr Gly Pro Gly Thr Val Arg Ile Ser Leu Val Thr Lys Asp
65                  70                  75                  80

Pro Pro His Arg Pro His Pro His Glu Leu Val Gly Lys Asp Cys Arg
                85                  90                  95

Asp Gly Phe Tyr Glu Ala Glu Leu Cys Pro Asp Arg Cys Ile His Ser
            100                 105                 110

Phe Gln Asn Leu Gly Ile Gln Cys Val Lys Lys Arg Asp Leu Glu Gln

```
            115                 120                 125
Ala Ile Ser Gln Arg Ile Gln Thr Asn Asn Pro Phe Gln Val Pro
130                 135                 140
Ile Glu Glu Gln Arg Gly Asp Tyr Asp Leu Asn Ala Val Arg Leu Cys
145                 150                 155                 160
Phe Gln Val Thr Val Arg Asp Pro Ser Gly Arg Pro Leu Arg Leu Pro
                165                 170                 175
Pro Val Leu Ser His Pro Ile Phe Asp Asn Arg Ala Pro Asn Thr Ala
            180                 185                 190
Glu Leu Lys Ile Cys Arg Val Asn Arg Asn Ser Gly Ser Cys Leu Gly
            195                 200                 205
Gly Asp Glu Ile Phe Leu Leu Cys Asp Lys Val Gln Lys Glu Asp Ile
210                 215                 220
Glu Val Tyr Phe Thr Gly Pro Gly Trp Glu Ala Arg Gly Ser Phe Ser
225                 230                 235                 240
Gln Ala Asp Val His Arg Gln Val Ala Ile Val Phe Arg Thr Pro Pro
                245                 250                 255
Tyr Ala Asp Pro Ser Leu Gln Ala Pro Val Arg Val Ser Met Gln Leu
            260                 265                 270
Arg Arg Pro Ser Asp Arg Glu Leu Ser Glu Pro Met Glu Phe Gln Tyr
            275                 280                 285
Leu Pro Asp Thr Asp Asp Arg His Arg Ile Glu Glu Lys Arg Lys Arg
290                 295                 300
Thr Tyr Glu Thr Phe Lys Ser Ile Met Lys Lys Ser Pro Phe Ser Gly
305                 310                 315                 320
Pro Thr Asp Pro Arg Pro Pro Arg Arg Ile Ala Val Pro Ser Arg
                325                 330                 335
Ser Ser Ala Ser Val Pro Lys Pro Ala Pro Gln Pro Tyr Pro Phe Thr
            340                 345                 350
Ser Ser Leu Ser Thr Ile Asn Tyr Asp Glu Phe Pro Thr Met Val Phe
            355                 360                 365
Pro Ser Gly Arg Ser Ala Arg Pro Arg Leu Gly Pro Ala Pro Pro Gln
            370                 375                 380
Val Leu Pro Gln Ala Pro Ala Pro Ala Pro Ala Pro Ala Met Val Ser
385                 390                 395                 400
Ala Leu Ala Gln Ala Pro Ala Pro Val Pro Val Leu Ala Pro Gly Pro
                405                 410                 415
Pro Gln Ala Val Ala Pro Pro Ala Pro Lys Pro Thr Gln Ala Gly Glu
            420                 425                 430
Gly Thr Leu Ser Glu Ala Leu Leu Gln Leu Gln Phe Asp Asp Glu Asp
            435                 440                 445
Leu Gly Ala Leu Leu Gly Asn Ser Thr Asp Pro Ala Val Phe Thr Asp
            450                 455                 460
Leu Ala Ser Val Asp Asn Ser Glu Phe Gln Gln Leu Leu Asn Gln Gly
            465                 470                 475                 480
Ile Pro Val Ala Pro His Thr Thr Glu Pro Met Leu Met Glu Tyr Pro
                485                 490                 495
Glu Ala Ile Thr Arg Leu Val Thr Gly Ala Gln Arg Pro Pro Asp Pro
            500                 505                 510
Ala Pro Ala Pro Leu Gly Ala Pro Gly Leu Pro Asn Gly Leu Leu Ser
            515                 520                 525
Gly Asp Glu Asp Phe Ser Ser Ile Ala Asp Met Asp Phe Ser Ala Leu
            530                 535                 540
```

Leu Ser Gln Ile Ser Ser
545                 550

<210> SEQ ID NO 34
<211> LENGTH: 351
<212> TYPE: PRT
<213> ORGANISM: Homo sapiens

<400> SEQUENCE: 34

Met Gly Asn Ala Ala Thr Ala Lys Lys Gly Ser Glu Val Glu Ser Val
1               5                   10                  15

Lys Glu Phe Leu Ala Lys Ala Lys Glu Asp Phe Leu Lys Lys Trp Glu
            20                  25                  30

Asn Pro Thr Gln Asn Asn Ala Gly Leu Glu Asp Phe Glu Arg Lys Lys
        35                  40                  45

Thr Leu Gly Thr Gly Ser Phe Gly Arg Val Met Leu Val Lys His Lys
    50                  55                  60

Ala Thr Glu Gln Tyr Tyr Ala Met Lys Ile Leu Asp Lys Gln Lys Val
65                  70                  75                  80

Val Lys Leu Lys Gln Ile Glu His Thr Leu Asn Glu Lys Arg Ile Leu
                85                  90                  95

Gln Ala Val Asn Phe Pro Phe Leu Val Arg Leu Glu Tyr Ala Phe Lys
            100                 105                 110

Asp Asn Ser Asn Leu Tyr Met Val Met Glu Tyr Val Pro Gly Gly Glu
        115                 120                 125

Met Phe Ser His Leu Arg Arg Ile Gly Arg Phe Ser Glu Pro His Ala
    130                 135                 140

Arg Phe Tyr Ala Ala Gln Ile Val Leu Thr Phe Glu Tyr Leu His Ser
145                 150                 155                 160

Leu Asp Leu Ile Tyr Arg Asp Leu Lys Pro Glu Asn Leu Leu Ile Asp
                165                 170                 175

His Gln Gly Tyr Ile Gln Val Thr Asp Phe Gly Phe Ala Lys Arg Val
            180                 185                 190

Lys Gly Arg Thr Trp Thr Leu Cys Gly Thr Pro Glu Tyr Leu Ala Pro
        195                 200                 205

Glu Ile Ile Leu Ser Lys Gly Tyr Asn Lys Ala Val Asp Trp Trp Ala
    210                 215                 220

Leu Gly Val Leu Ile Tyr Glu Met Ala Ala Gly Tyr Pro Pro Phe Phe
225                 230                 235                 240

Ala Asp Gln Pro Ile Gln Ile Tyr Glu Lys Ile Val Ser Gly Lys Val
                245                 250                 255

Arg Phe Pro Ser His Phe Ser Ser Asp Leu Lys Asp Leu Leu Arg Asn
            260                 265                 270

Leu Leu Gln Val Asp Leu Thr Lys Arg Phe Gly Asn Leu Lys Asn Gly
        275                 280                 285

Val Ser Asp Ile Lys Thr His Lys Trp Phe Ala Thr Thr Asp Trp Ile
    290                 295                 300

Ala Ile Tyr Gln Arg Lys Val Glu Ala Pro Phe Ile Pro Lys Phe Arg
305                 310                 315                 320

Gly Ser Gly Asp Thr Ser Asn Phe Asp Asp Tyr Glu Glu Glu Asp Ile
                325                 330                 335

Arg Val Ser Ile Thr Glu Lys Cys Ala Lys Glu Phe Gly Glu Phe
            340                 345                 350

<210> SEQ ID NO 35
<211> LENGTH: 351
<212> TYPE: PRT
<213> ORGANISM: Homo sapiens

<400> SEQUENCE: 35

Met Gly Asn Ala Ala Ala Lys Lys Gly Ser Glu Gln Glu Ser Val
1               5                   10                  15

Lys Glu Phe Leu Ala Lys Ala Lys Glu Asp Phe Leu Lys Lys Trp Glu
                20                  25                  30

Ser Pro Ala Gln Asn Thr Ala His Leu Asp Gln Phe Glu Arg Ile Lys
                35                  40                  45

Thr Leu Gly Thr Gly Ser Phe Gly Arg Val Met Leu Val Lys His Lys
        50                  55                  60

Glu Thr Gly Asn His Tyr Ala Met Lys Ile Leu Asp Lys Gln Lys Val
65                  70                  75                  80

Val Lys Leu Lys Gln Ile Glu His Thr Leu Asn Glu Lys Arg Ile Leu
                85                  90                  95

Gln Ala Val Asn Phe Pro Phe Leu Val Lys Leu Glu Phe Ser Phe Lys
                100                 105                 110

Asp Asn Ser Asn Leu Tyr Met Val Met Glu Tyr Val Pro Gly Gly Glu
            115                 120                 125

Met Phe Ser His Leu Arg Arg Ile Gly Arg Phe Ser Glu Pro His Ala
    130                 135                 140

Arg Phe Tyr Ala Ala Gln Ile Val Leu Thr Phe Glu Tyr Leu His Ser
145                 150                 155                 160

Leu Asp Leu Ile Tyr Arg Asp Leu Lys Pro Glu Asn Leu Leu Ile Asp
                165                 170                 175

Gln Gln Gly Tyr Ile Gln Val Thr Asp Phe Gly Phe Ala Lys Arg Val
            180                 185                 190

Lys Gly Arg Thr Trp Thr Leu Cys Gly Thr Pro Glu Tyr Leu Ala Pro
        195                 200                 205

Glu Ile Ile Leu Ser Lys Gly Tyr Asn Lys Ala Val Asp Trp Trp Ala
210                 215                 220

Leu Gly Val Leu Ile Tyr Glu Met Ala Ala Gly Tyr Pro Pro Phe Phe
225                 230                 235                 240

Ala Asp Gln Pro Ile Gln Ile Tyr Glu Lys Ile Val Ser Gly Lys Val
                245                 250                 255

Arg Phe Pro Ser His Phe Ser Ser Asp Leu Lys Asp Leu Leu Arg Asn
            260                 265                 270

Leu Leu Gln Val Asp Leu Thr Lys Arg Phe Gly Asn Leu Lys Asn Gly
        275                 280                 285

Val Asn Asp Ile Lys Asn His Lys Trp Phe Ala Thr Thr Asp Trp Ile
290                 295                 300

Ala Ile Tyr Gln Arg Lys Val Glu Ala Pro Phe Ile Pro Lys Phe Lys
305                 310                 315                 320

Gly Pro Gly Asp Thr Ser Asn Phe Asp Asp Tyr Glu Glu Glu Glu Ile
                325                 330                 335

Arg Val Ser Ile Asn Glu Lys Cys Gly Lys Glu Phe Ser Glu Phe
            340                 345                 350

<210> SEQ ID NO 36
<211> LENGTH: 49
<212> TYPE: PRT
<213> ORGANISM: Homo sapiens -continued

<400> SEQUENCE: 36

Asn Ser Thr Asp Pro Ala Val Phe Thr Asp Leu Ala Ser Val Asp Asn
1               5                   10                  15

Ser Glu Phe Gln Gln Leu Leu Asn Gln Gly Ile Pro Val Ala Pro His
            20                  25                  30

Thr Thr Glu Pro Met Leu Met Glu Tyr Pro Glu Ala Ile Thr Arg Leu
        35                  40                  45

Val

<210> SEQ ID NO 37
<211> LENGTH: 30
<212> TYPE: PRT
<213> ORGANISM: Homo sapiens

<400> SEQUENCE: 37

Gly Asn Ser Thr Asp Pro Ala Val Phe Thr Asp Leu Ala Ser Val Asp
1               5                   10                  15

Asn Ser Glu Phe Gln Gln Leu Leu Asn Gln Gly Ile Pro Val
            20                  25                  30

<210> SEQ ID NO 38
<211> LENGTH: 15
<212> TYPE: PRT
<213> ORGANISM: Homo sapiens

<400> SEQUENCE: 38

Pro Ala Val Phe Thr Asp Leu Ala Ser Val Asp Asn Ser Glu Phe
1               5                   10                  15

<210> SEQ ID NO 39
<211> LENGTH: 15
<212> TYPE: PRT
<213> ORGANISM: Homo sapiens

<400> SEQUENCE: 39

Ala Val Phe Thr Asp Leu Ala Ser Val Asp Asn Ser Glu Phe Gln
1               5                   10                  15

<210> SEQ ID NO 40
<211> LENGTH: 15
<212> TYPE: PRT
<213> ORGANISM: Homo sapiens

<400> SEQUENCE: 40

Val Phe Thr Asp Leu Ala Ser Val Asp Asn Ser Glu Phe Gln Gln
1               5                   10                  15

<210> SEQ ID NO 41
<211> LENGTH: 15
<212> TYPE: PRT
<213> ORGANISM: Homo sapiens

<400> SEQUENCE: 41

Phe Thr Asp Leu Ala Ser Val Asp Asn Ser Glu Phe Gln Gln Leu
1               5                   10                  15

<210> SEQ ID NO 42
<211> LENGTH: 15
<212> TYPE: PRT
<213> ORGANISM: Homo sapiens

<400> SEQUENCE: 42

```
Thr Asp Leu Ala Ser Val Asp Asn Ser Glu Phe Gln Gln Leu Leu
1               5                   10                  15

<210> SEQ ID NO 43
<211> LENGTH: 15
<212> TYPE: PRT
<213> ORGANISM: Homo sapiens

<400> SEQUENCE: 43

Asp Leu Ala Ser Val Asp Asn Ser Glu Phe Gln Gln Leu Leu Asn
1               5                   10                  15

<210> SEQ ID NO 44
<211> LENGTH: 15
<212> TYPE: PRT
<213> ORGANISM: Homo sapiens

<400> SEQUENCE: 44

Leu Ala Ser Val Asp Asn Ser Glu Phe Gln Gln Leu Leu Asn Gln
1               5                   10                  15

<210> SEQ ID NO 45
<211> LENGTH: 15
<212> TYPE: PRT
<213> ORGANISM: Homo sapiens

<400> SEQUENCE: 45

Ala Ser Val Asp Asn Ser Glu Phe Gln Gln Leu Leu Asn Gln Gly
1               5                   10                  15

<210> SEQ ID NO 46
<211> LENGTH: 27
<212> TYPE: PRT
<213> ORGANISM: Homo sapiens

<400> SEQUENCE: 46

Lys Tyr Tyr Ser Ser Val Pro Glu Gly Gly Ala Thr His Val Tyr
1               5                   10                  15

Arg Tyr His Arg Gly Glu Ser Lys Leu His Met
            20                  25

<210> SEQ ID NO 47
<211> LENGTH: 42
<212> TYPE: PRT
<213> ORGANISM: Homo sapiens

<400> SEQUENCE: 47

Tyr Thr Ser Ser Gln Cys Gly Lys Tyr Tyr Ser Ser Val Pro Glu Glu
1               5                   10                  15

Gly Gly Ala Thr His Val Tyr Arg Tyr His Arg Gly Glu Ser Lys Leu
            20                  25                  30

His Met Cys Leu Asp Ile Gly Asn Gly Gln
            35                  40

<210> SEQ ID NO 48
<211> LENGTH: 18
<212> TYPE: PRT
<213> ORGANISM: Homo sapiens

<400> SEQUENCE: 48

Glu Gly Gly Ala Thr His Val Tyr Arg Tyr His Arg Gly Glu Ser Lys
1               5                   10                  15

Leu His
```

<210> SEQ ID NO 49
<211> LENGTH: 18
<212> TYPE: PRT
<213> ORGANISM: Homo sapiens

<400> SEQUENCE: 49

Gly Gly Ala Thr His Val Tyr Arg Tyr His Arg Gly Glu Ser Lys Leu
1               5                   10                  15

His Met

<210> SEQ ID NO 50
<211> LENGTH: 18
<212> TYPE: PRT
<213> ORGANISM: Homo sapiens

<400> SEQUENCE: 50

Gly Ala Thr His Val Tyr Arg Arg His Arg Gly Glu Ser Lys Leu His
1               5                   10                  15

Met Cys

<210> SEQ ID NO 51
<211> LENGTH: 18
<212> TYPE: PRT
<213> ORGANISM: Homo sapiens

<400> SEQUENCE: 51

Ala Thr His Val Tyr Arg Tyr His Arg Gly Glu Ser Lys Leu His Met
1               5                   10                  15

Cys Leu

<210> SEQ ID NO 52
<211> LENGTH: 18
<212> TYPE: PRT
<213> ORGANISM: Homo sapiens

<400> SEQUENCE: 52

Thr His Val Tyr Arg Tyr His Arg Gly Glu Ser Lys Leu His Met Cys
1               5                   10                  15

Leu Asp

<210> SEQ ID NO 53
<211> LENGTH: 18
<212> TYPE: PRT
<213> ORGANISM: Homo sapiens

<400> SEQUENCE: 53

His Val Tyr Arg Tyr His Arg Gly Glu Ser Lys Leu His Met Cys Leu
1               5                   10                  15

Asp Ile

<210> SEQ ID NO 54
<211> LENGTH: 18
<212> TYPE: PRT
<213> ORGANISM: Homo sapiens

<400> SEQUENCE: 54

Val Tyr Arg Tyr His Arg Gly Glu Ser Lys Leu His Met Cys Leu Asp
1               5                   10                  15

Ile Gly

<210> SEQ ID NO 55
<211> LENGTH: 18
<212> TYPE: PRT
<213> ORGANISM: Homo sapiens

<400> SEQUENCE: 55

```
Tyr Arg Tyr His Arg Gly Glu Ser Lys Leu His Met Cys Leu Asp Ile
 1               5                  10                  15

Gly Asn
```

<210> SEQ ID NO 56
<211> LENGTH: 18
<212> TYPE: PRT
<213> ORGANISM: Homo sapiens

<400> SEQUENCE: 56

```
Arg Tyr His Arg Gly Glu Ser Lys Leu His Met Cys Leu Asp Ile Gly
 1               5                  10                  15

Asn Gly
```

<210> SEQ ID NO 57
<211> LENGTH: 18
<212> TYPE: PRT
<213> ORGANISM: Homo sapiens

<400> SEQUENCE: 57

```
Tyr His Arg Gly Glu Ser Lys Leu His Met Cys Leu Asp Ile Gly Asn
 1               5                  10                  15

Gly Gln
```

<210> SEQ ID NO 58
<211> LENGTH: 304
<212> TYPE: PRT
<213> ORGANISM: Homo sapiens

<400> SEQUENCE: 58

```
Met Ala Ala Tyr Arg Glu Pro Pro Cys Asn Gln Tyr Thr Gly Thr Thr
 1               5                  10                  15

Thr Ala Leu Gln Lys Leu Glu Gly Phe Ala Ser Arg Leu Phe His Arg
             20                  25                  30

His Ser Lys Gly Thr Ala His Asp Gln Lys Thr Ala Leu Glu Asn Asp
         35                  40                  45

Ser Leu His Phe Ser Glu His Thr Ala Leu Trp Asp Arg Ser Met Lys
     50                  55                  60

Glu Phe Leu Ala Lys Ala Lys Glu Asp Phe Leu Lys Lys Trp Glu Asn
 65                  70                  75                  80

Pro Thr Gln Asn Asn Ala Gly Leu Glu Asp Phe Glu Arg Lys Lys Thr
                 85                  90                  95

Leu Gly Thr Gly Ser Phe Gly Arg Val Met Leu Val Lys His Lys Ala
            100                 105                 110

Thr Glu Gln Tyr Tyr Ala Met Lys Ile Leu Asp Lys Gln Lys Val Val
        115                 120                 125

Lys Leu Lys Gln Ile Glu His Thr Leu Asn Glu Lys Arg Ile Leu Gln
    130                 135                 140

Ala Val Asn Phe Pro Phe Leu Val Arg Leu Glu Tyr Ala Phe Lys Asp
145                 150                 155                 160

Asn Ser Asn Leu Tyr Met Val Met Glu Tyr Val Pro Gly Gly Glu Met
                165                 170                 175
```

```
Phe Ser His Leu Arg Arg Ile Gly Arg Phe Ser Glu Pro His Ala Arg
                180                 185                 190

Phe Tyr Ala Ala Gln Ile Val Leu Thr Phe Glu Tyr Leu His Ser Leu
            195                 200                 205

Asp Leu Ile Tyr Arg Asp Leu Lys Pro Glu Asn Leu Leu Ile Asp His
        210                 215                 220

Gln Gly Tyr Ile Gln Val Thr Asp Phe Gly Phe Ala Lys Arg Val Lys
225                 230                 235                 240

Gly Arg Thr Trp Thr Leu Cys Gly Thr Pro Glu Tyr Leu Ala Pro Glu
                245                 250                 255

Ile Ile Leu Ser Lys Gly Tyr Asn Lys Ala Val Asp Trp Trp Ala Leu
            260                 265                 270

Gly Val Leu Ile Tyr Glu Met Ala Ala Gly Tyr Pro Pro Phe Phe Ala
        275                 280                 285

Asp Gln Pro Ile Gln Ile Tyr Glu Lys Ile Val Ser Gly Lys Asn Phe
290                 295                 300
```

<210> SEQ ID NO 59
<211> LENGTH: 357
<212> TYPE: PRT
<213> ORGANISM: Homo sapiens

<400> SEQUENCE: 59

```
Met Ser Ala Arg Lys Ser Ser Asp Ala Ser Ala Cys Ser Ser Ser Glu
1               5                   10                  15

Ile Ser Asp Ser Phe Val Lys Glu Phe Leu Ala Lys Ala Lys Glu Asp
                20                  25                  30

Phe Leu Lys Lys Trp Glu Asn Pro Thr Gln Asn Asn Ala Gly Leu Glu
            35                  40                  45

Asp Phe Glu Arg Lys Lys Thr Leu Gly Thr Gly Ser Phe Gly Arg Val
        50                  55                  60

Met Leu Val Lys His Lys Ala Thr Glu Gln Tyr Tyr Ala Met Lys Ile
65                  70                  75                  80

Leu Asp Lys Gln Lys Val Val Lys Leu Lys Gln Ile Glu His Thr Leu
                85                  90                  95

Asn Glu Lys Arg Ile Leu Gln Ala Val Asn Phe Pro Phe Leu Val Arg
            100                 105                 110

Leu Glu Tyr Ala Phe Lys Asp Asn Ser Asn Leu Tyr Met Val Met Glu
        115                 120                 125

Tyr Val Pro Gly Gly Glu Met Phe Ser His Leu Arg Arg Ile Gly Arg
130                 135                 140

Phe Ser Glu Pro His Ala Arg Phe Tyr Ala Ala Gln Ile Val Leu Thr
145                 150                 155                 160

Phe Glu Tyr Leu His Ser Leu Asp Leu Ile Tyr Arg Asp Leu Lys Pro
                165                 170                 175

Glu Asn Leu Leu Ile Asp His Gln Gly Tyr Ile Gln Val Thr Asp Phe
            180                 185                 190

Gly Phe Ala Lys Arg Val Lys Gly Arg Thr Trp Thr Leu Cys Gly Thr
        195                 200                 205

Pro Glu Tyr Leu Ala Pro Glu Ile Ile Leu Ser Lys Gly Tyr Asn Lys
    210                 215                 220

Ala Val Asp Trp Trp Ala Leu Gly Val Leu Ile Tyr Glu Met Ala Ala
225                 230                 235                 240

Gly Tyr Pro Pro Phe Phe Ala Asp Gln Pro Ile Gln Ile Tyr Glu Lys
```

```
                        245                 250                 255
Ile Val Ser Gly Lys Val Arg Phe Pro Ser His Phe Ser Ser Asp Leu
                260                 265                 270

Lys Asp Leu Leu Arg Asn Leu Leu Gln Val Asp Leu Thr Lys Arg Phe
            275                 280                 285

Gly Asn Leu Lys Asn Gly Val Ser Asp Ile Lys Thr His Lys Trp Phe
        290                 295                 300

Ala Thr Thr Asp Trp Ile Ala Ile Tyr Gln Arg Lys Val Glu Ala Pro
305                 310                 315                 320

Phe Ile Pro Lys Phe Arg Gly Ser Gly Asp Thr Ser Asn Phe Asp Asp
                325                 330                 335

Tyr Glu Glu Glu Asp Ile Arg Val Ser Ile Thr Glu Lys Cys Ala Lys
            340                 345                 350

Glu Phe Gly Glu Phe
            355

<210> SEQ ID NO 60
<211> LENGTH: 210
<212> TYPE: PRT
<213> ORGANISM: Homo sapiens

<400> SEQUENCE: 60

Met Asp Asn Cys Leu Ala Ala Ala Leu Asn Gly Val Asp Arg Arg
1               5                   10                  15

Ser Leu Gln Arg Ser Ala Lys Leu Ala Leu Glu Val Leu Glu Arg Ala
                20                  25                  30

Lys Arg Arg Ala Val Asp Trp His Ala Leu Glu Arg Pro Lys Gly Cys
            35                  40                  45

Met Gly Val Leu Ala Arg Glu Ala Pro His Leu Glu Lys Gln Pro Ala
        50                  55                  60

Ala Gly Pro Gln Arg Val Leu Pro Gly Glu Arg Glu Glu Arg Pro Pro
65                  70                  75                  80

Thr Leu Ser Ala Ser Phe Arg Thr Met Ala Glu Phe Met Asp Tyr Thr
                85                  90                  95

Ser Ser Gln Cys Gly Lys Tyr Tyr Ser Ser Val Pro Glu Glu Gly Gly
                100                 105                 110

Ala Thr His Val Tyr Arg Tyr His Arg Gly Glu Ser Leu Lys His Met
            115                 120                 125

Cys Leu Asp Ile Gly Asn Gly Gln Arg Lys Asp Arg Lys Lys Thr Ser
130                 135                 140

Leu Gly Pro Gly Gly Ser Tyr Gln Ile Ser Glu His Ala Pro Glu Ala
145                 150                 155                 160

Ser Gln Pro Ala Glu Asn Ile Ser Lys Asp Leu Tyr Ile Glu Val Tyr
                165                 170                 175

Pro Gly Thr Tyr Ser Val Thr Val Gly Ser Asn Asp Leu Thr Lys Lys
            180                 185                 190

Thr His Val Val Ala Val Asp Ser Gly Gln Ser Val Asp Leu Val Phe
        195                 200                 205

Phe Val
    210

<210> SEQ ID NO 61
<211> LENGTH: 183
<212> TYPE: PRT
<213> ORGANISM: Homo sapiens
```

<400> SEQUENCE: 61

Met Asp Asn Cys Leu Ala Ala Ala Leu Asn Gly Val Asp Arg Arg
1               5                   10                  15

Ser Leu Gln Arg Ser Ala Lys Leu Ala Leu Glu Val Leu Glu Arg Ala
            20                  25                  30

Lys Arg Arg Ala Val Asp Trp His Ala Leu Glu Arg Pro Lys Gly Cys
        35                  40                  45

Met Gly Val Leu Ala Arg Glu Ala Pro His Leu Glu Lys Gln Pro Ala
    50                  55                  60

Ala Gly Pro Gln Arg Val Leu Pro Gly Glu Lys Tyr Tyr Ser Ser Val
65                  70                  75                  80

Pro Glu Glu Gly Gly Ala Thr His Val Tyr Arg Tyr His Arg Gly Glu
                85                  90                  95

Ser Lys Leu His Met Cys Leu Asp Ile Gly Asn Gly Gln Arg Lys Asp
            100                 105                 110

Arg Lys Lys Thr Ser Leu Gly Pro Gly Gly Ser Tyr Gln Ile Ser Glu
        115                 120                 125

His Ala Pro Glu Ala Ser Gln Pro Ala Glu Asn Ile Ser Lys Asp Leu
    130                 135                 140

Tyr Ile Glu Val Tyr Pro Gly Thr Tyr Ser Val Thr Val Gly Ser Asn
145                 150                 155                 160

Asp Leu Thr Lys Lys Thr His Val Val Ala Val Asp Ser Gly Gln Ser
                165                 170                 175

Val Asp Leu Val Phe Pro Val
            180

<210> SEQ ID NO 62
<211> LENGTH: 155
<212> TYPE: PRT
<213> ORGANISM: Homo sapiens

<400> SEQUENCE: 62

Met Asp Asn Cys Leu Ala Ala Ala Leu Asn Gly Val Asp Arg Arg
1               5                   10                  15

Ser Leu Gln Arg Ser Ala Lys Leu Ala Leu Glu Val Leu Glu Arg Ala
            20                  25                  30

Lys Arg Arg Ala Val Asp Trp His Ala Leu Glu Arg Pro Lys Gly Cys
        35                  40                  45

Met Gly Val Leu Ala Arg Glu Ala Pro His Leu Glu Lys Gln Pro Ala
    50                  55                  60

Ala Gly Pro Gln Arg Val Leu Pro Gly Glu Lys Tyr Tyr Ser Ser Val
65                  70                  75                  80

Pro Glu Glu Gly Gly Ala Thr His Val Tyr Arg Tyr His Arg Gly Glu
                85                  90                  95

Ser Lys Leu His Met Cys Leu Asp Ile Gly Asn Gly Gln Ala Glu Asn
            100                 105                 110

Ile Ser Lys Asp Leu Tyr Ile Glu Val Tyr Pro Gly Thr Tyr Ser Thr
        115                 120                 125

Val Gly Ser Asn Asp Leu Thr Lys Lys Thr His Val Val Ala Val Asp
    130                 135                 140

Ser Gly Gln Ser Val Asp Leu Val Phe Pro Val
145                 150                 155

<210> SEQ ID NO 63
<211> LENGTH: 183

<212> TYPE: PRT
<213> ORGANISM: Homo sapiens

<400> SEQUENCE: 63

Met Asp Asn Cys Leu Ala Ala Ala Leu Asn Gly Val Asp Arg Arg
1               5                   10                  15

Ser Leu Gln Arg Ser Ala Lys Leu Ala Leu Glu Val Leu Glu Arg Ala
            20                  25                  30

Lys Arg Arg Ala Val Asp Trp His Ala Leu Glu Arg Pro Lys Gly Cys
        35                  40                  45

Met Gly Val Leu Ala Arg Glu Ala Pro His Leu Glu Lys Gln Pro Ala
    50                  55                  60

Ala Gly Pro Gln Arg Val Leu Pro Gly Glu Arg Glu Arg Pro Pro
65                  70                  75                  80

Thr Leu Ser Ala Ser Phe Met Thr Met Ala Glu Phe Met Asp Ile Thr
                85                  90                  95

Ser Ser Gln Cys Gly Lys Tyr Tyr Ser Ser Val Pro Glu Glu Gly Gly
            100                 105                 110

Ala Thr His Val Tyr Lys Tyr His Arg Gly Glu Ser Lys Leu His Met
        115                 120                 125

Cys Leu Asp Ile Gly Asn Gly Gln Ala Glu Asn Ile Ser Lys Asp Leu
    130                 135                 140

Tyr Ile Glu Val Tyr Pro Gly Thr Tyr Ser Val Thr Val Gly Ser Asn
145                 150                 155                 160

Asp Leu Thr Lys Lys Thr His Val Val Ala Val Asp Ser Gly Gln Ser
                165                 170                 175

Val Asp Leu Val Phe Pro Val
            180

<210> SEQ ID NO 64
<211> LENGTH: 212
<212> TYPE: PRT
<213> ORGANISM: Homo sapiens

<400> SEQUENCE: 64

Met Glu Tyr Cys Leu Ala Ala Ala Leu Asn Gly Val Asp Arg Arg
1               5                   10                  15

Ser Leu Gln Arg Ser Ala Arg Leu Gly Arg Glu Val Leu Glu Arg Ala
            20                  25                  30

Lys Arg Arg Ala Val Asp Trp His Ser Pro Glu Arg Ser Arg Gly Asn
        35                  40                  45

Val Gly Val Leu Tyr Arg Gln Gly Pro Tyr Gln Glu Arg Trp Ser Val
    50                  55                  60

Pro Gly Ser Gln Arg Leu Leu Gly Glu Arg Glu Arg Cys Pro Thr
65                  70                  75                  80

Leu Ser Ser Ser Phe Gly Ala Met Ala Glu Phe Met Asp Tyr Ser
                85                  90                  95

Ser Gln Cys Gly Lys Tyr Tyr Leu Ser Met Pro Glu Glu Gly Gly Ala
            100                 105                 110

Thr His Val Tyr Arg Tyr His Arg Arg Lys Pro Pro Glu Met His Met
        115                 120                 125

Tyr Ser Asp Thr Gly His Ser Gln Glu Gln Arg Asn Cys Arg Gly Glu
    130                 135                 140

Thr Ser Val Gly Gln Glu Ser Ile Tyr Gln Thr Ser Glu His Ser Gln
145                 150                 155                 160

```
Glu Ser Ser Trp Pro Thr Glu Asn Ile Ser Lys Asp Leu Tyr Ile Glu
                165                 170                 175

Val Tyr Pro Gly Thr Tyr Ser Val Thr Val Gly Ser Ser Ala Leu Ser
            180                 185                 190

Lys Lys Thr His Val Val Ala Val Asp Pro Gly Gln Ser Val Asp Leu
            195                 200                 205

Val Phe Pro Phe
    210

<210> SEQ ID NO 65
<211> LENGTH: 212
<212> TYPE: PRT
<213> ORGANISM: Homo sapiens

<400> SEQUENCE: 65

Met Glu Tyr Cys Leu Ala Ala Ala Leu Asn Ala Val Asp Arg Arg
1               5                   10                  15

Ser Leu Gln Arg Ser Ala Arg Leu Gly Arg Glu Val Leu Glu Arg Ala
            20                  25                  30

Lys Arg Arg Ala Val Asp Trp His Ser Pro Glu Arg Ser Arg Gly Cys
        35                  40                  45

Val Gly Val Leu Tyr Gly Gln Asp Pro Tyr Gln Glu Arg Trp Ser Val
    50                  55                  60

Pro Gly Pro Gln Ser Leu Leu Gly Glu Arg Glu Arg Arg Pro Thr
65                  70                  75                  80

Leu Ser Thr Ser Phe Arg Thr Met Ala Glu Pro Met Asp Tyr Thr Ser
                85                  90                  95

Ser Gln Cys Gly Lys Tyr Tyr Leu Ser Thr Pro Glu Glu Gly Gly Ala
            100                 105                 110

Thr His Val Tyr Arg Tyr His Arg Arg Lys Pro Ala Glu Val His Val
        115                 120                 125

Cys Ser Asp Ser Gly His Arg Glu Ala Gln Arg Asn Cys Arg Gly Glu
    130                 135                 140

Thr Ser Val Gly Pro Gly Ser Ile Tyr Gln Thr Ser Glu His Ser Gln
145                 150                 155                 160

Glu Ser Ser Trp Pro Ile Glu Asn Ile Ser Lys Asp Leu Tyr Ile Glu
                165                 170                 175

Val Tyr Pro Gly Thr Tyr Ser Val Thr Val Gly Ser Asn Asp Leu Thr
            180                 185                 190

Lys Lys Thr His Val Val Ala Val Asp Ser Gly Gln Ser Val Asp Leu
            195                 200                 205

Val Phe Pro Val
    210

<210> SEQ ID NO 66
<211> LENGTH: 39
<212> TYPE: PRT
<213> ORGANISM: Homo sapiens

<400> SEQUENCE: 66

Met Ala Lys Arg Gly Ala Arg Ser Thr Ala Gly Asn Ala Ala Ala
1               5                   10                  15

Lys Lys Gly Ser Glu Gln Glu Ser Val Lys Glu Phe Leu Ala Lys Ala
            20                  25                  30

Lys Glu Asp Phe Leu Lys Lys
        35
```

<210> SEQ ID NO 67
<211> LENGTH: 351
<212> TYPE: PRT
<213> ORGANISM: Homo sapiens

<400> SEQUENCE: 67

Met Gly Asn Ala Ala Ala Lys Lys Gly Ser Glu Gln Glu Ser Val
1               5                   10                  15

Lys Glu Phe Leu Ala Lys Ala Lys Glu Asp Phe Leu Lys Lys Trp Glu
            20                  25                  30

Ser Pro Ala Gln Asn Thr Ala His Leu Asp Gln Phe Glu Arg Ile Lys
        35                  40                  45

Thr Leu Gly Thr Gly Ser Phe Gly Arg Val Met Leu Val Lys His Lys
50                  55                  60

Glu Thr Gly Asn His Tyr Ala Met Lys Ile Leu Asp Lys Gln Lys Val
65                  70                  75                  80

Val Lys Leu Lys Gln Ile Glu His Thr Leu Asn Glu Lys Arg Ile Leu
            85                  90                  95

Gln Ala Val Asn Phe Pro Phe Leu Val Lys Leu Glu Phe Ser Phe Lys
            100                 105                 110

Asp Asn Ser Asn Leu Tyr Met Val Met Glu Tyr Val Pro Gly Gly Glu
            115                 120                 125

Met Phe Ser His Leu Arg Arg Ile Gly Arg Phe Ser Glu Pro Lys Ala
        130                 135                 140

Arg Phe Tyr Ala Ala Gln Ile Val Leu Tyr Phe Glu Tyr Leu His Ser
145                 150                 155                 160

Leu Asp Leu Ile Tyr Arg Asp Leu Lys Pro Glu Asn Leu Leu Ile Asp
                165                 170                 175

Gln Gln Gly Tyr Ile Gln Val Thr Asp Phe Gly Phe Ala Lys Arg Val
            180                 185                 190

Lys Gly Arg Thr Trp Thr Leu Cys Gly Thr Pro Glu Tyr Leu Ala Pro
        195                 200                 205

Glu Ile Ile Leu Ser Lys Gly Tyr Asn Lys Ala Val Asp Trp Trp Ala
    210                 215                 220

Leu Gly Val Leu Ile Tyr Glu Met Ala Ala Gly Tyr Pro Pro Phe Phe
225                 230                 235                 240

Ala Asp Gln Pro Ile Gln Ile Tyr Glu Lys Ile Val Ser Gly Lys Val
                245                 250                 255

Arg Phe Pro Ser His Phe Ser Ser Asp Leu Lys Asp Leu Leu Arg Asn
            260                 265                 270

Leu Leu Gln Val Asp Leu Thr Lys Arg Phe Gly Asn Leu Lys Asn Gly
        275                 280                 285

Val Asn Asp Ile Lys Asn His Lys Trp Phe Ala Thr Thr Asp Trp Ile
    290                 295                 300

Ala Ile Tyr Gln Arg Lys Val Glu Ala Pro Phe Ile Pro Lys Phe Lys
305                 310                 315                 320

Gly Pro Gly Asp Thr Ser Asn Phe Asp Asp Tyr Glu Glu Glu Glu Ile
                325                 330                 335

Arg Val Ser Ile Asn Glu Lys Cys Gly Lys Glu Phe Ser Glu Phe
            340                 345                 350

<210> SEQ ID NO 68
<211> LENGTH: 30
<212> TYPE: PRT
<213> ORGANISM: Homo sapiens -continued

<400> SEQUENCE: 68

Gly Asn Ala Ala Ala Lys Lys Gly Ser Glu Gln Glu Ser Val Lys
1               5                   10                  15

Glu Phe Leu Ala Lys Ala Lys Glu Asp Phe Leu Lys Lys Trp
            20                  25                  30

<210> SEQ ID NO 69
<211> LENGTH: 15
<212> TYPE: PRT
<213> ORGANISM: Homo sapiens

<400> SEQUENCE: 69

Lys Lys Gly Ser Glu Gln Glu Ser Val Lys Glu Phe Leu Ala Lys
1               5                   10                  15

<210> SEQ ID NO 70
<211> LENGTH: 15
<212> TYPE: PRT
<213> ORGANISM: Homo sapiens

<400> SEQUENCE: 70

Lys Gly Ser Glu Gln Glu Ser Val Lys Glu Phe Leu Ala Lys Ala
1               5                   10                  15

<210> SEQ ID NO 71
<211> LENGTH: 15
<212> TYPE: PRT
<213> ORGANISM: Homo sapiens

<400> SEQUENCE: 71

Gly Ser Glu Gln Glu Ser Val Lys Glu Phe Leu Ala Lys Ala Lys
1               5                   10                  15

<210> SEQ ID NO 72
<211> LENGTH: 15
<212> TYPE: PRT
<213> ORGANISM: Homo sapiens

<400> SEQUENCE: 72

Ser Glu Gln Glu Ser Val Lys Glu Phe Leu Ala Lys Ala Lys Glu
1               5                   10                  15

<210> SEQ ID NO 73
<211> LENGTH: 15
<212> TYPE: PRT
<213> ORGANISM: Homo sapiens

<400> SEQUENCE: 73

Glu Gln Glu Ser Val Lys Glu Phe Leu Ala Lys Ala Lys Glu Asp
1               5                   10                  15

<210> SEQ ID NO 74
<211> LENGTH: 15
<212> TYPE: PRT
<213> ORGANISM: Homo sapiens

<400> SEQUENCE: 74

Gln Glu Ser Val Lys Glu Phe Leu Ala Lys Ala Lys Glu Asp Phe
1               5                   10                  15

<210> SEQ ID NO 75
<211> LENGTH: 15
<212> TYPE: PRT

<213> ORGANISM: Homo sapiens

<400> SEQUENCE: 75

Glu Ser Val Lys Glu Phe Leu Ala Lys Ala Lys Glu Asp Phe Leu
1               5                   10                  15

<210> SEQ ID NO 76
<211> LENGTH: 15
<212> TYPE: PRT
<213> ORGANISM: Homo sapiens

<400> SEQUENCE: 76

Ser Val Lys Glu Phe Leu Ala Lys Ala Lys Glu Asp Phe Leu Lys
1               5                   10                  15

<210> SEQ ID NO 77
<211> LENGTH: 15
<212> TYPE: PRT
<213> ORGANISM: Homo sapiens

<400> SEQUENCE: 77

Val Lys Glu Phe Leu Ala Lys Ala Lys Glu Asp Phe Leu Lys Lys
1               5                   10                  15

<210> SEQ ID NO 78
<211> LENGTH: 15
<212> TYPE: PRT
<213> ORGANISM: Homo sapiens

<400> SEQUENCE: 78

Lys Glu Phe Leu Ala Lys Ala Lys Glu Asp Phe Leu Lys Lys Trp
1               5                   10                  15

<210> SEQ ID NO 79
<211> LENGTH: 31
<212> TYPE: PRT
<213> ORGANISM: Homo sapiens

<400> SEQUENCE: 79

Met Ala Lys Arg Gly Ala Arg Ser Thr Ala Val Lys Glu Phe Leu Ala
1               5                   10                  15

Lys Ala Lys Glu Asp Phe Leu Lys Lys Trp Glu Ser Pro Ala Gln
            20                  25                  30

<210> SEQ ID NO 80
<211> LENGTH: 351
<212> TYPE: PRT
<213> ORGANISM: Homo sapiens

<400> SEQUENCE: 80

Met Gly Asn Ala Ala Ala Ala Lys Lys Gly Ser Glu Gln Glu Ser Val
1               5                   10                  15

Lys Glu Phe Leu Ala Lys Ala Lys Glu Asp Phe Leu Lys Lys Trp Glu
            20                  25                  30

Ser Pro Ala Gln Asn Thr Ala His Leu Asp Gln Phe Glu Arg Ile Lys
        35                  40                  45

Thr Leu Gly Thr Gly Ser Phe Gly Arg Val Met Leu Val Lys His Lys
    50                  55                  60

Glu Thr Gly Asn His Tyr Ala Met Lys Ile Leu Asp Lys Gln Lys Val
65                  70                  75                  80

Val Lys Leu Lys Gln Ile Glu His Thr Leu Asn Glu Lys Arg Ile Leu
                85                  90                  95

-continued

```
Gln Ala Val Asn Phe Pro Phe Leu Val Lys Leu Glu Phe Ser Phe Lys
            100                 105                 110

Asp Asn Ser Asn Leu Tyr Met Val Met Glu Tyr Val Pro Gly Gly Glu
            115                 120                 125

Met Phe Ser His Leu Arg Arg Ile Gly Arg Phe Ser Glu Pro Lys Ala
130                 135                 140

Arg Phe Tyr Ala Ala Gln Ile Val Leu Tyr Phe Glu Tyr Leu His Ser
145                 150                 155                 160

Leu Asp Leu Ile Tyr Arg Asp Leu Lys Pro Glu Asn Leu Leu Ile Asp
                165                 170                 175

Gln Gln Gly Tyr Ile Gln Val Thr Asp Phe Gly Phe Ala Lys Arg Val
            180                 185                 190

Lys Gly Arg Thr Trp Thr Leu Cys Gly Thr Pro Glu Tyr Leu Ala Pro
            195                 200                 205

Glu Ile Ile Leu Ser Lys Gly Tyr Asn Lys Ala Val Asp Trp Trp Ala
            210                 215                 220

Leu Gly Val Leu Ile Tyr Glu Met Ala Ala Gly Tyr Pro Pro Phe Phe
225                 230                 235                 240

Ala Asp Gln Pro Ile Gln Ile Tyr Glu Lys Ile Val Ser Gly Lys Val
                245                 250                 255

Arg Phe Pro Ser His Phe Ser Ser Asp Leu Lys Asp Leu Leu Arg Asn
            260                 265                 270

Leu Leu Gln Val Asp Leu Thr Lys Arg Phe Gly Asn Leu Lys Asn Gly
            275                 280                 285

Val Asn Asp Ile Lys Asn His Lys Trp Phe Ala Thr Thr Asp Trp Ile
            290                 295                 300

Ala Ile Tyr Gln Arg Lys Val Glu Ala Pro Phe Ile Pro Lys Phe Lys
305                 310                 315                 320

Gly Pro Gly Asp Thr Ser Asn Phe Asp Asp Tyr Glu Glu Glu Glu Ile
                325                 330                 335

Arg Val Ser Ile Asn Glu Lys Cys Gly Lys Glu Phe Ser Glu Phe
            340                 345                 350

<210> SEQ ID NO 81
<211> LENGTH: 38
<212> TYPE: PRT
<213> ORGANISM: Homo sapiens

<400> SEQUENCE: 81

Ser Glu Gln Glu Ser Val Lys Glu Phe Leu Ala Lys Ala Lys Glu Asp
1               5                   10                  15

Phe Leu Lys Lys Trp Glu Ser Pro Ala Gln Asn Thr Ala His Leu Asp
            20                  25                  30

Gln Phe Glu Arg Ile Lys
        35

<210> SEQ ID NO 82
<211> LENGTH: 15
<212> TYPE: PRT
<213> ORGANISM: Homo sapiens

<400> SEQUENCE: 82

Val Lys Glu Phe Leu Ala Lys Ala Lys Glu Asp Phe Leu Lys Lys
1               5                   10                  15

<210> SEQ ID NO 83
```

```
<211> LENGTH: 15
<212> TYPE: PRT
<213> ORGANISM: Homo sapiens

<400> SEQUENCE: 83

Phe Leu Ala Lys Ala Lys Glu Asp Phe Leu Lys Lys Trp Glu Ser
1               5                   10                  15

<210> SEQ ID NO 84
<211> LENGTH: 15
<212> TYPE: PRT
<213> ORGANISM: Homo sapiens

<400> SEQUENCE: 84

Lys Ala Lys Glu Asp Phe Leu Lys Lys Trp Glu Ser Pro Ala Gln
1               5                   10                  15

<210> SEQ ID NO 85
<211> LENGTH: 15
<212> TYPE: PRT
<213> ORGANISM: Homo sapiens

<400> SEQUENCE: 85

Glu Asp Phe Leu Lys Lys Trp Glu Ser Pro Ala Gln Asn Thr Ala
1               5                   10                  15

<210> SEQ ID NO 86
<211> LENGTH: 15
<212> TYPE: PRT
<213> ORGANISM: Homo sapiens

<400> SEQUENCE: 86

Leu Lys Lys Trp Glu Ser Pro Ala Gln Asn Thr Ala His Leu Asp
1               5                   10                  15

<210> SEQ ID NO 87
<211> LENGTH: 15
<212> TYPE: PRT
<213> ORGANISM: Homo sapiens

<400> SEQUENCE: 87

Trp Glu Ser Pro Ala Gln Asn Thr Ala His Leu Asp Gln Phe Glu
1               5                   10                  15

<210> SEQ ID NO 88
<211> LENGTH: 15
<212> TYPE: PRT
<213> ORGANISM: Homo sapiens

<400> SEQUENCE: 88

Pro Ala Gln Asn Thr Ala His Leu Asp Gln Phe Glu Arg Ile Lys
1               5                   10                  15

<210> SEQ ID NO 89
<211> LENGTH: 55
<212> TYPE: PRT
<213> ORGANISM: Homo sapiens

<400> SEQUENCE: 89

Met Ala Lys Arg Gly Ala Arg Ser Thr Ala Thr Trp Thr Leu Cys Gly
1               5                   10                  15

Thr Pro Glu Tyr Leu Ala Pro Glu Ile Ile Leu Ser Lys Gly Tyr Asn
            20                  25                  30

Lys Ala Val Asp Trp Trp Ala Leu Gly Val Leu Ile Tyr Glu Met Ala
```

```
            35                  40                  45

Ala Gly Tyr Pro Pro Phe Phe
    50                  55

<210> SEQ ID NO 90
<211> LENGTH: 351
<212> TYPE: PRT
<213> ORGANISM: Homo sapiens

<400> SEQUENCE: 90

Met Gly Asn Ala Ala Ala Lys Lys Gly Ser Glu Gln Glu Ser Val
1               5                   10                  15

Lys Glu Phe Leu Ala Lys Ala Lys Glu Asp Phe Leu Lys Lys Trp Glu
                20                  25                  30

Ser Pro Ala Gln Asn Thr Ala His Leu Asp Gln Phe Glu Arg Ile Lys
            35                  40                  45

Thr Leu Gly Thr Gly Ser Phe Gly Arg Val Met Leu Val Lys His Lys
        50                  55                  60

Glu Thr Gly Asn His Tyr Ala Met Lys Ile Leu Asp Lys Gln Lys Val
65                  70                  75                  80

Val Lys Leu Lys Gln Ile Glu His Thr Leu Asn Glu Lys Arg Ile Leu
                85                  90                  95

Gln Ala Val Asn Phe Pro Phe Leu Val Lys Leu Glu Phe Ser Phe Lys
            100                 105                 110

Asp Asn Ser Asn Leu Tyr Met Val Met Glu Tyr Val Pro Gly Gly Glu
        115                 120                 125

Met Phe Ser His Leu Arg Arg Ile Gly Arg Phe Ser Glu Pro Lys Ala
    130                 135                 140

Arg Phe Tyr Ala Ala Gln Ile Val Leu Tyr Phe Glu Tyr Leu His Ser
145                 150                 155                 160

Leu Asp Leu Ile Tyr Arg Asp Leu Lys Pro Glu Asn Leu Leu Ile Asp
                165                 170                 175

Gln Gln Gly Tyr Ile Gln Val Thr Asp Phe Gly Phe Ala Lys Arg Val
            180                 185                 190

Lys Gly Arg Thr Trp Thr Leu Cys Gly Thr Pro Glu Tyr Leu Ala Pro
        195                 200                 205

Glu Ile Ile Leu Ser Lys Gly Tyr Asn Lys Ala Val Asp Trp Trp Ala
    210                 215                 220

Leu Gly Val Leu Ile Tyr Glu Met Ala Ala Gly Tyr Pro Pro Phe Phe
225                 230                 235                 240

Ala Asp Gln Pro Ile Gln Ile Tyr Glu Lys Ile Val Ser Gly Lys Val
                245                 250                 255

Arg Phe Pro Ser His Phe Ser Ser Asp Leu Lys Asp Leu Leu Arg Asn
            260                 265                 270

Leu Leu Gln Val Asp Leu Thr Lys Arg Phe Gly Asn Leu Lys Asn Gly
        275                 280                 285

Val Asn Asp Ile Lys Asn His Lys Trp Phe Ala Thr Thr Asp Trp Ile
    290                 295                 300

Ala Ile Tyr Gln Arg Lys Val Glu Ala Pro Phe Ile Pro Lys Phe Lys
305                 310                 315                 320

Gly Pro Gly Asp Thr Ser Asn Phe Asp Asp Tyr Glu Glu Glu Glu Ile
                325                 330                 335

Arg Val Ser Ile Asn Glu Lys Cys Gly Lys Glu Phe Ser Glu Phe
            340                 345                 350
```

<210> SEQ ID NO 91
<211> LENGTH: 55
<212> TYPE: PRT
<213> ORGANISM: Homo sapiens

<400> SEQUENCE: 91

Lys Arg Val Lys Gly Arg Thr Trp Thr Leu Cys Gly Thr Pro Glu Tyr
1               5                   10                  15

Leu Ala Pro Glu Ile Ile Leu Ser Lys Gly Tyr Asn Lys Ala Val Asp
            20                  25                  30

Trp Trp Ala Leu Gly Val Leu Ile Tyr Glu Met Ala Ala Gly Tyr Pro
        35                  40                  45

Pro Phe Phe Ala Asp Gln Pro
    50                  55

<210> SEQ ID NO 92
<211> LENGTH: 15
<212> TYPE: PRT
<213> ORGANISM: Homo sapiens

<400> SEQUENCE: 92

Thr Trp Thr Leu Cys Gly Thr Pro Glu Tyr Leu Ala Pro Glu Ile
1               5                   10                  15

<210> SEQ ID NO 93
<211> LENGTH: 15
<212> TYPE: PRT
<213> ORGANISM: Homo sapiens

<400> SEQUENCE: 93

Leu Cys Gly Thr Pro Glu Tyr Leu Ala Pro Glu Ile Ile Leu Ser
1               5                   10                  15

<210> SEQ ID NO 94
<211> LENGTH: 15
<212> TYPE: PRT
<213> ORGANISM: Homo sapiens

<400> SEQUENCE: 94

Thr Pro Glu Tyr Leu Ala Pro Glu Ile Ile Leu Ser Lys Gly Tyr
1               5                   10                  15

<210> SEQ ID NO 95
<211> LENGTH: 15
<212> TYPE: PRT
<213> ORGANISM: Homo sapiens

<400> SEQUENCE: 95

Tyr Leu Ala Pro Glu Ile Ile Leu Ser Lys Gly Tyr Asn Lys Ala
1               5                   10                  15

<210> SEQ ID NO 96
<211> LENGTH: 15
<212> TYPE: PRT
<213> ORGANISM: Homo sapiens

<400> SEQUENCE: 96

Pro Glu Ile Ile Leu Ser Lys Gly Tyr Asn Lys Ala Val Asp Trp
1               5                   10                  15

<210> SEQ ID NO 97
<211> LENGTH: 15
<212> TYPE: PRT

```
<213> ORGANISM: Homo sapiens

<400> SEQUENCE: 97

Ile Leu Ser Lys Gly Tyr Asn Lys Ala Val Asp Trp Trp Ala Leu
1               5                   10                  15

<210> SEQ ID NO 98
<211> LENGTH: 15
<212> TYPE: PRT
<213> ORGANISM: Homo sapiens

<400> SEQUENCE: 98

Lys Gly Tyr Asn Lys Ala Val Asp Trp Trp Ala Leu Gly Val Leu
1               5                   10                  15

<210> SEQ ID NO 99
<211> LENGTH: 15
<212> TYPE: PRT
<213> ORGANISM: Homo sapiens

<400> SEQUENCE: 99

Asn Lys Ala Val Asp Trp Trp Ala Leu Gly Val Leu Ile Tyr Glu
1               5                   10                  15

<210> SEQ ID NO 100
<211> LENGTH: 15
<212> TYPE: PRT
<213> ORGANISM: Homo sapiens

<400> SEQUENCE: 100

Val Asp Trp Trp Ala Leu Gly Val Leu Ile Tyr Glu Met Ala Ala
1               5                   10                  15

<210> SEQ ID NO 101
<211> LENGTH: 15
<212> TYPE: PRT
<213> ORGANISM: Homo sapiens

<400> SEQUENCE: 101

Trp Ala Leu Gly Val Leu Ile Tyr Glu Met Ala Ala Gly Tyr Pro
1               5                   10                  15

<210> SEQ ID NO 102
<211> LENGTH: 15
<212> TYPE: PRT
<213> ORGANISM: Homo sapiens

<400> SEQUENCE: 102

Gly Val Leu Ile Tyr Glu Met Ala Ala Gly Tyr Pro Pro Phe Phe
1               5                   10                  15

<210> SEQ ID NO 103
<211> LENGTH: 699
<212> TYPE: PRT
<213> ORGANISM: Homo sapiens

<400> SEQUENCE: 103

Met Ser Val Val Gly Ile Asp Leu Gly Phe Gln Ser Cys Thr Val Ala
1               5                   10                  15

Val Ala Arg Ala Gly Gly Ile Glu Thr Ile Ala Asn Glu Tyr Ser Asp
                20                  25                  30

Arg Cys Thr Pro Ala Cys Ile Ser Phe Gly Pro Lys Asn Arg Ser Ile
            35                  40                  45
```

```
Gly Ala Ala Ala Lys Ser Gln Val Ile Ser Asn Ala Lys Asn Thr Val
 50                  55                  60

Gln Gly Phe Lys Arg Phe His Gly Arg Ala Phe Ser Asp Pro Phe Val
 65                  70                  75                  80

Glu Ala Glu Lys Ser Asn Leu Ala Tyr Asp Ile Val Gln Trp Pro Thr
                 85                  90                  95

Gly Leu Thr Gly Ile Lys Val Thr Tyr Met Glu Glu Arg Asn Phe
            100                 105                 110

Thr Thr Glu Gln Val Thr Ala Met Leu Leu Ser Lys Leu Lys Glu Thr
            115                 120                 125

Ala Glu Ser Val Leu Lys Pro Val Asp Cys Val Val Ser Val
130                 135                 140

Pro Cys Phe Tyr Thr Asp Ala Glu Arg Arg Ser Val Met Asp Ala Thr
145                 150                 155                 160

Gln Ile Ala Gly Leu Asn Cys Leu Arg Leu Met Asn Glu Thr Thr Ala
                165                 170                 175

Val Ala Leu Ala Tyr Gly Ile Tyr Lys Gln Asp Leu Pro Arg Leu Glu
            180                 185                 190

Glu Lys Pro Arg Asn Val Val Phe Val Asp Met Gly His Ser Ala Tyr
            195                 200                 205

Gln Val Ser Val Cys Ala Phe Asn Arg Gly Lys Leu Lys Leu Ala Thr
            210                 215                 220

Ala Phe Asp Thr Thr Leu Gly Gly Arg Lys Phe Asp Glu Val Leu Val
225                 230                 235                 240

Asn His Phe Cys Glu Glu Phe Gly Lys Lys Tyr Lys Leu Asp Ile Lys
                245                 250                 255

Ser Lys Ile Arg Ala Leu Leu Arg Leu Ser Gln Glu Cys Glu Lys Leu
            260                 265                 270

Lys Lys Leu Met Ser Ala Asn Ala Ser Asp Leu Pro Leu Ser Ile Glu
            275                 280                 285

Cys Phe Met Asn Asp Val Asp Val Ser Gly Thr Met Asn Arg Gly Lys
290                 295                 300

Phe Leu Glu Met Cys Asn Asp Leu Leu Ala Arg Val Glu Pro Pro Leu
305                 310                 315                 320

Arg Ser Val Leu Glu Gln Thr Lys Leu Lys Lys Glu Asp Ile Tyr Ala
                325                 330                 335

Val Glu Ile Val Gly Gly Ala Thr Arg Ile Pro Ala Val Lys Glu Lys
            340                 345                 350

Ile Ser Lys Phe Phe Gly Lys Glu Leu Ser Thr Thr Leu Asn Ala Asp
            355                 360                 365

Glu Ala Val Thr Arg Gly Cys Ala Leu Gln Cys Ala Ile Leu Ser Pro
370                 375                 380

Ala Phe Lys Val Arg Glu Phe Ser Ile Thr Asp Val Val Pro Tyr Pro
385                 390                 395                 400

Ile Ser Leu Arg Trp Asn Ser Pro Ala Glu Gly Ser Ser Asp Cys
                405                 410                 415

Glu Val Phe Ser Lys Asn His Ala Ala Pro Phe Ser Lys Val Leu Thr
            420                 425                 430

Phe Tyr Arg Lys Glu Pro Phe Thr Leu Glu Ala Tyr Tyr Ser Ser Pro
            435                 440                 445

Gln Asp Leu Pro Tyr Pro Asp Pro Ala Ile Ala Gln Phe Ser Val Gln
450                 455                 460

Lys Val Thr Pro Gln Ser Asp Gly Ser Ser Ser Lys Val Lys Val Lys
```

```
                465                 470                 475                 480
Val Arg Val Asn Val His Gly Ile Phe Ser Val Ser Ala Ser Leu
                    485                 490                 495

Val Glu Val His Lys Ser Glu Glu Asn Glu Glu Pro Met Glu Thr Asp
                500                 505                 510

Gln Asn Ala Lys Glu Glu Glu Lys Met Gln Val Asp Gln Glu Pro
                515                 520                 525

His Val Glu Glu Gln Gln Gln Thr Pro Ala Glu Asn Lys Ala Glu
    530                 535                 540

Ser Glu Glu Met Glu Thr Ser Gln Ala Gly Ser Lys Asp Lys Met
545                 550                 555                 560

Asp Gln Pro Pro Gln Cys Gln Glu Gly Lys Ser Glu Asp Gln Tyr Cys
                565                 570                 575

Gly Pro Ala Asn Arg Glu Ser Ala Ile Trp Gln Ile Asp Glu Met Leu
                580                 585                 590

Asn Leu Tyr Ile Glu Asn Glu Gly Lys Met Ile Met Gln Asp Lys Leu
                595                 600                 605

Glu Lys Glu Arg Asn Asp Ala Lys Asn Ala Val Glu Glu Tyr Val Tyr
                610                 615                 620

Glu Met Arg Asp Lys Leu Ser Gly Glu Tyr Glu Lys Phe Val Ser Glu
625                 630                 635                 640

Asp Asp Arg Asn Ser Phe Thr Leu Lys Leu Glu Asp Thr Glu Asn Trp
                645                 650                 655

Leu Tyr Glu Asp Gly Glu Asp Gln Pro Lys Gln Val Tyr Val Asp Lys
                660                 665                 670

Leu Ala Glu Leu Lys Asn Leu Gly Gln Pro Ile Lys Ile Arg Phe Gln
                675                 680                 685

Glu Ser Glu Glu Arg Pro Asn Tyr Leu Lys Asn
                690                 695

<210> SEQ ID NO 104
<211> LENGTH: 96
<212> TYPE: PRT
<213> ORGANISM: Homo sapiens

<400> SEQUENCE: 104

Met Ala Lys Arg Gly Ala Arg Ser Thr Ala Lys Ser Gln Val Ile Ser
1               5                   10                  15

Asn Ala Lys Asn Thr Val Gln Gly Phe Lys Arg Phe His Gly Arg Ala
                20                  25                  30

Phe Ser Asp Pro Phe Val Glu Ala Glu Lys Ser Asn Leu Ala Tyr Asp
            35                  40                  45

Ile Val Gln Trp Pro Thr Gly Leu Thr Gly Ile Lys Val Thr Tyr Met
        50                  55                  60

Glu Glu Glu Arg Asn Phe Thr Thr Glu Gln Val Thr Ala Met Leu Leu
65                  70                  75                  80

Ser Lys Leu Lys Glu Thr Ala Glu Ser Val Leu Lys Lys Pro Val Val
                85                  90                  95

<210> SEQ ID NO 105
<211> LENGTH: 32
<212> TYPE: PRT
<213> ORGANISM: Homo sapiens

<400> SEQUENCE: 105

Gly Ala Ala Ala Lys Ser Gln Val Ile Ser Asn Ala Lys Asn Tyr Val
```

```
                1               5                   10                  15
            Gln Gly Phe Lys Arg Phe His Gly Arg Ala Phe Ser Asp Pro Phe Val
                        20                  25                  30

<210> SEQ ID NO 106
<211> LENGTH: 18
<212> TYPE: PRT
<213> ORGANISM: Homo sapiens

<400> SEQUENCE: 106

Ala Ala Lys Ser Gln Val Ile Ser Asn Ala Lys Asn Tyr Val Gln Gly
1               5                   10                  15

Phe Lys

<210> SEQ ID NO 107
<211> LENGTH: 18
<212> TYPE: PRT
<213> ORGANISM: Homo sapiens

<400> SEQUENCE: 107

Lys Ser Gln Val Ile Ser Asn Ala Lys Asn Tyr Val Gln Gly Phe Lys
1               5                   10                  15

Arg Phe

<210> SEQ ID NO 108
<211> LENGTH: 18
<212> TYPE: PRT
<213> ORGANISM: Homo sapiens

<400> SEQUENCE: 108

Gln Val Ile Ser Asn Ala Lys Asn Tyr Val Gln Gly Phe Lys Arg Phe
1               5                   10                  15

His Gly

<210> SEQ ID NO 109
<211> LENGTH: 18
<212> TYPE: PRT
<213> ORGANISM: Homo sapiens

<400> SEQUENCE: 109

Ile Ser Asn Ala Lys Asn Tyr Val Gln Gly Phe Lys Arg Phe His Gly
1               5                   10                  15

Arg Ala

<210> SEQ ID NO 110
<211> LENGTH: 18
<212> TYPE: PRT
<213> ORGANISM: Homo sapiens

<400> SEQUENCE: 110

Asn Ala Lys Asn Tyr Val Gln Gly Phe Lys Arg Phe His Gly Arg Ala
1               5                   10                  15

Phe Ser

<210> SEQ ID NO 111
<211> LENGTH: 65
<212> TYPE: PRT
<213> ORGANISM: Homo sapiens

<400> SEQUENCE: 111

Met Ala Lys Arg Gly Ala Arg Ser Thr Ala Ile Met Gln Asp Lys Leu
```

```
                1               5                  10                 15
            Glu Lys Glu Arg Asn Asp Ala Lys Asn Ala Val Glu Glu Tyr Val Tyr
                            20                 25                 30
            Glu Met Arg Asp Lys Leu Ser Gly Glu Tyr Glu Lys Phe Val Ser Glu
                        35                 40                 45
            Asp Asp Arg Asn Ser Phe Thr Leu Lys Leu Glu Asp Thr Glu Asn Trp
                50                 55                 60
            Leu
            65

<210> SEQ ID NO 112
<211> LENGTH: 34
<212> TYPE: PRT
<213> ORGANISM: Homo sapiens

<400> SEQUENCE: 112

Met Ala Lys Arg Gly Ala Arg Ser Thr Ala Pro Leu Ile Phe Pro Ala
            1               5                  10                 15
            Glu Pro Ala Gln Ala Ser Gly Pro Tyr Val Glu Ile Ile Glu Gln Pro
                        20                 25                 30
            Lys Gln

<210> SEQ ID NO 113
<211> LENGTH: 550
<212> TYPE: PRT
<213> ORGANISM: Homo sapiens

<400> SEQUENCE: 113

Met Asp Glu Leu Phe Pro Leu Ile Phe Pro Ala Glu Pro Ala Gln Ala
            1               5                  10                 15
            Ser Gly Pro Tyr Val Glu Ile Ile Glu Gln Pro Lys Gln Arg Gly Met
                        20                 25                 30
            Arg Phe Arg Tyr Lys Cys Glu Gly Arg Ser Ala Gly Ser Ile Pro Gly
                        35                 40                 45
            Arg Arg Ser Thr Asp Thr Thr Lys Thr His Pro Thr Ile Lys Ile Asn
                50                 55                 60
            Gly Tyr Thr Gly Pro Gly Thr Val Arg Ile Ser Leu Val Thr Lys Asp
            65                 70                 75                 80
            Pro Pro His Arg Pro His Pro His Glu Leu Val Gly Lys Asp Cys Arg
                            85                 90                 95
            Asp Gly Phe Tyr Glu Ala Glu Leu Cys Pro Asp Arg Cys Ile His Ser
                        100                105                110
            Phe Gln Asn Leu Gly Ile Gln Cys Val Lys Lys Arg Asp Leu Glu Gln
                        115                120                125
            Ala Ile Ser Gln Arg Ile Gln Thr Asn Asn Asn Pro Phe Gln Val Pro
                    130                135                140
            Ile Glu Glu Gln Arg Gly Asp Tyr Asp Leu Asn Ala Val Arg Leu Cys
            145                150                155                160
            Phe Gln Val Thr Val Arg Asp Pro Ser Gly Arg Pro Leu Arg Leu Pro
                            165                170                175
            Pro Val Leu Ser His Pro Ile Phe Asp Asn Arg Ala Pro Asn Thr Ala
                        180                185                190
            Glu Leu Lys Ile Cys Arg Val Asn Arg Asn Ser Gly Ser Cys Leu Gly
                        195                200                205
            Gly Asp Glu Ile Phe Leu Leu Cys Asp Lys Val Gln Lys Glu Asp Ile
                    210                215                220
```

Glu Val Tyr Phe Thr Gly Pro Gly Trp Glu Ala Arg Gly Ser Phe Ser
225                 230                 235                 240

Gln Ala Asp Val His Arg Gln Val Ala Ile Val Phe Arg Thr Pro Pro
                245                 250                 255

Tyr Ala Asp Pro Ser Leu Gln Ala Pro Val Arg Val Ser Met Gln Leu
            260                 265                 270

Arg Arg Pro Ser Asp Arg Glu Leu Ser Glu Pro Met Glu Phe Gln Tyr
        275                 280                 285

Leu Pro Asp Thr Asp Asp Arg His Arg Ile Glu Glu Lys Arg Lys Arg
    290                 295                 300

Thr Tyr Glu Thr Phe Lys Ser Ile Met Lys Lys Ser Pro Phe Ser Gly
305                 310                 315                 320

Pro Thr Asp Pro Arg Pro Pro Arg Arg Ile Ala Val Pro Ser Arg
                325                 330                 335

Ser Ser Ala Ser Val Pro Lys Pro Ala Pro Gln Pro Tyr Pro Phe Thr
            340                 345                 350

Ser Ser Leu Ser Thr Ile Asn Tyr Asp Glu Phe Pro Thr Met Val Phe
        355                 360                 365

Pro Ser Gly Arg Ser Ala Arg Pro Arg Leu Gly Pro Ala Pro Pro Gln
    370                 375                 380

Val Leu Pro Gln Ala Pro Ala Pro Ala Pro Ala Pro Ala Met Val Ser
385                 390                 395                 400

Ala Leu Ala Gln Ala Pro Ala Pro Val Pro Val Leu Ala Pro Gly Pro
                405                 410                 415

Pro Gln Ala Val Ala Pro Pro Ala Pro Lys Pro Thr Gln Ala Gly Glu
            420                 425                 430

Gly Thr Leu Ser Glu Ala Leu Leu Gln Leu Gln Phe Asp Asp Glu Asp
        435                 440                 445

Leu Gly Ala Leu Leu Gly Asn Ser Thr Asp Pro Ala Val Phe Thr Asp
    450                 455                 460

Leu Ala Ser Val Asp Asn Ser Glu Phe Gln Gln Leu Leu Asn Gln Gly
465                 470                 475                 480

Ile Pro Val Ala Pro His Thr Thr Glu Pro Met Leu Met Glu Tyr Pro
                485                 490                 495

Glu Ala Ile Thr Arg Leu Val Thr Gly Ala Gln Arg Pro Pro Asp Pro
            500                 505                 510

Ala Pro Ala Pro Leu Gly Ala Pro Gly Leu Pro Asn Gly Leu Leu Ser
        515                 520                 525

Gly Asp Glu Asp Phe Ser Ser Ile Ala Asp Met Asp Phe Ser Ala Leu
    530                 535                 540

Leu Ser Gln Ile Ser Ser
545                 550

<210> SEQ ID NO 114
<211> LENGTH: 48
<212> TYPE: PRT
<213> ORGANISM: Homo sapiens

<400> SEQUENCE: 114

Met Ala Lys Arg Gly Ala Arg Ser Thr Ala Val Lys Lys Arg Asp Leu
1               5                   10                  15

Glu Gln Ala Ile Ser Gln Arg Ile Gln Thr Asn Asn Asn Pro Phe Gln
                20                  25                  30

Val Pro Ile Glu Glu Gln Arg Gly Asp Tyr Asp Leu Asn Ala Val Arg

-continued

```
               35                  40                  45
```

<210> SEQ ID NO 115
<211> LENGTH: 27
<212> TYPE: PRT
<213> ORGANISM: Homo sapiens

<400> SEQUENCE: 115

```
Gln Ala Ile Ser Gln Arg Ile Gln Thr Asn Asn Asn Pro Phe Gln Val
1               5                   10                  15

Pro Ile Glu Glu Gln Arg Gly Asp Tyr Asp Leu
            20                  25
```

<210> SEQ ID NO 116
<211> LENGTH: 15
<212> TYPE: PRT
<213> ORGANISM: Homo sapiens

<400> SEQUENCE: 116

```
Gln Arg Ile Gln Thr Asn Asn Asn Pro Phe Gln Val Pro Ile Glu
1               5                   10                  15
```

<210> SEQ ID NO 117
<211> LENGTH: 15
<212> TYPE: PRT
<213> ORGANISM: Homo sapiens

<400> SEQUENCE: 117

```
Arg Ile Gln Thr Asn Asn Asn Pro Phe Gln Val Pro Ile Glu Glu
1               5                   10                  15
```

<210> SEQ ID NO 118
<211> LENGTH: 15
<212> TYPE: PRT
<213> ORGANISM: Homo sapiens

<400> SEQUENCE: 118

```
Ile Gln Thr Asn Asn Asn Pro Phe Gln Val Pro Ile Glu Glu Gln
1               5                   10                  15
```

<210> SEQ ID NO 119
<211> LENGTH: 15
<212> TYPE: PRT
<213> ORGANISM: Homo sapiens

<400> SEQUENCE: 119

```
Gln Thr Asn Asn Asn Pro Phe Gln Val Pro Ile Glu Glu Gln Arg
1               5                   10                  15
```

<210> SEQ ID NO 120
<211> LENGTH: 15
<212> TYPE: PRT
<213> ORGANISM: Homo sapiens

<400> SEQUENCE: 120

```
Thr Asn Asn Asn Pro Phe Gln Val Pro Ile Glu Glu Gln Arg Gly
1               5                   10                  15
```

<210> SEQ ID NO 121
<211> LENGTH: 15
<212> TYPE: PRT
<213> ORGANISM: Homo sapiens

<400> SEQUENCE: 121

Asn Asn Asn Pro Phe Gln Val Pro Ile Glu Glu Gln Arg Gly Asp
1               5                   10                  15

<210> SEQ ID NO 122
<211> LENGTH: 15
<212> TYPE: PRT
<213> ORGANISM: Homo sapiens

<400> SEQUENCE: 122

Asn Asn Pro Phe Gln Val Pro Ile Glu Glu Gln Arg Gly Asp Tyr
1               5                   10                  15

<210> SEQ ID NO 123
<211> LENGTH: 59
<212> TYPE: PRT
<213> ORGANISM: Homo sapiens

<400> SEQUENCE: 123

Met Ala Lys Arg Gly Ala Arg Ser Thr Ala Asn Ser Thr Asp Pro Ala
1               5                   10                  15

Val Phe Thr Asp Leu Ala Ser Val Asp Asn Ser Glu Phe Gln Gln Leu
                20                  25                  30

Leu Asn Gln Gly Ile Pro Val Ala Pro His Thr Thr Glu Pro Met Leu
            35                  40                  45

Met Glu Tyr Pro Glu Ala Ile Thr Arg Leu Val
        50                  55

<210> SEQ ID NO 124
<211> LENGTH: 30
<212> TYPE: PRT
<213> ORGANISM: Homo sapiens

<400> SEQUENCE: 124

Gly Asn Ser Thr Asp Pro Ala Val Phe Thr Asp Leu Ala Ser Val Asp
1               5                   10                  15

Asn Ser Glu Phe Gln Gln Leu Leu Asn Gln Gly Ile Pro Val
                20                  25                  30

<210> SEQ ID NO 125
<211> LENGTH: 15
<212> TYPE: PRT
<213> ORGANISM: Homo sapiens

<400> SEQUENCE: 125

Pro Ala Val Phe Thr Asp Leu Ala Ser Val Asp Asn Ser Glu Phe
1               5                   10                  15

<210> SEQ ID NO 126
<211> LENGTH: 15
<212> TYPE: PRT
<213> ORGANISM: Homo sapiens

<400> SEQUENCE: 126

Ala Val Phe Thr Asp Leu Ala Ser Val Asp Asn Ser Glu Phe Gln
1               5                   10                  15

<210> SEQ ID NO 127
<211> LENGTH: 15
<212> TYPE: PRT
<213> ORGANISM: Homo sapiens

<400> SEQUENCE: 127

Val Phe Thr Asp Leu Ala Ser Val Asp Asn Ser Glu Phe Gln Gln

```
                1               5                   10                  15

<210> SEQ ID NO 128
<211> LENGTH: 15
<212> TYPE: PRT
<213> ORGANISM: Homo sapiens

<400> SEQUENCE: 128

Phe Thr Asp Leu Ala Ser Val Asp Asn Ser Glu Phe Gln Gln Leu
1               5                   10                  15

<210> SEQ ID NO 129
<211> LENGTH: 15
<212> TYPE: PRT
<213> ORGANISM: Homo sapiens

<400> SEQUENCE: 129

Thr Asp Leu Ala Ser Val Asp Asn Ser Glu Phe Gln Gln Leu Leu
1               5                   10                  15

<210> SEQ ID NO 130
<211> LENGTH: 15
<212> TYPE: PRT
<213> ORGANISM: Homo sapiens

<400> SEQUENCE: 130

Asp Leu Ala Ser Val Asp Asn Ser Glu Phe Gln Gln Leu Leu Asn
1               5                   10                  15

<210> SEQ ID NO 131
<211> LENGTH: 15
<212> TYPE: PRT
<213> ORGANISM: Homo sapiens

<400> SEQUENCE: 131

Leu Ala Ser Val Asp Asn Ser Glu Phe Gln Gln Leu Leu Asn Gln
1               5                   10                  15

<210> SEQ ID NO 132
<211> LENGTH: 15
<212> TYPE: PRT
<213> ORGANISM: Homo sapiens

<400> SEQUENCE: 132

Ala Ser Val Asp Asn Ser Glu Phe Gln Gln Leu Leu Asn Gln Gly
1               5                   10                  15

<210> SEQ ID NO 133
<211> LENGTH: 34
<212> TYPE: PRT
<213> ORGANISM: Homo sapiens

<400> SEQUENCE: 133

Met Ala Lys Arg Gly Ala Arg Ser Thr Ala Leu Asn Gly Val Asp Arg
1               5                   10                  15

Arg Ser Leu Gln Arg Ser Ala Lys Leu Ala Leu Glu Val Leu Glu Arg
                20                  25                  30

Ala Lys

<210> SEQ ID NO 134
<211> LENGTH: 210
<212> TYPE: PRT
<213> ORGANISM: Homo sapiens
```

<400> SEQUENCE: 134

Met Asp Asn Cys Leu Ala Ala Ala Leu Asn Gly Val Asp Arg Arg
1               5                   10                  15

Ser Leu Gln Arg Ser Ala Arg Leu Ala Leu Glu Val Leu Glu Arg Ala
            20                  25                  30

Lys Arg Arg Ala Val Asp Trp His Ala Leu Glu Arg Pro Lys Gly Cys
        35                  40                  45

Met Gly Val Leu Ala Arg Glu Ala Pro His Leu Glu Lys Gln Pro Ala
    50                  55                  60

Ala Gly Pro Gln Arg Val Leu Pro Gly Glu Arg Glu Arg Pro Pro
65                  70                  75                  80

Thr Leu Ser Ala Ser Phe Arg Thr Met Ala Glu Phe Met Asp Tyr Thr
                85                  90                  95

Ser Ser Gln Cys Gly Lys Tyr Tyr Ser Ser Val Pro Glu Glu Gly Gly
            100                 105                 110

Ala Thr His Val Tyr Arg Tyr His Arg Gly Glu Ser Lys Leu His Met
        115                 120                 125

Cys Leu Asp Ile Gly Asn Gly Gln Arg Lys Asp Arg Lys Thr Ser
130                 135                 140

Leu Gly Pro Gly Gly Ser Tyr Gln Ile Ser Glu His Ala Pro Glu Ala
145                 150                 155                 160

Ser Gln Pro Ala Glu Asn Ile Ser Lys Asp Leu Tyr Ile Glu Val Tyr
                165                 170                 175

Pro Gly Thr Tyr Ser Val Thr Val Gly Ser Asn Asp Leu Thr Lys Lys
            180                 185                 190

Thr His Val Val Ala Val Asp Ser Gly Gln Ser Val Asp Leu Val Phe
        195                 200                 205

Pro Val
    210

<210> SEQ ID NO 135
<211> LENGTH: 36
<212> TYPE: PRT
<213> ORGANISM: Homo sapiens

<400> SEQUENCE: 135

Leu Ala Ala Ala Leu Asn Gly Val Asp Arg Arg Ser Leu Gln Arg
1               5                   10                  15

Ser Gln Arg Leu Ala Leu Glu Val Leu Glu Arg Ala Lys Arg Arg Ala
            20                  25                  30

Val Asp Trp His
        35

<210> SEQ ID NO 136
<211> LENGTH: 18
<212> TYPE: PRT
<213> ORGANISM: Homo sapiens

<400> SEQUENCE: 136

Leu Asn Gly Val Asp Arg Arg Ser Leu Gln Arg Ser Gln Arg Leu Ala
1               5                   10                  15

Leu Glu

<210> SEQ ID NO 137
<211> LENGTH: 18
<212> TYPE: PRT
<213> ORGANISM: Homo sapiens

<400> SEQUENCE: 137

Asn Gly Val Asp Arg Arg Ser Leu Gln Arg Ser Gln Arg Leu Ala Leu
1               5                   10                  15

Glu Val

<210> SEQ ID NO 138
<211> LENGTH: 18
<212> TYPE: PRT
<213> ORGANISM: Homo sapiens

<400> SEQUENCE: 138

Gly Val Asp Arg Arg Ser Leu Gln Arg Ser Gln Arg Leu Ala Leu Glu
1               5                   10                  15

Val Leu

<210> SEQ ID NO 139
<211> LENGTH: 18
<212> TYPE: PRT
<213> ORGANISM: Homo sapiens

<400> SEQUENCE: 139

Val Asp Arg Arg Ser Leu Gln Arg Ser Gln Arg Leu Ala Leu Glu Val
1               5                   10                  15

Leu Glu

<210> SEQ ID NO 140
<211> LENGTH: 18
<212> TYPE: PRT
<213> ORGANISM: Homo sapiens

<400> SEQUENCE: 140

Asp Arg Arg Ser Leu Gln Arg Ser Gln Arg Leu Ala Leu Glu Val Leu
1               5                   10                  15

Glu Arg

<210> SEQ ID NO 141
<211> LENGTH: 18
<212> TYPE: PRT
<213> ORGANISM: Homo sapiens

<400> SEQUENCE: 141

Arg Arg Ser Leu Gln Arg Ser Gln Arg Leu Ala Leu Glu Val Leu Glu
1               5                   10                  15

Arg Ala

<210> SEQ ID NO 142
<211> LENGTH: 18
<212> TYPE: PRT
<213> ORGANISM: Homo sapiens

<400> SEQUENCE: 142

Arg Ser Leu Gln Arg Ser Gln Arg Leu Ala Leu Glu Val Leu Glu Arg
1               5                   10                  15

Ala Lys

<210> SEQ ID NO 143
<211> LENGTH: 18
<212> TYPE: PRT
<213> ORGANISM: Homo sapiens -continued

<400> SEQUENCE: 143

Ser Leu Gln Arg Ser Gln Arg Leu Ala Leu Glu Val Leu Glu Arg Ala
1               5                   10                  15

Lys Arg

<210> SEQ ID NO 144
<211> LENGTH: 38
<212> TYPE: PRT
<213> ORGANISM: Homo sapiens

<400> SEQUENCE: 144

Met Ala Lys Arg Gly Ala Arg Ser Ser Thr Ala Asp Ile Gly Asn Gly
1               5                   10                  15

Gln Arg Lys Asp Arg Lys Lys Thr Ser Leu Gly Pro Gly Gly Ser Tyr
                20                  25                  30

Gln Ile Ser Glu His Ala
            35

<210> SEQ ID NO 145
<211> LENGTH: 34
<212> TYPE: PRT
<213> ORGANISM: Homo sapiens

<400> SEQUENCE: 145

His Met Cys Leu Asp Ile Gly Asn Gly Gln Lys Asp Arg Lys Lys
1               5                   10                  15

Thr Ser Leu Gly Pro Gly Gly Ser Tyr Gln Ile Ser Glu His Ala Pro
                20                  25                  30

Glu Ala

<210> SEQ ID NO 146
<211> LENGTH: 18
<212> TYPE: PRT
<213> ORGANISM: Homo sapiens

<400> SEQUENCE: 146

Asp Ile Gly Asn Gly Gln Arg Lys Asp Arg Lys Lys Thr Ser Leu Gly
1               5                   10                  15

Pro Gly

<210> SEQ ID NO 147
<211> LENGTH: 18
<212> TYPE: PRT
<213> ORGANISM: Homo sapiens

<400> SEQUENCE: 147

Ile Gly Asn Gly Gln Arg Lys Asp Arg Lys Lys Thr Ser Leu Gly Pro
1               5                   10                  15

Gly Gly

<210> SEQ ID NO 148
<211> LENGTH: 18
<212> TYPE: PRT
<213> ORGANISM: Homo sapiens

<400> SEQUENCE: 148

Gly Asn Gly Gln Arg Lys Asp Arg Lys Lys Thr Ser Leu Gly Pro Gly
1               5                   10                  15

Gly Ser

<210> SEQ ID NO 149
<211> LENGTH: 18
<212> TYPE: PRT
<213> ORGANISM: Homo sapiens

<400> SEQUENCE: 149

Asn Gly Gln Arg Lys Asp Arg Lys Lys Thr Ser Leu Gly Pro Gly Gly
1               5                   10                  15

Ser Tyr

<210> SEQ ID NO 150
<211> LENGTH: 18
<212> TYPE: PRT
<213> ORGANISM: Homo sapiens

<400> SEQUENCE: 150

Gly Gln Arg Lys Asp Arg Lys Lys Thr Ser Leu Gly Pro Gly Gly Ser
1               5                   10                  15

Tyr Gln

<210> SEQ ID NO 151
<211> LENGTH: 18
<212> TYPE: PRT
<213> ORGANISM: Homo sapiens

<400> SEQUENCE: 151

Gln Arg Lys Asp Arg Lys Lys Thr Ser Leu Gly Pro Gly Gly Ser Tyr
1               5                   10                  15

Gln Ile

<210> SEQ ID NO 152
<211> LENGTH: 18
<212> TYPE: PRT
<213> ORGANISM: Homo sapiens

<400> SEQUENCE: 152

Arg Lys Asp Arg Lys Lys Thr Ser Leu Gly Pro Gly Gly Ser Tyr Gln
1               5                   10                  15

Ile Ser

<210> SEQ ID NO 153
<211> LENGTH: 18
<212> TYPE: PRT
<213> ORGANISM: Homo sapiens

<400> SEQUENCE: 153

Lys Asp Arg Lys Lys Thr Ser Leu Gly Pro Gly Gly Ser Tyr Gln Ile
1               5                   10                  15

Ser Glu

<210> SEQ ID NO 154
<211> LENGTH: 18
<212> TYPE: PRT
<213> ORGANISM: Homo sapiens

<400> SEQUENCE: 154

Asp Arg Lys Lys Thr Ser Leu Gly Pro Gly Gly Ser Tyr Gln Ile Ser
1               5                   10                  15

Glu His

<210> SEQ ID NO 155
<211> LENGTH: 37
<212> TYPE: PRT
<213> ORGANISM: Homo sapiens

<400> SEQUENCE: 155

Met Ala Lys Arg Gly Ala Arg Ser Thr Ala Lys Tyr Tyr Ser Ser Val
1               5                   10                  15

Pro Glu Glu Gly Gly Ala Thr His Val Tyr Arg Tyr His Arg Gly Glu
            20                  25                  30

Ser Lys Leu His Met
        35

<210> SEQ ID NO 156
<211> LENGTH: 35
<212> TYPE: PRT
<213> ORGANISM: Homo sapiens

<400> SEQUENCE: 156

Ser Val Pro Glu Glu Gly Gly Ala Thr His Val Tyr Arg Tyr His Arg
1               5                   10                  15

Gly Glu Ser Lys Leu His Met Cys Leu Asp Ile Gly Asn Gly Gln Arg
            20                  25                  30

Lys Asp Arg
        35

<210> SEQ ID NO 157
<211> LENGTH: 18
<212> TYPE: PRT
<213> ORGANISM: Homo sapiens

<400> SEQUENCE: 157

Glu Glu Gly Gly Ala Thr His Val Tyr Arg Tyr His Arg Gly Glu Ser
1               5                   10                  15

Lys Leu

<210> SEQ ID NO 158
<211> LENGTH: 18
<212> TYPE: PRT
<213> ORGANISM: Homo sapiens

<400> SEQUENCE: 158

Glu Gly Gly Ala Thr His Val Tyr Arg Tyr His Arg Gly Glu Ser Lys
1               5                   10                  15

Leu His

<210> SEQ ID NO 159
<211> LENGTH: 18
<212> TYPE: PRT
<213> ORGANISM: Homo sapiens

<400> SEQUENCE: 159

Gly Gly Ala Thr His Val Tyr Arg Tyr His Arg Gly Glu Ser Lys Leu
1               5                   10                  15

His Met

<210> SEQ ID NO 160
<211> LENGTH: 18
<212> TYPE: PRT
<213> ORGANISM: Homo sapiens

<400> SEQUENCE: 160

```
Gly Ala Thr His Val Tyr Arg Tyr His Arg Gly Glu Ser Lys Leu His
1               5                   10                  15

Met Cys

<210> SEQ ID NO 161
<211> LENGTH: 18
<212> TYPE: PRT
<213> ORGANISM: Homo sapiens

<400> SEQUENCE: 161

Ala Thr His Val Tyr Arg Tyr His Arg Gly Glu Ser Lys Leu His Met
1               5                   10                  15

Cys Leu

<210> SEQ ID NO 162
<211> LENGTH: 18
<212> TYPE: PRT
<213> ORGANISM: Homo sapiens

<400> SEQUENCE: 162

Thr His Val Tyr Arg Tyr His Arg Gly Glu Ser Lys Leu His Met Cys
1               5                   10                  15

Leu Asp

<210> SEQ ID NO 163
<211> LENGTH: 18
<212> TYPE: PRT
<213> ORGANISM: Homo sapiens

<400> SEQUENCE: 163

His Val Tyr Arg Tyr His Arg Gly Glu Ser Lys Leu His Met Cys Leu
1               5                   10                  15

Asp Ile

<210> SEQ ID NO 164
<211> LENGTH: 18
<212> TYPE: PRT
<213> ORGANISM: Homo sapiens

<400> SEQUENCE: 164

Val Tyr Arg Tyr His Arg Gly Glu Ser Lys Leu His Met Cys Leu Asp
1               5                   10                  15

Ile Gly

<210> SEQ ID NO 165
<211> LENGTH: 18
<212> TYPE: PRT
<213> ORGANISM: Homo sapiens

<400> SEQUENCE: 165

Tyr Arg Tyr His Arg Gly Glu Ser Lys Leu His Met Cys Leu Asp Ile
1               5                   10                  15

Gly Asn

<210> SEQ ID NO 166
<211> LENGTH: 18
<212> TYPE: PRT
<213> ORGANISM: Homo sapiens
```

```
<400> SEQUENCE: 166

Arg Tyr His Arg Gly Glu Ser Lys Leu His Met Cys Leu Asp Ile Gly
1               5                   10                  15

Asn Gly

<210> SEQ ID NO 167
<211> LENGTH: 18
<212> TYPE: PRT
<213> ORGANISM: Homo sapiens

<400> SEQUENCE: 167

Tyr His Arg Gly Glu Ser Lys Leu His Met Cys Leu Asp Ile Gly Asn
1               5                   10                  15

Gly Gln

<210> SEQ ID NO 168
<211> LENGTH: 43
<212> TYPE: PRT
<213> ORGANISM: Homo sapiens

<400> SEQUENCE: 168

Met Ala Lys Arg Gly Ala Arg Ser Thr Ala Asp Asn Cys Leu Ala Ala
1               5                   10                  15

Ala Leu Asn Gly Val Asp Arg Arg Ser Leu Gln Arg Ser Ala Lys Leu
            20                  25                  30

Ala Leu Glu Val Leu Glu Arg Ala Lys Arg Arg
        35                  40

<210> SEQ ID NO 169
<211> LENGTH: 45
<212> TYPE: PRT
<213> ORGANISM: Homo sapiens

<400> SEQUENCE: 169

Thr Trp Thr Leu Cys Gly Thr Pro Glu Tyr Leu Ala Pro Glu Ile Ile
1               5                   10                  15

Leu Ser Lys Gly Tyr Asn Lys Ala Val Asp Trp Trp Ala Leu Gly Val
            20                  25                  30

Leu Ile Tyr Glu Met Ala Ala Gly Tyr Pro Pro Phe Phe
        35                  40                  45

<210> SEQ ID NO 170
<211> LENGTH: 10
<212> TYPE: PRT
<213> ORGANISM: Homo sapiens

<400> SEQUENCE: 170

Met Ala Lys Arg Gly Ala Arg Ser Thr Ala
1               5                   10
```